United States Patent [19]

Tsujihara et al.

[11] Patent Number: 5,731,292

[45] Date of Patent: *Mar. 24, 1998

[54] DIHYDROCHALCONE DERIVATIVES WHICH ARE HYPOGLYCEMIC AGENTS

[75] Inventors: Kenji Tsujihara, Urawa; Mitsuya Hongu, Omiya; Nobuyuki Funami, Tokyo-to; Masanori Inamasu, Misato; Kenji Arakawa, Urawa, all of Japan

[73] Assignee: Tanabe Seiyaku Co., Ltd., Osaka, Japan

[*] Notice: The term of this patent shall not extend beyond the expiration date of Pat. No. 5,424,406.

[21] Appl. No.: 426,002

[22] Filed: Apr. 20, 1995

Related U.S. Application Data

[63] Continuation-in-part of Ser. No. 149,912, Nov. 10, 1993, Pat. No. 5,424,406.

[30] Foreign Application Priority Data

Nov. 12, 1992 [JP] Japan ................................. 4-301485
Feb. 18, 1993 [JP] Japan ................................. 5-028770
Feb. 25, 1993 [JP] Japan ................................. 5-035988

[51] Int. Cl.$^6$ ........................................................ A61K 31/70
[52] U.S. Cl. ................................ 514/25; 514/23; 514/866; 536/4.1
[58] Field of Search ........................... 514/23, 25, 866; 536/4.1

[56] References Cited

U.S. PATENT DOCUMENTS

| | | | |
|---|---|---|---|
| 3,984,394 | 10/1976 | Westall et al. | 536/8 |
| 4,031,260 | 6/1977 | Westall et al. | 426/548 |
| 4,665,058 | 5/1987 | Deidrich et al. | 514/25 |
| 4,684,627 | 8/1987 | LeVeen et al. | 514/25 |
| 4,760,135 | 7/1988 | Diedrich et al. | 536/17.9 |
| 4,840,939 | 6/1989 | LeVeen et al. | 514/25 |
| 5,110,801 | 5/1992 | LeVeen et al. | 514/34 |
| 5,424,406 | 6/1995 | Tsujihara et al. | 536/4.1 |

OTHER PUBLICATIONS

D. Diedrich (1963) *Biochim. Biophys. Acta*, (71) 688–700.
Rosetti et al. (1990) *Diabetes Care* 13(6), 610–630.
Rosetti et al. (1987) *J. Clin. Invest.* (79) 1510–1515.
Rosetti et al. (1987) *J. Clin. Invest.* (80) 1037–1044.
Kahn et al. (1991) *J. Clin. Invest* (87) 561–570.
Unger et al. (1985) *Diabetologia* 28:119–121.
Olendorf et al. (1983) *Stroke* (14) 388–393.
Winget et al. (1969) *Biochemistry* (8) 2067–2074.
Vick et al. (1973) *Am. Journal of Physiology* 224 (3) 552–557.
D. Diedrich (1966) *Ar. of Biochem. and Biophy.* 117:248–256.
Evans et al. (1980) *Ar. of Biochem. and Biophy.* 199(2) 342–348.
Bode et al. (1972) *Biochim. Biophys. Acta*, 290 134–149.
Pzabo et al., *Acta Alimentaria*, vol. 11 (1), pp. 31–37.
Unger et al., *Diabetologia*, 28 (1985), 119–121.
"Guidelines for Toxicity Studies of Drugs," Ministry of Health and Welfare of Japan, 114–118.
Fujiwara et al., *Diabetes*, (37) (1988) 1549–1558.
*Dorland's Medical Dictionary*, 27 ed., pp. 460–461 (1988).
Odaka et al., *J. Nutr. Sci. Vitaminol*, 38 (1992) Abstract.

*Primary Examiner*—John Kight
*Assistant Examiner*—Howard C. Lee
*Attorney, Agent, or Firm*—Birch, Stewart, Kolasch & Birch, LLP

[57] ABSTRACT

A method for prophylaxis or treatment of diabetes, which comprises administering to a patient with diabetes an effective amount of a dihydrochalcone derivative of the formula [I]:

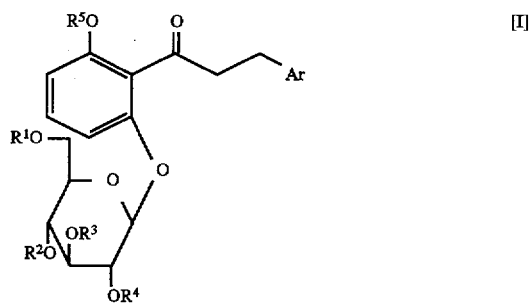

wherein Ar is an aryl group, $R^1$ is hydrogen atom or an acyl group, $R^2$ is a hydrogen atom, an acyl group or α-D-glucopyranosyl group, or $R^1$ and $R^2$ may combine together to form a substituted methylene group, $R^3$ and $R^4$ are each a hydrogen atom or an acyl group, $OR^5$ is a protected or unprotected hydroxy group or a lower alkoxy group, or a pharmaceutically acceptable salt thereof.

19 Claims, No Drawings

DIHYDROCHALCONE DERIVATIVES WHICH ARE HYPOGLYCEMIC AGENTS

This application is a continuation-in-part of application Ser. No. 08/149,912, filed on Nov. 10, 1993, the entire contents of which are hereby incorporated by reference.

The present invention relates to hypoglycemic agent comprising as an active ingredient a dihydrochalcone derivative or a pharmaceutically acceptable salt thereof.

PRIOR ART

Although diet therapy is essential in the treatment of diabetes, when diet therapy does not sufficiently control the conditions of patients, insulin or oral antidiabetic is additionally used. There have been used as an antidiabetic biguanide compounds and sulfonyl urea compounds, however, these antidiabetics have various side effects, for example, biguanide compounds cause lactic acidosis, and sulfonyl urea compounds cause significant hypoglycemia. Under such circumstances, it has been desired to develop novel drugs for treatment of diabetes having no side effects.

Recently, it has been reported that hyperglycemia participates in the outbreak and deterioration of diabetes, i.e. glucose toxicity theory. That is, chronic hyperglycemia leads to progressive impairment in insulin secretion and contributes to insulin resistance, and as a result, the blood glucose concentration is increased so that diabetes evaluates [cf. Diabetologia Vol. 28, p. 119 (1985), Diabetes Care, 13, 610 (1990), etc.].

This theory is proved as follows. When the blood glucose concentration in diabetic animals is controlled at normal for a long time without using insulin, the conditions of diabetic animals are ameliorated to normal [cf. Journal of Clinical Investigation, Vol. 79, p. 1510 (1987), Vol. 80, p. 1037 (1987), Vol. 87, p. 561 (1991 ), etc.]. In these investigations, phlorizin was used by subcutaneous administration as a drug to normalize the blood glucose concentration.

Phlorizin is a glycoside which exists in barks and stems of Rosaceae (e.g. apple, pear, etc.), and was discovered in the 19th century, and has been studied since. Recently, it has been found that phlorizin is an inhibitor of Na$^+$-glucose co-transporter which exists only at the chorionic membrane of the intestine and the kidney, and that phlorizin inhibits the renal tubular glucose reabsorption and promotes the excretion of glucose so that the blood glucose is controlled.

However, when phlorizin is administered orally, most of it is hydrolyzed into phloretin, which is the aglycon of phlorizin, and glucose, and hence, the amount of phlorizin to be absorbed is so little that the urine glucose excretion effect of phlorizin is very weak. Besides, phloretin, which is the aglycon of phlorizin, has been known to inhibit strongly facilitated diffusion-type glucose transport carrier, for example, when phloretin is intravenously administered to rats, the brain glucose is attenuated [cf. Stroke, Vol. 14, 388 (1983)]. However, when phlorizin is administered for a long time, there may be bad effects on various tissues, and hence, phlorizin has not been used as an antidiabetic.

Besides, 2'-O-(β-D-glucopyranosyl)-6'-hydroxydihydrochalcone, 2'-O-(β-D-glucopyranosyl)-4,6'-dihydroxydihydrochalcone and 2'-O-(β-D-glucopyranosyl)-6'-hydroxy-4-methoxydihydrochalcone have been known to inhibit photophosphorylation at chloroplast [cf. Biochemistry, Vol. 8, p. 2067 (1967)]. Moreover, 2'-O-(Δ-D-glucopyranosyl)-4,6'-dihydroxydihydrochalcone has also been known to inhibit Na$^+$-glucose co-transporter at the kidney [cf. Biochim. Biophys. Acta, Vol. 71, p. 688 (1963)].

However, it has never been disclosed that these compounds have urine glucose increasing activity even by oral administration.

BRIEF DESCRIPTION OF THE INVENTION

An object of the present invention is to provide dihydrochalcone derivatives which inhibit the renal tubular glucose reabsorption and/or inhibit the absorption of glucose at the intestine, and show excellent hypoglycemic activity as well as an aglycon thereof has weak inhibitory activity of facilitated diffusion-type glucose transport carrier. Another object of the present invention is to provide a hypoglycemic agent comprising as an active ingredient a dihydrochalcone derivative of the present invention or a pharmaceutically acceptable salt thereof.

DETAILED DESCRIPTION OF THE INVENTION

The present invention relates a hypoglycemic agent comprising as an active ingredient a dihydrochalcone derivative of the formula[I]:

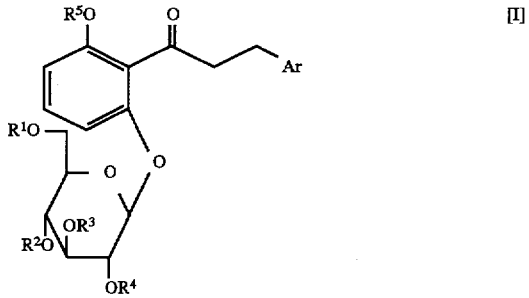

wherein Ar is an aryl group, R$^1$ is hydrogen atom or an acyl group, R$^2$ is hydrogen atom, an acyl group or α-D-glucopyranosyl group, or R$^1$ and R$^2$ may combine together to form a substituted methylene group, R$^3$ and R$^4$ are each hydrogen atom or an acyl group, and a group of the formula: OR$^5$ is a protected or unprotected hydroxy group or a lower alkoxy group, or a pharmaceutically acceptable salt thereof.

The dihydrochalcone derivatives [I], the active ingredient of the present invention, show excellent hypoglycemic activity based on the urine glucose increasing activity thereof. For example, when the active ingredient [I] of the present invention is administered to rats, the amount of glucose to be excreted into urine for 24 hours is about 5 to 40 times as much as those when phlorizin is administered. In addition, when the active ingredient [I] of the present invention is orally administered to glucose-loading diabetic mice, the increment in the blood glucose concentration thereof is remarkably attenuated. Thus, the hypoglycemic agent of the present invention is useful in the treatment of diabetes. The urine glucose increasing activity of the active ingredient [I] of the present invention is postulated to be based on the inhibitory activity of the renal glucose reabsorption, which is different from conventional hypoglycemic agents.

Besides, the active ingredient of the present invention possesses low toxicity, for example, when 2'-O-(β-D-glucopyranosyl)-6'-hydroxy-4-methoxydihydrochalcone or 2'-O-(2,3-di-O-ethoxyacetyl-β-D-glucopyranosyl)-6'-hydroxy-4-methoxydihydrochalcone was orally and continuously administered to rats at a dose of 1000 mg/kg for 28 days, no rat died.

The aglycone, which is a hydrolysate of the active ingredient of the present invention, is characteristic in its extremely weak glucose-uptake inhibitory activity, which is different from phloretin. For example, human erythrocyte was incubated with D-[3-$^3$H] glucose for one minute, and the radioactivity of the erythrocyte was measured in order to estimate the amount of glucose to be incorporated into the erythrocyte. In this experiment, when an aglycon of the active ingredient [I] of the present invention, 2',4,6'-trihydroxydihydrochalcone, or 2',6'-dihydroxy-4-methoxydihydrochalcone was added to the reaction system, the amount of glucose to be incorporated into the erythrocyte is 92.7%, and 91.0%, respectively as compared with the amount of glucose to be incorporated into the erythrocyte when no test compound was added. On the other hand, the amount of glucose to be incorporated into the erythrocyte was 13.7% when phloretin was added. Accordingly, the inhibitory activity of glucose incorporation into human erythrocyte of the aglycon of the active ingredient of the present is much smaller than that of phloretin, the aglycon of phlorizin, and hence, even though the active ingredient [I] of the present invention is partially hydrolyzed, the glucose concentration in tissues does not easily decrease.

In the active dihydrochalcone derivative [I] of the present invention, the "aryl group" means a hydrocarbon aryl group or a heterocyclic aryl group, and the "acyl group" means an aliphatic acyl group or an aromatic acyl group.

The "hydrocarbon aryl group" includes a phenyl group optionally having a substituent, or a naphthyl group optionally having a substituent. The "heterocyclic aryl group" includes heterocyclic groups containing as a hetero-atom a nitrogen atom, oxygen atom or sulfur atom, and said heterocyclic groups may optionally have a substituent, for example, a furyl group, thienyl group, pyridyl group, and the like. The "aliphatic acyl group" includes a lower alkanoyl group optionally having a substituent or a lower alkoxycarbonyl group optionally having a substituent. The "aromatic acyl group" includes a benzoyl group optionally having a substituent or a phenoxycarbonyl group optionally having a substituent.

When the above mentioned groups have a substituent, each group may have 1 to 2 substituents. The substituents for the above mentioned groups are a lower alkyl group optionally having a hydroxy substituent or a halogen substituent; a lower alkoxy group optionally having a lower alkoxy substituent; a lower alkoxycarbonyloxy group optionally having a lower alkoxy substituent; an amino group having a lower alkyl substituent; a protected or unprotected amino group; a lower alkanoyloxy group optionally having 1 to 2 substituents selected from a lower alkoxy group, a lower alkoxycarbonyl group, amino group and phenyl group; a halogen atom; hydroxy group; carbamoyl group; a lower alkylthio group; a lower alkylsulfinyl group; a lower alkylsulfonyl group; carboxyl group; formyl group; cyano group; di-lower alkylcarbamoyloxy group; phenoxycarbonyloxy group; phenyl group; phenoxy group; oxo group; a lower alkylenedioxy group; or a benzoyloxy group optionally having a lower alkoxy substituent.

When the above substituent is a protected amino group, the protecting group may be any one which can be a protecting group for amino group, for example, an acyl group such as a lower alkanoyl group, a phenyl-lower alkoxycarbonyl group, and the like.

When $R^1$ and $R^2$ combine together to form a substituted methylene group in the active compounds [I], the substituent for said methylene group is preferably a phenyl group, a lower alkanoyloxy group, a lower alkoxy group or oxo group, and especially, a phenyl group is more preferable. Said methylene group may be substituted by 1 to 2 groups selected from the above substituents.

When a group of the formula: $OR^5$ is a protected hydroxy group in the active compounds [I], the protecting groups may be ones which can be a protecting group for a phenolic hydroxy group, for example, an acyl group such as a lower alkanoyl group optionally substituted by a group selected from a lower alkoxy group, a lower alkoxycarbonyl group, phenyl group and amino group; a lower alkoxycarbonyl group; a lower alkoxy-lower alkoxycarbonyl group; phenoxycarbonyl group; benzoyl group; or a lower alkoxybenzoyl group.

Among the active dihydrochalcone derivatives of the present invention, a compound of the formula [I-A]:

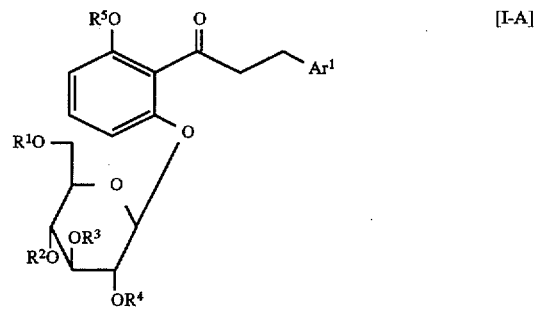

wherein $Ar^1$ is an aryl group, and $R^1$, $R^2$, $R^3$, $R^4$ and $OR^5$ are the same as defined above, provided that when $R^1$, $R^2$, $R^3$ and $R^4$ are all hydrogen atoms and $OR^5$ is a hydroxy group, $Ar^1$ is a group other than a 4-hydroxyphenyl group, 4-methoxyphenyl group and phenyl group, is a novel compound, and $Ar^1$ is the same groups as those for Ar, as mentioned above.

Among the active ingredients [I], preferable compounds are compounds of the formula [I], wherein (1) Ar is a phenyl group optionally having a substituent, a heterocyclic group containing as a heteroatom an oxygen atom, nitrogen atom or sulfur atom, or naphthyl group, the group of the formula: $OR^5$ is a protected or unprotected hydroxy group or a lower alkoxy group, and $R^1$, $R^2$, $R^3$ and $R^4$ are all hydrogen atom;

(2) Ar is a phenyl group optionally having a substituent, the group of the formula: $OR^5$ is a protected or unprotected hydroxy group or a lower alkoxy group, $R^1$, $R^3$ and $R^4$ are all hydrogen atoms, and $R^2$ is α-D-glucopyranosyl group;

(3) Ar is a phenyl group optionally having a substituent, the group of the formula: $OR^5$ is a protected or unprotected hydroxy group or a lower alkoxy group, $R^1$ and $R^2$ are both hydrogen atoms or both combine together to form a substituted methylene group, and $R^3$ and $R^4$ are each hydrogen atoms, a lower alkanoyl group optionally having a substituent, a lower alkoxycarbonyl group optionally having a substituent, an arylcarbonyl group or an aryloxycarbonyl group, provided that $R^1$, $R^2$, $R^3$ and $R^4$ are not simultaneously hydrogen atoms; or (4) Ar is a phenyl group optionally having a substituent, the group of the formula: $OR^5$ is a protected or unprotected hydroxy group or a lower alkoxy group, $R^1$ is a lower alkanoyl group optionally having a substituent, a lower alkoxycarbonyl group optionally having a substituent, an arylcarbonyl group or an aryloxycarbonyl group, $R^2$, $R^3$ and $R^4$ are the same or different and are each hydrogen atoms, a lower alkanoyl group optionally having a substituent, a lower alkoxycarbonyl group optionally having a substituent, an arylcarbonyl group or an aryloxycarbonyl group.

When the groups in above (1) to (4) have a substituent, the substituent may be the same groups for the substituent in the compound [I].

Other preferable compounds are compounds of the formula [I] wherein Ar is phenyl group, hydroxyphenyl group or a lower alkoxyphenyl group, $R^1$, $R^2$, $R^3$ and $R^4$ are all hydrogen atoms, and the group of the formula: $OR^5$ is hydroxy group.

The pharmaceutically preferable compounds [I] are compounds of the formula [I] wherein Ar is phenyl group, a lower alkyl-substituted phenyl group, a lower alkoxy-substituted phenyl group, a lower alkoxycarbonyloxy-substituted phenyl group or a halogenophenyl group, the group of the formula: $OR^5$ is a protected or unprotected hydroxy group, and $R^1$, $R^2$, $R^3$ and R4 are all hydrogen atoms, or compounds of the formula [I] wherein Ar is a phenyl group optionally having a substituent selected from a halogen atom, hydroxy group, a lower alkyl group, a lower alkoxy group, a lower alkanoyloxy group and a lower alkoxycarbonyloxy group, the group of the formula: $OR^5$ is a protected or unprotected hydroxy group, $R^1$ and $R^2$ are both hydrogen atoms, and $R^3$ and $R^4$ are each a lower alkanoyl group optionally having a substituent selected from a hydroxy group, a lower alkoxy group, a lower alkoxy-lower alkoxy group, benzyloxycarbonylamino group and amino group, a lower alkoxycarbonyl group, benzoyl group, or phenoxycarbonyl group.

The pharmaceutically more preferable compounds are compounds of the formula [I] wherein Ar is a phenyl group optionally having a substituent selected from a lower alkyl group and a lower alkoxy group, the group of the formula: $OR^5$ is hydroxy group or a hydroxy group protected by a lower alkanoyl group, $R^1$ and $R^2$ are both hydrogen atom, $R^3$ and $R^4$ are each a lower alkanoyl group, a lower alkoxy-substituted lower alkanoyl group, an amino-substituted lower alkanoyl group, a lower alkoxycarbonyl group or a phenoxycarbonyl group, and especially the compounds of the formula [I] wherein Ar is a lower alkoxy-substituted phenyl group, and $R^3$ and $R^4$ are each a lower alkoxy-substituted lower alkanoyl group are preferable.

Moreover, other preferable compounds are novel compounds of the formula [I-A].

Among the novel compounds [I-A], preferable compounds are compounds of the formula [I-a]:

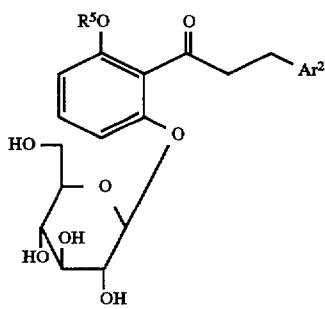

[I-a]

wherein $Ar^2$ is an aryl groups other than a phenyl group, 4-hydroxyphenyl group and 4-methoxyphenyl group, the group of the formula: $OR^5$ is the same as defined above, or compounds of the formula [I-b]:

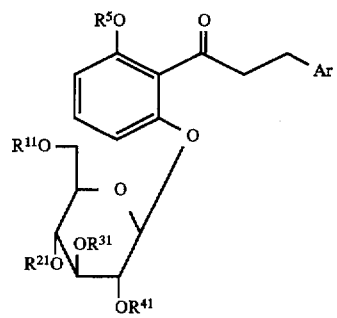

[I-b]

wherein $R^{11}$ is a hydrogen atom or an acyl group, $R^{21}$ is a hydrogen atom, an acyl group or an α-D-glucopyranosyl group, or $R^{11}$ and $R^{21}$ may combine together to form a substituted methylene group, and $R^{31}$ and $R^{41}$ are each hydrogen atom or an acyl group provided that $R^{11}$, $R^{21}$, $R^{31}$ and $R^{41}$ are not simultaneously hydrogen atom, and Ar and $OR^5$ are the same as defined above.

In the formulae [I-a] and [I-b], $Ar^2$, $R^{11}$, $R^{21}$, $R^{31}$ and $R^{41}$ are the same groups as Ar, $R^1$, $R^2$, $R^3$ and $R^4$, respectively.

Among the compounds [I-a], more preferable compounds are compounds of the formula [I-a] wherein $Ar^2$ is a phenyl group having 1 to 2 substituents; furyl group; thienyl group; pyridyl group; or naphthyl group, and the group of the formula: $OR^5$ is a protected or unprotected hydroxy group or a lower alkoxy group. When $Ar^2$ is a phenyl group having 1 to 2 substituents, the substituent for the phenyl group is a lower alkyl group optionally substituted by a halogen atom or hydroxy group; a lower alkoxy group having 2 to 6 carbon atoms; a lower alkoxy group having a lower alkoxy substituent; a lower alkoxycarbonyloxy group optionally having a lower alkoxy substituent; an amino group substituted by a lower alkyl group or a lower alkoxy group; a lower alkanoyloxy group optionally having 1 to 2 substituents selected from a lower alkoxy group, a lower alkoxycarbonyl group, amino group and phenyl group; a halogen atom; hydroxy group; carbamoyl group; a lower alkylthio group; a lower alkylsulfinyl group; a lower alkylsulfonyl group; carboxyl group; formyl group; cyano group; a di-lower alkylcarbamoyloxy group; phenoxycarbonyloxy group; a lower alkylenedioxy group; or a benzoyloxy group optionally having a lower alkoxy substituent.

Among the compounds [I-b], more preferable compounds are (1) compounds of the formula [I-c]:

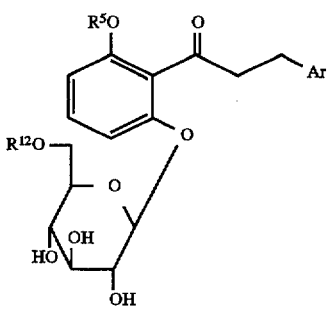

[I-c]

wherein $R^{12}$ is an acyl group, and Ar and $OR^5$ are the same defined above;

(2) compounds of the formula [I-d]:;

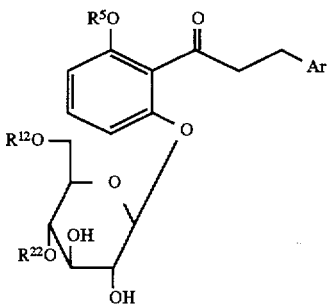

wherein $R^{22}$ is an acyl group, and Ar, $R^{12}$ and $OR^5$ are the same as defined above;

(3) compounds of the formula [I-e]:

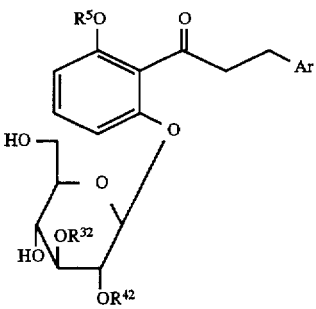

wherein $R^{32}$ and $R^{42}$ are each an acyl group, and Ar and $OR^5$ are the same as defined above;

(4) compounds of the formula [I-f]:

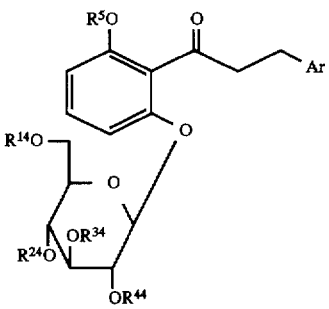

wherein $R^{14}$, $R^{24}$, $R^{34}$ and $R^{44}$ are the same or different and are each an acyl group, and Ar and $OR^5$ are the same as defined above;

(5) compounds of the formula [I-g]:

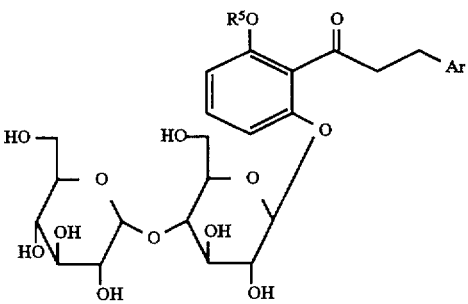

wherein Ar and $OR^5$ are the same as defined above; or (6) compounds of the formula [I-h]:

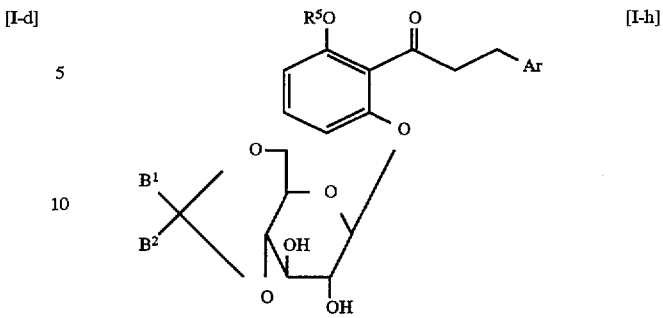

wherein $B^1$ and $B^2$ are the same or different and are each hydrogen atoms, a phenyl group, a lower alkanoyloxy group or a lower alkoxy group, or $B^1$ and $B^2$ may form a group of the formula: =O, and Ar and $OR^5$ are the same as defined above.

In the above formulae [I-c] to [I-f], the acyl group represented by $R^{11}$ to $R^{42}$, or $R^{14}$ to $R^{44}$ are the same groups as those for the acyl group represented by $R^1$ to $R^4$.

Among the compounds [I-c], further preferable compounds are compounds of the formula [I-c] wherein Ar is a phenyl group optionally substituted by a group selected from a halogen atom, hydroxy group, a lower alkyl group, a lower alkoxy group, a lower alkanoyloxy group and a lower alkoxycarbonyloxy group, the group of the formula: $OR^5$ is a protected or unprotected hydroxy group or a lower alkoxy group, and $R^{12}$ is a lower alkanoyl group optionally substituted by a group selected from a hydroxy group, a lower alkoxy group, a lower alkoxy-lower alkoxy group, carboxyl group, an alkanoylamino group, phenoxy group, phenyl group and a protected or unprotected amino group; a lower alkoxycarbonyl group optionally substituted by a group selected from a lower alkoxy group and phenyl group; benzoyl group; or phenoxycarbonyl group.

Among the compounds [I-d], further preferable compounds are compounds of the formula [I-d] wherein Ar is a phenyl group optionally substituted by a group selected from a halogen atom, hydroxy group, a lower alkyl group, a lower alkoxy group, a lower alkanoyloxy group and a lower alkoxycarbonyloxy group, the group of the formula: $OR^5$ is a protected or unprotected hydroxy group or a lower alkoxy group, and $R^{12}$ and $R^{22}$ are each a lower alkanoyl group optionally substituted by a group selected from a hydroxy group, a lower alkoxy group, a lower alkoxy-lower alkoxy group, carboxyl group, an alkanoylamino group, phenoxy group, phenyl group and a protected or unprotected amino group; a lower alkoxycarbonyl group optionally substituted by a group selected from a lower alkoxy group and phenyl group; benzoyl group; or phenoxycarbonyl group.

Among the compounds [I-e], further preferable compounds are compounds of the formula [I-e] wherein Ar is a phenyl group optionally substituted by a group selected from a halogen atom, hydroxy group, a lower alkyl group, a lower alkoxy group, a lower alkanoyloxy group and a lower alkoxycarbonyloxy group, the group of the formula: $OR^5$ is a protected or unprotected hydroxy group or a lower alkoxy group, and $R^{32}$ and $R^{42}$ are each a lower alkanoyl group optionally substituted by a group selected from a hydroxy group, a lower alkoxy group, a lower alkoxy-lower alkoxy group, carboxyl group, an alkanoylamino group, phenoxy group, phenyl group and a protected or unprotected amino group; a lower alkoxycarbonyl group optionally substituted by a group selected from a lower alkoxy group and phenyl group; benzoyl group; or phenoxycarbonyl group.

Among the compounds [I-f], further preferable compounds are compounds of the formula [I-f] wherein Ar is a phenyl group optionally substituted by a group selected from a halogen atom, hydroxy group, a lower alkyl group, a lower alkoxy group, a lower alkanoyloxy group and a lower alkoxycarbonyloxy group, the group of the formula: $OR^5$ is a protected or unprotected hydroxy group or a lower alkoxy group, and $R^{14}$, $R^{24}$, $R^{34}$ and $R^{44}$ are each a lower alkanoyl group optionally substituted by a group selected from a hydroxy group, a lower alkoxy group, a lower alkoxy-lower alkoxy group, carboxyl group, an alkanoylamino group, phenoxy group, phenyl group and a protected or unprotected amino group; a lower alkoxycarbonyl group optionally substituted by a group selected from a lower alkoxy group and phenyl group; benzoyl group; or phenoxycarbonyl group.

Among the compounds [I-g], further preferable compounds are compounds of the formula [I-g] wherein Ar is a phenyl group, a lower alkylphenyl group, a halogenophenyl group, hydroxyphenyl group or a lower alkoxyphenyl group, and the group of the formula: $OR^5$ is a protected or unprotected hydroxy group or a lower alkoxy group.

Among the compounds [I-h], further preferable compounds are compounds of the formula [I-h] wherein $B^1$ is phenyl group and $B^2$ is hydrogen atom.

Among these compounds, the pharmaceutically preferable compounds are compounds of the formula [I-a] wherein $Ar^2$ is a $C_{1-3}$ alkylphenyl group, a $C_{2-3}$ alkoxy-phenyl group, a $C_{1-6}$ alkoxy-carbonyloxy-phenyl group, or a halogenophenyl group, and the group of the formula: $OR^5$ is a protected or unprotected hydroxy group, or compounds of the formula [I-e] wherein Ar is a phenyl group optionally substituted by a group selected from a halogen atom, hydroxy group, a lower alkyl group, a lower alkoxy group, a lower alkanoyloxy group and a lower alkoxycarbonyloxy group, the group of the formula: $OR^5$ is a protected or unprotected hydroxy group, and $R^{32}$ and $R^{42}$ are each a lower alkanoyl group optionally substituted by a group selected from hydroxy group, a lower alkoxy group, a lower alkoxy-lower alkoxy group, benzyloxycarbonylamino group and amino group, a lower alkoxycarbonyl group, benzoyl group or phenoxycarbonyl group.

The pharmaceutically more preferable compounds are compounds of the formula [I-e] wherein Ar is a phenyl group optionally substituted by a group selected from a lower alkyl group and a lower alkoxy group, the group of the formula: $OR^5$ is hydroxy group or a hydroxy group protected by a lower alkanoyl group, and $R^{32}$ and $R^{42}$ are each a lower alkanoyl group, a lower alkoxy-substituted lower alkanoyl group, an amino-substituted lower alkanoyl group, a lower alkoxycarbonyl group or phenoxycarbonyl group, and especially the compounds of the formula [I-e] wherein Ar is a lower alkoxy-substituted phenyl group, and $R^{32}$ and $R^{42}$ are each a lower alkoxy-substituted lower alkanoyl group are preferable.

The active ingredient [I] of the present invention may be used in the form of a pharmaceutically acceptable salt thereof in clinical use. The pharmaceutically acceptable salt is a salt with an inorganic acid (e.g. hydrochloric acid, sulfuric acid, etc.) or with an organic acid (e.g. acetic acid, methanesulfonic acid, etc.), or a salt with an inorganic base (e.g. sodium, potassium, etc.) or with an organic base (e.g. ammonia, a lower alkylamine, etc.).

The active ingredients [I] of the present invention and pharmaceutically acceptable salts thereof may be administered either orally or parenterally, and or in the form of a pharmaceutical preparation in admixture with an excipient suitable for oral administration or parenteral administration. The pharmaceutical preparation are solid preparations such as tablets, capsules, powders, etc., or liquid preparations such as solutions, suspensions, emulsions, etc. When the active ingredient [I] is administered parenterally, an injection form is preferable.

The dosage of the active ingredient [I] of the present invention varies according to ages, weights and conditions of patients, or severity of diseases to be cured, but it is usually in the range of 1 to 100 mg/kg/day, preferably in the range of 5 to 40 mg/kg/day in case of oral administration. In case of parenteral administration, the dosage of the active ingredient [I] of the present invention is in the range of 0.1 to 50 mg/kg/day, preferably in the range of 0.5 to 10 mg/kg/day.

The compounds of the formula [I-A] may be prepared by subjecting a chalcone derivative of the formula [II]:

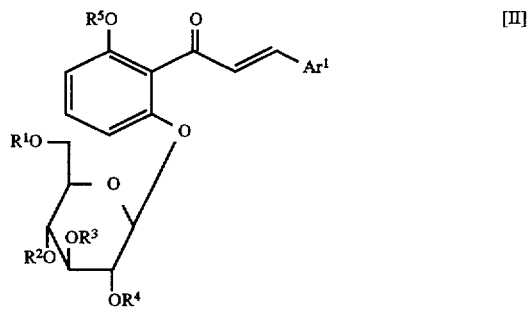

wherein $Ar^1$, $R^1$, $R^2$, $R^3$, $R^4$ and $OR^5$ are the same as defined above, to reduction reaction, followed by removing the protecting group, if necessary.

The reduction reaction may be carried out by a conventional method, for example, by reduction using a metal hydride, or by catalytic hydrogenation.

The reduction with a metal hydride is carried out by using a metal hydride in a solvent, and the catalytic hydrogenation is carried out, for example, by using a catalyst under atmospheric pressure under hydrogen gas.

In the catalytic hydrogenation, the catalyst may be any conventional ones, for example, palladium-carbon, platinum oxide, and the like.

In the reduction using a metal hydride, the metal hydride may be any conventional one which can reduce the double bond, especially one which can reduce the double bond but not the ketone group, for example, sodium hydrogen telluride. Sodium hydrogen telluride may be prepared according to the method disclosed in Synthesis, p. 545 (1978), and usually used in an amount of 1 to 3 equivalents, preferably in an amount of 1 to 1.5 equivalent, to 1 equivalent of the chalcone derivative.

The solvent may be any inert solvents which does not affect the reaction, for example, organic solvents (e.g. methanol, ethanol, tetrahydrofuran, ethyl acetate, acetic acid, etc.), or a mixture of water and these solvents.

The reaction may be carried out at a temperature of from under cooling or to with heating, preferably at a temperature from 10° C. to 30° C.

Among the active compounds [I-A], the following compounds are prepared as follows:

(1) The compound of the formula [I-c] may be prepared by acylating the 6-hydroxy group of the glucopyranosyl group of a compound of the formula [I-i]:

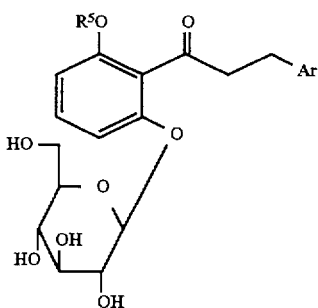

[I-i]

wherein Ar and OR⁵ are the same as defined above.

Additionally, it is noted that compounds encompassed by the above generic Formula [I-i] (as well as compounds encompassed by Formula [I-a]) are useful as intermediates when preparing compounds of Formula [I], wherein one or more of the $R^1$–$R^4$ substituents thereof are other than hydrogen. For example, compounds of Formula [I-a] may be used to prepare compounds of Formula [I] wherein one or more of the $R^1$–$R^4$ substituents thereof are acyl, by acylating said one or more $R^1$–$R^4$ hydrogen substituents. Furthermore, protection of certain of the $R^1$–$R^4$ substituents on the Formula [I] compounds prior to said acylation, and a subsequent deprotection of said protected groups can be utilized as a method of preparing compounds of Formula [I] wherein one or more of the substituents $R^1$–$R^4$ in Formula [I] is hydrogen and one or more of said substituents is acyl.

(2) The compound of the formula [I-d] may be prepared by acylating the 4- and 6-hydroxy groups of the glucopyranosyl group of the compound of the formula [I-j]:

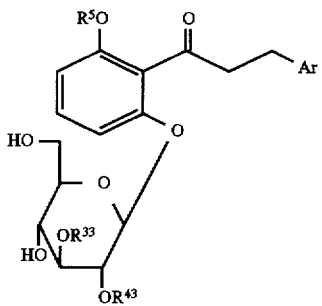

[I-j]

wherein $R^{33}$ and $R^{43}$ are both a protecting group for hydroxy group, and Ar and OR⁵ are the same as defined above, followed by removing the protecting groups.

(3) The compound of the formula [I-e] may be prepared by acylating the 2- and 3-hydroxy groups of the glucopyranosyl group of the compound of the formula [I-k]:

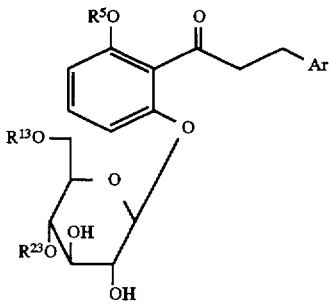

[I-k]

wherein $R^{13}$ and $R^{23}$ are both a protecting group for hydroxy group, and Ar and OR⁵ are the same as defined above, followed by removing the protecting groups.

(4) The compound of the formula [I-f] may be prepared by acylating the hydroxy group of the glucopyranosyl group of the compound of the formula [I-l]:

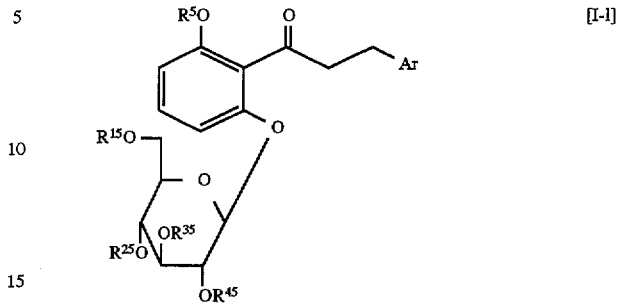

[I-l]

wherein at least one of $R^{15}$, $R^{25}$, $R^{35}$ and $R^{45}$ is hydrogen atom and the other groups are an acyl group, and Ar and OR⁵ are the same as defined above.

In the acylation reactions of the above (2) and (3), the protecting group for hydroxy group in the compound [I-j] and the compound [I-k] may be any conventional ones which can be a protecting group for hydroxy group, for example, in addition the protecting groups for the group of the formula: OR⁵, benzyloxy group, a lower alkanoyl group, a lower alkoxycarbonyl group, and the like, or $R^{13}$ and $R^{23}$ may combine together to form benzylidene group, a lower alkoxy-substituted methylene group or a di-lower alkoxy-substituted methylene group.

In the acylation reactions in the above (1), (2), (3) and (4), when the group of the formula: OR⁵ in the starting compounds is a free hydroxy group, or Ar in the starting compounds is hydroxyphenyl group, these groups may also be acylated during the these acylation reactions, but the products thus obtained are also included in the desired compounds of the present invention.

The acylation of the starting compound is carried out by reacting the starting compound with an organic acid corresponding to the desired acyl group, or a salt thereof, or a reactive derivative thereof. The reaction with an acid compound corresponding to the desired acyl group may be carried out in the presence or absence of a condensing agent, and the reaction of the starting compound with a reactive derivative of the said compound is carried out in the presence or absence of an acid acceptor, in a solvent, respectively.

The salt of the organic acid includes, for example, an alkali metal salt and an alkaline earth metal salt such as sodium salt, potassium salt, calcium salt, and the like. The reactive derivative includes a halide, anhydride, an active ester of a corresponding acid.

The acid acceptor includes, for example, an inorganic base (e.g. an alkali metal hydroxide, an alkali metal carbonate, an alkali metal hydrogen carbonate, an alkali metal hydride, etc.) or an organic base (e.g. a tri-lower alkylamine, pyridine, 4-dimethylaminopyridine, etc.).

The condensing agent includes, for example, conventional ones such as phosphorus oxychloride, N,N'-carbonyldiimidazole, diethyl cyanophosphate, dicyclohexylcarbodiimide, and the like.

The solvent may be any conventional ones which do not affect disadvantageously the reaction, for example, dichloromethane, dimethylformamide, tetrahydrofuran, and the like.

The reaction is carried out under cooling or with heating, preferably at a temperature from −10° C. to 100° C., more preferably at a temperature from 0° C. to 50° C.

In the above reaction, the degree of the acylation, i.e. the acylation of all hydroxy groups or selective acylation of some hydroxy groups, may be selected by controlling the difference of stereo-structural circumstance around the hydroxy group of the starting compound, or the amount of the acid compound, a salt thereof or a reactive derivative thereof. Therefore, both the compound [I-c] and the compound [I-f] may be selectively and freely prepared from the same starting compound [I-i].

In addition, in the obtained products, when $R^{12}$ to $R^{42}$ or $R^{14}$ to $R^{44}$ are an acyl group having a protected amino group, or the group of the formula: $OR^5$ is a protected hydroxy group, these protecting groups may be removed, if necessary. The removal of these protecting groups may be carried by a conventional method such as hydrolysis, reduction, acid-treatment, etc., according to the types of the protecting groups to be removed.

Among the active compounds [I-A], the dihydrochalcone derivative of the formula [I-h] may be prepared by reacting the compound of the formula [I-i] and a compound of the formula [III-a]:

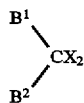  [III-a]

wherein X is a reactive residue, and $B^1$ and $B^2$ are the same as defined above, or a compound of the formula [III-b]:

  [III-b]

wherein $B^1$ is the same as defined above.

The reaction of the compound [I-i] and the compound [III-a] or the compound [III-b] may be carried out in the presence of an acid catalyst, or in the presence of an acid acceptor, in a solvent. The acid catalyst includes, for example, Lewis acids (e.g. zinc chloride, etc.), mineral acids (e.g. hydrochloric acid, sulfuric acid, nitric acid, etc.), or organic acids (e.g. p-toluenesulfonic acid, methanesulfonic acid, etc.). The acid-acceptor includes, for example, inorganic bases (e.g. an alkali metal hydroxide, an alkali metal carbonate, an alkali metal hydrogen carbonate, an alkali metal hydride, etc.), or a tri-lower alkylamine, pyridine, 4-dimethylaminopyridine, and the like. The reaction is carried out under cooling or with heating, preferably at a temperature from 10° C. to 40° C.

The solvent used in the above reactions may be any conventional ones which do not disadvantageously affect the reactions.

The starting compound of the formula [II] may be prepared by condensing an acetophenone derivative of the formula [IV]:

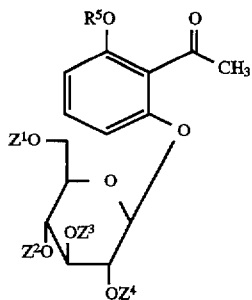  [IV]

wherein $Z^1$, $Z^3$ and $Z^4$ are a protected or unprotected hydroxy group, $Z^2$ is a protected or unprotected hydroxy group or α-D-glucopyranosyl group in which the hydroxy groups are protected, and $OR^5$ is the same as defined above, with an aldehyde compound of the formula [V]:

  [V]

wherein $Ar^1$ is the same as defined above, followed by removing the protecting groups, if necessary, further by acylating the hydroxy group of the product, or by reacting the product with the compound [III-a], or by reacting the product with the compound [III-b], if necessary.

The condensation reaction of the compound [IV] and the compound [V] may be carried out by a conventional method, for example, in the presence of a base (e.g. an alkali metal hydroxide, etc.) in a solvent (e.g. organic solvents such as methanol, ethanol, etc., or a mixture of water and these organic solvents) under cooling or with heating, preferably at a temperature from 10° C. to 30° C.

In the starting compounds [IV], the "protected hydroxy group" includes hydroxy groups protected by a conventional protecting group such as a lower alkanoyl group, a substituted or unsubstituted phenyl-lower alkyl group, a tri-lower alkylsilyl group, etc. The removal of these protecting groups may be carried out by a conventional method such as hydrolysis, reduction, acid-treatment, etc., which should be selected according to the types of the protecting groups to be removed. When said protecting group is a lower alkanoyl group such as acetyl group, the removal thereof may be advantageously carried out simultaneously with the condensation reaction in one step by using an alkali metal hydroxide.

Besides, in the condensation reaction for preparation of the compound [II], when hydroxybenzaldehyde is used as an aldehyde compound, the yield of the product is improved by the use of hydroxybenzaldehyde having phenolic hydroxy group protected.

In the above condensation reaction, the protecting group for phenolic hydroxy group of the aldehyde compound [V] may be any conventional ones which are easily removed by a conventional method such as hydrolysis, reduction, acid-treatment, and the like. More particularly, when the groups which are removed by reduction, i.e. substituted or unsubstituted phenyl-lower alkyl groups (e.g. benzyl group, etc.) are used as a protecting group, the removal of these protecting groups is advantageously carried out simultaneously with the reduction reaction of the chalcone derivative [II].

When the product is acylated after the condensation reaction, the acylation reaction may be carried out in the same procedures as in the reactions preparing the compounds [I-c] to [I-f]. When the product obtained by the condensation reaction and the compound [III-a] or the compound [III-b] are reacted, the reaction is carried out in the same procedures as the reaction preparing the compound [I-h].

The chalcone derivative [II] thus obtained may be used in the subsequent reduction reaction after purification, but used without further purification.

The compound of the formula [I-j] may be prepared, for example, by protecting the 2- and 3-hydroxy groups of the glucopyranosyl group of the compound [I-h] in which $B^1$ is phenyl group and $B^2$ is hydrogen atom, followed by removing substituents of the 4- and 6-hydroxy groups of the glucopyranosyl group.

The compound of the formula [I-k] may be prepared, for example, by protecting the 4 and 6-hydroxy groups of the glucopyranosyl group of the compound [I-j], followed by removing the protecting groups for the 2- and 3-hydroxy groups of the glucopyranosyl group.

In the above reactions, the protecting for the hydroxy groups of the glucopyranosyl group may be any ones which can be easily removed by a conventional method such as hydrolysis, reduction, acid-treatment, and the like.

The starting compound [IV] wherein $Z^1$ to $Z^4$ are acetyl group, may be prepared according to the method disclosed in Journal of Medicinal and Pharmaceutical Chemistry, Vol. 5, p. 1054 (1962), for example, by reacting 2',6'-dihydroxyacetophenone and 2,3,4,6-tetra-O-acetyl-α-D-glucopyranosyl bromide in the presence of potassium hydroxide in an aqueous acetone.

The starting compound [IV] wherein $Z^1$, $Z^3$ and $Z^4$ are acetyl group, and $Z^2$ is α-D-glucopyranosyl group in which the hydroxy group is protected by acetyl group may be prepared by refluxing 2',6'-dihydroxyacetophenone and 2,3, 6-tri-O-acetyl-4-O-(2,3,4,6-tetra-O-acetyl-α-D-glucopyranosyl)-α-D-glucopyranosyl bromide in the presence of cadmium carbonate in toluene.

Among the active compounds [I], the compound of the formula [I] wherein Ar is 4-hydroxyphenyl group, 4-methoxyphenyl group or phenyl group, $R^1$, $R^2$, $R^3$ and $R^4$ are all hydrogen atom, and the group of the formula: $OR^5$ is hydroxy group may be prepared according to the method disclosed in Biochemistry, Vol. 8, p. 2067 (1969).

Throughout the present specification, the "lower alkyl group", the "lower alkoxy group" and the "lower alkylene group" mean ones having 1 to 6 carbon atoms, respectively, and the "lower alkanoyl group" means ones having 2 to 7 carbon atoms, and "2'-O-(β-D-glucopyranosyl)" means "2-(β-D-glucopyranosyl)oxy".

Effects
[Pharmacological experiments]
Experiment 1: Hypoglycemic activity in mice (1)
Method After an overnight fast, a test compound (100 mg/kg) was orally administered to male diabetic KK mice (6 mice/group, 15 wk old), and immediately, glucose in isotonic saline (2 g/5 ml/kg) was subcutaneously administered to the mice. Blood was collected from tail tip without anesthesia after a fixed time, and the blood glucose concentration was measured by glucose.oxidase method. In the control group, the same procedures were repeated except a solvent was administered instead of a test compound.

The results are shown in Table 1.
Test compound
2'-O-(β-D-glucopyranosyl)-6'-hydroxy-4-methoxydihydrochalcone [i.e. 2'-(β-D-glucopyranosyl)oxy-6'-hydroxy-4-methoxydihydrochalcone]

TABLE 1

| | Blood glucose (mg/dl)* | |
|---|---|---|
| Time (hr) | Tested group | Control |
| 0 (before administration) | 255 ± 17 | 254 ± 18 |
| 0.5 | 344 ± 18 | 535 ± 23 |
| 1 | 359 ± 15 | 612 ± 5 |
| 2 | 333 ± 17 | 520 ± 17 |

(*: average ± standard deviation)

As is shown in the above results, the blood glucose concentration is significantly decreased in the tested group as compared with that of the control group.

Experiment 2: Hypoglycemic activity in mice (2)
Method

After an overnight fast, a test compound (100 mg/kg) was orally administered to male ddY-mice (6 mice/group, 8 wk old), and immediately, glucose in isotonic saline (1 g/5 ml/kg) was subcutaneously administered to the mice. After a fixed time therefrom, blood was collected from tail tip without anesthesia, and the blood glucose concentration therein was measured by glucose.oxidase method. In the control group, glucose was administered subcutaneously to the mice without a test compound.

The results are shown in Table 2.

Test compound

2'-O-(2,3-di-O-acetyl-β-D-glucopyranosyl)-6'-hydroxy-4-methoxyldihydrochalcone

TABLE 2

| | Blood glucose (mg/dl)* | |
|---|---|---|
| Time (hr) | Tested group | Control |
| 0 (before administration) | 80 ± 3 | 85 ± 5 |
| 0.5 | 139 ± 4 | 201 ± 14 |
| 1 | 117 ± 9 | 158 ± 16 |
| 2 | 87 ± 7 | 94 ± 9 |

(*: average ± standard deviation)

As is shown in the above results, the blood glucose concentration in the tested group was significantly decreased as compared with that of the control group.

Experiment 3: Urine glucose increasing activity in rats
Method

A test compound solution (100 mg/5 ml/kg) was orally administered twice at 8-hr intervals to male SD-rats (3 to 5 rats/group, 6 wk old). The test compound solution was prepared by adding Tween 80 to a test compound, which was suspended into purified water. In the control group, purified water containing only Tween 80 was administered instead of the test compound solution. Rats were housed individually into a metabolite cage, and urine was collected for 24 hours after the first administration of the test compound. After measuring the urine volume, the urine was centrifuged in order to remove the impurity, and the urine glucose concentration therein was determined by glucose.analyzer (Appek Co. Ltd.). The amount of the urine glucose (mg) excreted for 24 hours was determined according to the urine volume (ml) and the urine glucose concentration therein (mg/ml). The amount of urine glucose excreted for 24 hours was in the range of 0 to 6 mg in the control group, and that of the phlorizin treated group was 11±6 mg.

The results are shown in Table 3.

TABLE 3

[Structure: benzene ring with R⁵O and C(=O)CH₂CH₂-Ar substituents, connected via O to a sugar (pyranose) ring bearing R¹O-CH₂, OR³, R²O, OR⁴ groups]

| Test Compound | | | | | Urine glucose |
|---|---|---|---|---|---|
| Ar | R¹ | R² | R³, R⁴ | R⁵ | (mg/24 hr) |
| 4-CH₃-C₆H₄- | H | H | H | H | 344 ± 84 |
| 4-CH₂CH₃-C₆H₄- | H | H | H | H | 277 ± 64 |
| 3-CH₃-C₆H₄- | H | H | H | H | 299 ± 35 |
| 4-OCH₃-C₆H₄- | H | H | H | H | 380 ± 52 |
| 4-OCH₂CH₃-C₆H₄- | H | H | H | H | 124 ± 27 |
| 4-OH-C₆H₄- | H | H | H | H | 60 ± 9 |
| 4-Cl-C₆H₄- | H | H | H | H | 253 ± 23 |
| C₆H₅- | H | H | H | H | 217 ± 18 |
| 4-CF₃-C₆H₄- | H | H | H | H | 114 ± 21 |
| 4-N(CH₃)₂-C₆H₄- | H | H | H | H | 178 ± 22 |

TABLE 3-continued
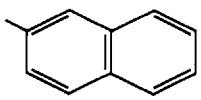
| Test Compound | | | | | Urine glucose |
|---|---|---|---|---|---|
| Ar | R¹ | R² | R³, R⁴ | R⁵ | (mg/24 hr) |
| 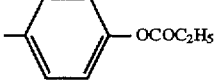 | H | H | H | H | 224 ± 36 |
| 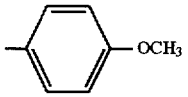 —OCOC₂H₅ | H | H | H | H | 165 ± 12 |
| 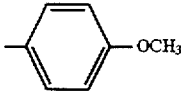 —OCH₃ | H | H | CH₃CO | CH₃CO | 352 ± 62 |
| 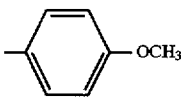 —OCH₃ | H | H | CH₃CO | H | 421 ± 45 |
| 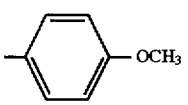 —OCH₃ | H | H | CH₃OCH₂CO | H | 446 ± 54 |
| 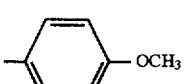 —OCH₃ | H | H | CH₃CH₂O-CH₂CO | H | 417 ± 17 |
| 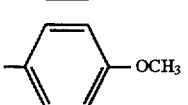 —OCH₃ | H | H | CH₃CH₂OCO | H | 255 ± 36 |
| 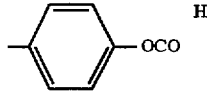 —OCH₃ | H | H | 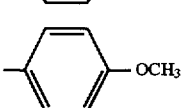—OCO | H | 195 ± 41 |
| 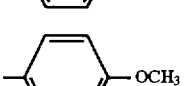 —OCH₃ | H | H | CH₃SO₃H.NH₂-CH₂CO | H | 194 ± 35 |
| 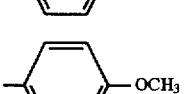 —OCH₃ | H | H | (CH₃)₂CH-CH₂OCH₂CO | H | 218 ± 33 |
| —OCH₃ | H | H | CH₃O(CH₂)₂-CO | H | 213 ± 31 |

TABLE 3-continued

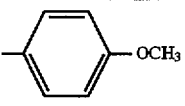

| Test Compound | | | | | Urine glucose |
|---|---|---|---|---|---|
| Ar | $R^1$ | $R^2$ | $R^3, R^4$ | $R^5$ | (mg/24 hr) |
| 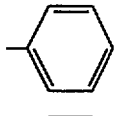 | H | H | $CH_3O(CH_3)$-CHCO | H | 282 ± 46 |
| 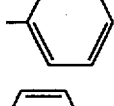 | H | H | $CH_3CO$ | H | 265 ± 126 |
| 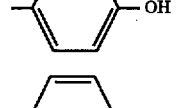 | H | H | $CH_3OCH_2CO$ | H | 251 ± 16 |
| 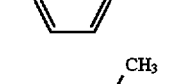 | H | H | $CH_3OCH_2CO$ | H | 122 ± 49 |
| 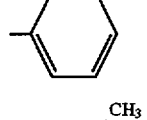 | H | H | $CH_3OCH_2CO$ | H | 289 ± 83 |
| 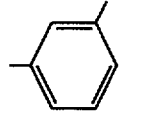 | H | H | $CH_3CO$ | H | 172 ± 22 |
| 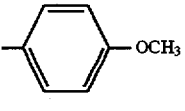 | H | H | $CH_3CH_2O$-$CH_2CO$ | H | 352 ± 88 |
| 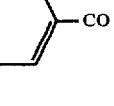 | 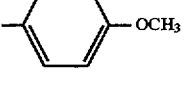 | H | H | H | 214 ± 44 |
| 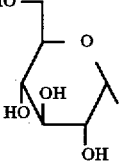 | H | (sugar group) | H | H | 157 ± 15 |

As is shown in the above results, the active dihydrochalcone derivatives [I] of the present invention show about 5 to 40 times as strong urine glucose increasing activity as phlorizin does.

EXAMPLES

The present invention is illustrated in more detail by the following Examples and Reference Examples, but should not be construed to be limited thereto.

Example 1

(1) To a mixture of 2'-O-(2,3,4,6-tetra-O-acetyl-β-D-glucopyranosyl)-6'-hydroxyacetophenone [i.e. 2'-(2,3,4,6-tetra-O-acetyl-β-D-glucopyranosyl)oxy-6'-hydroxyacetophenone] (1000 mg), p-tolualdehyde (373 mg) and ethanol (10 ml) is added dropwise a 50% aqueous potassium hydroxide solution (2 ml), and the mixture is stirred at room temperature overnight. The mixture is evaporated under reduced pressure to remove the solvent, and to the residue are added water and diethyl ether. The mixture is stirred and the aqueous layer is collected. The aqueous layer is neutralized with a 10% hydrochloric acid under ice-cooling, and extracted with ethyl acetate. The extract is washed with water, dried, and evaporated to remove the solvent to give crude 2'-O-(β-D-glucopyranosyl)-6'-hydroxy-4-methylchalcone (670 mg).

FABMS (m/z): 417 (MH$^+$)

(2) The above crude 2'-O-(β-D-glucopyranosyl)-6'-hydroxy-4-methylchalcone (665 mg) is dissolved in ethanol (20 ml), and the mixture is subjected to catalytic hydrogenation under atmospheric pressure by using 10% palladium-carbon (0.5 g). The catalyst is removed by filtration, and the filtrate is concentrated under reduced pressure. The residue is purified by silica gel column chromatography to give 2'-O-(β-D-glucopyranosyl)-6'-hydroxy-4-methyldihydrochalcone (470 mg).

M.p. 109°–111° C.

NMR (DMSO-d$_6$) δ: 2.25 (3H, s), 2.85 (2H, t, J=7.6 Hz), 3.0–3.4 (6H, m), 3.45 (1H, m), 3.70 (1H, dd, J=5.4, 10.3 Hz), 4.53 (1H, t, J=5.6 Hz), 4.91 (1H, d, J=7.3 Hz), 5.01 (1H, d, J=4.9 Hz), 5.07 (1H, d, J=4.4 Hz), 5.19 (1H, d, J=4.9 Hz), 6.55 (1H, d, J=7.8 Hz), 6.68 (1H, d, J=8.3 Hz), 7.05 (2H, d, J=7.8 Hz), 7.14 (2H, d, J=7.8 Hz), 7.24 (1H, t, J=8.3 Hz), 11.01 (1H, brs)

IR (nujol) cm$^{-1}$: 3440, 3320, 1620

FABMS (m/z): 441 [(M+Na)$^+$]

Examples 2–30

Using the corresponding starting compounds, the compounds listed in Table 4 are obtained in the same manner as in Example 1.

TABLE 4

(R: β-D-glucopyranosyl group)

| Ex. No. | Ar | Physical properties |
|---|---|---|
| 2 | CH$_2$CH$_3$ (para) | M.p. 127–129.5° C.<br>NMR(DMSO-d$_6$) δ: 1.15(3H, t, J=7.8Hz), 2.5–2.6 (2H, m), 2.86(2H, t, J=7.3Hz), 3.1–3.4(6H, m), 3.47 (1H, dd, J=5.4, 11.5Hz), 3.70(1H, dd, J=5.4, 10.3 Hz), 4.56(1H, t, J=11.7Hz), 4.91(1 H, d, J=7.3Hz), 5.03(1H, d, J=4.9Hz), 5.10(1H, d, J=4.4Hz), 5.23 (1H, d, J=5.4Hz), 6.55(1H, d, J=7.8Hz), 6.67(1H, d, J=8.3Hz), 7.08(2H, d, J=8.3Hz), 7.16(2H, d, J=8.3Hz), 7.24(1H, t, J=8.3Hz), 10.99(1H, br)<br>IR(nujoi) cm$^{-1}$: 3600–3200, 1620, 1600, 1460, 1380, 1230<br>FABMS (m/z): 455 [(M + Na)$^+$] |
| 3 | CH$_3$ (meta) | M.p. 78–81° C.<br>NMR(DMSO-d$_6$) δ: 2.27(3H, s), 2.86(2H, t, J=7.4 Hz), 3.14–3.28(6H, m), 3.45(1H, dd, J=5.9, 11.8 Hz), 3.70(1H, dd, J=5.2, 10.3Hz), 4.57(1H, t, J=5.6 Hz), 4.91(1H, d, J=7.5Hz), 5.04(1H, d, J=5.2Hz), 5.11(1H, d, J=4.7Hz), 5.23(1H, d, J=5.2Hz), 6.55 (1H, d, J=8.1Hz), 6.68(1H, d, J=8.5Hz), 6.97(1H, d, J=7.6Hz), 7.04(1H, d, J=7.9Hz), 7.07(1H, s), 7.14(1H, t, J=7.5Hz), 7.24(1H, t, J=8.3Hz), 10.99 (1H, s)<br>IR(nujol) cm$^{-1}$: 3600–3200, 1620, 1600, 1460, 1220<br>FABMS (m/z): 441 [(M + Na)$^+$] |

TABLE 4-continued

[Structure: 2'-hydroxy-6'-(β-D-glucopyranosyloxy)phenyl propyl-Ar ketone]

(R: β-D-glucopyranosyl group)

| Ex. No. | Ar | Physical properties |
|---|---|---|
| 4 | 4-OCH₂CH₃-phenyl | M.p. 76.5–78° C.<br>NMR(DMSO-d₆) δ: 1.30(3H, t, J=7.1Hz), 2.83(2H, t, J=7.3Hz), 3.1–3.4(6H, m), 3.47(1H, m), 3.70(1H, dd, J=5.4, 10.3Hz), 3.97(2H, q, J=7.1Hz), 4.56(1H, t, J=5.6Hz), 4.91(1H, d, J=7.3Hz), 5.03(1H, d, J=4.9Hz), 5.10(1H, d, J=4.4Hz), 5.23(1H, d, J=4.9 Hz), 6.55(1H, d, J=8.3Hz), 6.67(1H, d, J=8.3Hz), 6.80(2H, d, J=8.8Hz), 7.15(2H, d, J=8.3Hz), 7.24 (1H, t, J=8.3Hz), 10.99(1H, s)<br>IR(nujol) cm⁻¹: 3560, 3500, 3440, 3340, 1630<br>FABMS (m/z): 471 [(M + Na)⁺] |
| 5 | 4-OCH(CH₃)₂-phenyl | M.p. 82–85° C.<br>NMR(DMSO-d₆) δ: 1.23(6H, t, J=5.9Hz), 2.82(2H, t, J=7.6Hz), 3.1–3.4(6H, m), 3.46(1H, m), 3.70(1H, dd, J=5.4, 10.3Hz), 4.52(1H, q, J=5.9Hz), 4.56(1H, t, J=5.9Hz), 4.91(1H, d, J=7.3Hz), 5.03(1H, d, J=4.9Hz), 5.10(1H, d, J=4.4Hz), 5.23(1H, d, J=5.4 Hz), 6.55(1H, d, J=8.3Hz), 6.67(1H, d, J=8.3Hz), 6.78(2H, ddd, J=2.0, 2.9, 8.8Hz), 7.14(2H, dd, J=2.7, 8.8Hz), 7.24(1H, t, J=8.3Hz), 10.98(1H, s)<br>IR(nujol) cm⁻¹: 3400, 1630<br>FABMS (m/z): 485 [(M + Na)⁺] |
| 6 | 4-OCH₂OCH₂CH₃-phenyl | Foam<br>NMR(DMSO-d₆) δ: 1.12(3H, t, J=7.1Hz), 2.84(2H, t, J=7.3Hz), 3.0–3.4(6H, m), 3.45(1H, m), 3.63(2H, q, J=7.1Hz), 3.65(1H, m), 4.56(1H, t, J=5.6Hz), 4.91(1H, d, J=7.3Hz), 5.03(1H, d, J=4.9Hz), 5.10 (1H, d, J=4.4Hz), 5.17(2H, s), 5.24(1H, d, J=4.9 Hz), 6.55(1H, d, J=8.3Hz), 6.67(1H, d, J=8.3Hz), 6.90(2H, ddd, J=2.0, 2.4, 8.8Hz), 7.17(2H, d, J=8.8 Hz), 7.24(1H, t, J=8.3Hz), 10.98(1H, s)<br>IR(nujol) cm⁻¹: 3400, 1630<br>FABMS (m/z): 501 [(M + Na)⁺] |
| 7 | 3-OCH₃-phenyl | M.p. 105–107° C.<br>NMR(DMSO-d₆) δ: 2.88(2H, t, J=7.3Hz), 3.2–3.6 (6H, m), 3.47(1H, dd, J=5.9, 11.5Hz), 3.6–3.8(4H, m), 4.56(1H, t, J=5.9Hz), 4.91(1H, d, J=6.8Hz), 5.03(1H, d, J=5.4Hz), 5.10(1H, d, J=4.4Hz), 5.23 (1H, d, J=4.9Hz), 6.55(1H, d, J=7.8Hz), 6.68(1H, d, J=8.3Hz), 6.7–6.8(3H, m), 7.1–7.3(2H, m), 11.00 (1H, s)<br>IR(nujol) cm⁻¹: 3600–3000, 1630, 1600, 1260, 1220<br>FABMS (m/z): 457 [(M + Na)⁺] |
| 8* | 4-Cl-phenyl | M.p. 142–144° C.<br>NMR(DMSO-d₆) δ: 2.90(2H, t, J=7.3Hz), 3.1–3.4 (6H, m), 3.45(1H, m), 3.70(1H, dd, J=4.9, 11.2Hz), 4.57(1H, t, J=5.4Hz), 4.91(1H, d, J=6.8Hz), 5.04 (1H, d, J=3.9Hz), 5.11(1H, bro), 5.26(1H, d, J=4.4 Hz), 6.55(1H, d, J=8.3Hz), 6.68(1H, d, J=8.3Hz), 7.24(1H, t, J=8.3Hz), 7.30(4H, s), 10.95(1H, bro)<br>IR(nujol) cm⁻¹: 3400, 1630<br>FABMS (m/z): 463, 461 [(M + Na)⁺] |

TABLE 4-continued

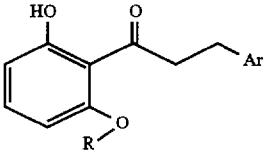

(R: β-D-glucopyranosyl group)

| Ex. No. | Ar | Physical properties |
|---|---|---|
| 9 |  | M.p. 156–158° C.<br>NMR(DMSO-d$_6$) δ: 2.91(2H, t, J=7.3Hz), 3.1–3.4 (6H, m), 3.44(1H, dd, J=5.9, 11.2Hz), 3.70(1H, dd, J=5.4, 9.8Hz), 4.56(1H, t, J=5.9Hz), 4.91(1H, d, J=7.3Hz), 5.03(1H, d, J=4.9Hz), 5.10(1H, d, J=4.4 Hz), 5.24(1H, d, J=5.4Hz), 6.54(1H, d, J=7.8Hz), 6.67(1H, d, J=8.3Hz), 7.0–7.1(2H, m), 7.2–7.3(3H, m), 10.94(1H, s)<br>IR(nujol) cm$^{-1}$: 3600–3200, 1620, 1600, 1460, 1240, 1220<br>FABMS (m/z): 445 [(M + Na)$^+$], 423(MH$^+$) |
| 10 | 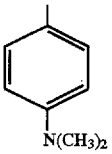 | M.p. 171–173° C.<br>NMR(DMSO-d$_6$) δ: 3.00(2H, t, J=7.3Hz), 3.10–3.60(7H, m), 3.70(1H, dd, J=5.4, 10.26Hz), 4.57 (1H, t, J=5.9Hz), 4.91(1H, d, J=7.3Hz), 5.04(1H, d, J=4.9Hz) 5.11(1H, d, J=4.4Hz), 5.28(1H, d, J=5.4 Hz)3 6.55(1H, d, J=7.8Hz), 6.68(1H, d, J=8.3Hz), 7.24(1H, dd, J=7.8, 8.3Hz), 7.50, 7.61(2H, each d, J=8.3Hz), 10.92(1H, s)<br>IR(nujol) cm$^{-1}$: 1620<br>FABMS (m/z): 495 [(M + Na)$^+$] |
| 11 | 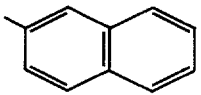 | M.p. 71° C. (gradually melting)<br>NMR(DMSO-d$_6$) δ: 2.75–2.85(2H, m), 2.83(6H, s), 3.47(1H, dd, J=5.8, 11.8Hz), 3.70(1H, dd, J=5.4, 10.3Hz), 4.56(1H, t, J=5.9Hz), 4.91(1H, d, J=7.3 Hz), 5.03(1H, d, J=5.4Hz), 5.10(1H, d, J=4.4Hz), 5.21(1H, d, J=4.9Hz), 6.56–6.69(4H, m), 7.14(2H, d, J=8.3Hz), 7.24(1H, t, J=8.3Hz), 11.03(1H, s)<br>IR(nujol) cm$^{-1}$: 3600–3200, 1620, 1600, 1520, 1460, 1230<br>FABMS (m/z): 448 [(M + Na)$^+$] |
| 12 | 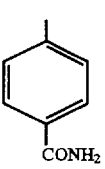 | M.p. 97–100° C.<br>NMR(DMSO-d$_6$) δ: 3.08(2H, t, J=7.3Hz), 3.1–3.4 (7H, m), 3.71(1H, dd, J=6.4, 10.8Hz), 4.58(1H, t, J=5.4Hz), 4.94(1H, d, J=7.3Hz), 5.04(1H,d, J=4.9 Hz), 5.11(1H, d, J=4.4Hz), 5.29(1H, d, J=5.4Hz), 6.56(1H, d, J=8.3Hz), 6.64(1H, d, J=8.3Hz), 7.25 (1H, t, J=8.3Hz), 7.38–7.48(3H, m), 7.76–7.88(4H, m), 11.01(1H, s)<br>IR(nujol) cm$^{-1}$: 3600–3200, 1630, 1600, 1460, 1230<br>FABMS (m/z): 477 [(M + Na)$^+$] |
| 13 | 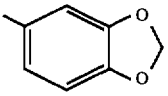 | M.p. 178–181° C.<br>IR(nujol) cm$^{-1}$: 3430, 3390, 3330, 1640, 1625, 1610<br>FABMS (m/z): 470 [(M + Na)$^+$] |
| 14 | 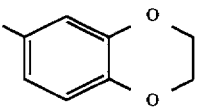 | M.p. 168.5–170° C.<br>IR(nujol) cm$^{-1}$: 3550, 3520, 3440, 3380, 1620<br>FABMS (m/z): 471 [(M + Na)$^+$] |
| 15 |  | M.p. 86° C. ~ (gradually melting)<br>IR(nujol) cm$^{-1}$: 3400, 1630<br>FABMS (m/z): 485 [(M + Na)$^+$] |

TABLE 4-continued

Structure: 2-hydroxy-6-(β-D-glucopyranosyloxy)phenyl ketone with -CH₂CH₂-Ar side chain (R: β-D-glucopyranosyl group)

| Ex. No. | Ar | Physical properties |
|---|---|---|
| 16 | 2-pyrrolyl | M.p. 154–156° C.<br>IR(nujol) cm$^{-1}$: 3560, 3440, 3400, 1620, 1600<br>FABMS (m/z): 417 [(M + Na)$^+$] |
| 17 | 2-furyl | M.p. 65° C. (gradually melting)<br>IR(nujol) cm$^{-1}$: 3600–3000, 1630, 1600, 1230<br>FABMS (m/z): 417 [(M + Na)$^+$] |
| 18 | 3,4-dimethoxyphenyl | M.p. 176–178.5° C.<br>IR(nujol) cm$^{-1}$: 3560, 3490, 3460, 1620<br>FABMS (m/z): 465(MH$^+$), 464(M$^+$) |
| 19 | 3,4-dihydroxyphenyl | M.p. 78–80° C. (decomposed)<br>IR(nujol) cm$^{-1}$: 3380, 1630<br>FABMS (m/z): 437(MH$^+$), 436(M$^+$) |
| 20 | 3-methoxy-4-hydroxyphenyl | M.p. 149–150.5° C.<br>IR(nujol) cm$^{-1}$: 3480, 3420, 3360, 3300, 1620<br>FABMS (m/z): 437 [(M + Na)$^+$] |
| 21 | 4-(2-methoxyethoxy)phenyl | M.p. 56° C. (gradually melting)<br>IR(nujol) cm$^{-1}$: 3360, 1630<br>FABMS (m/z): 501 [(M + Na)$^+$] |
| 22 | 4-isopropylphenyl | M.p. 109–112° C.<br>IR(nujol) cm$^{-1}$: 3600–3200, 1630, 1610, 1230<br>FABMS (m/z): 469 [(M + Na)$^+$] |
| 23 | 4-n-butylphenyl | Amorphous powders<br>IR(nujol) cm$^{-1}$: 3400, 3320, 1625, 1600<br>FABMS (m/z): 483 [(M + Na)$^+$] |
| 24 | 4-(hydroxymethyl)phenyl | M.p. 171–173° C.<br>IR(nujol) cm$^{-1}$: 3430, 3300, 3180, 1625, 1600<br>FABMS (m/z): 457 [(M + Na)$^+$] |
| 25 | 4-carboxyphenyl | M.p. 200.5–204° C.<br>IR(nujol) cm$^{-1}$: 3560, 3380, 1710, 1625, 1610, 1600<br>FABMS (m/z): 471 [(M + Na)$^+$] |

TABLE 4-continued (Structure: 2'-hydroxy-6'-O-R-phenyl ketone with -CH$_2$CH$_2$-Ar side chain)

(R: β-D-glucopyranosyl group)

| Ex. No. | Ar | Physical properties |
|---|---|---|
| 26 | 4-(CH$_2$)$_2$CH$_3$-phenyl | Amorphous powders<br>IR(nujol) cm$^{-1}$: 3440, 3320, 1625, 1600<br>FABMS (m/z): 469 [(M + Na)$^+$] |
| 27 | 4-pyridyl | M.p. 157–159° C.<br>IR(nujol) cm$^{-1}$: 3370, 3300, 1635, 1605<br>FABMS (m/z): 428 [(M + Na)$^+$] |
| 28 | 4-OCON(C$_2$H$_5$)$_2$-phenyl | M.p. 107–114° C.<br>IR(nujol) cm$^{-1}$: 3600–3200, 1700, 1620, 1600<br>FABMS (m/z): 542 [(M + Na)$^+$] |
| 29 | 4-CN-phenyl | M.p. 155–156.5° C.<br>IR(nujol) cm$^{-1}$: 3430, 3300, 2220, 1625, 1600<br>FABMS (m/z): 452 [(M + Na)$^+$] |
| 30 | 4-NHCOCH$_3$-phenyl | M.p. 105° C. (gradually melting)<br>IR(nujol) cm$^{-1}$: 3300, 1670, 1630<br>FABMS (m/z): 484 [(M + Na)$^+$] |

*Acetic acid is used as a solvent in the reduction reaction.

Example 31

(1) To dimethylformamide (50 ml) are added 2'-O-(2,3,4,6-tetra-O-acetyl-β-D-glucopyranosyl)-6'-hydroxyacetophenone (4.82 g) and potassium carbonate (4.14 g), and thereto is added dropwise benzyl bromide (2.56 g) with stirring. The mixture is stirred at room temperature for 2 hours. The reaction mixture is concentrated under reduced pressure, and to the residue are added ethyl acetate and water. The mixture is stirred and the organic layer is collected. The organic layer is washed with water, dried, and evaporated to remove the solvent. The residue is purified by silica gel column chromatography to give 6'-benzyloxy-2'-O-(2,3,4,6-tetra-O-acetyl-β-D-glucopyranosyl) acetophenone (3.2 g).

IR (nujol) cm$^{-1}$: 1760, 1700, 1600

FABMS (m/z): 595 [(M+Na)$^+$]

(2) To ethanol (30 ml) are added 6'-benzyloxy-2'-O-(2,3,4,6-tetra-O-acetyl-β-D-glucopyranosyl)acetophenone (2.9 g) and 4-tetrahydropyranyloxybenzaldehyde (1.56 g), and thereto is added dropwise a 50% aqueous potassium hydroxide solution (3 ml) with stirring. The mixture is treated in the same manner as in Example 1-(1), and the resulting crude product is dissolved in a mixture of acetic acid-water-tetrahydrofuran (2:1:2) (50 ml). The mixture is heated at 50° C. for three hours, and concentrated under reduced pressure. The residue is purified by silica gel column chromatography to give 6'-benzyloxy-2'-O-(β-D-glucopyranosyl)-4-hydroxychalcone (1.20 g).

IR (nujol) cm$^{-1}$: 3600–3200, 1660, 1600, 1260

FABMS (m/z): 531 [(M+Na)$^+$]

(3) 6'-Benzyloxy-2'-O-(β-D-glucopyranosyl)-4-hydroxychalcone (0.79 g) and triethylamine (0.19 g) are dissolved in dimethylacetoamide (30 ml), and thereto is added dropwise with stirring ethyl chlorocarbonate (0.20 g) under ice-cooling. The mixture is stirred at room temperature for one hour, and thereto are added ethyl acetate and water, and the mixture is stirred. The organic layer is collected, and washed with water, dried, and evaporated to remove the solvent. The residue is purified by silica gel column chromatography to give 6'-benzyloxy-4-ethoxycarbonyloxy-2'-O-(β-D-glucopyranosyl)chalcone (0.73 g).

FABMS (m/z): 603 [(M+Na)⁺]

(4) 6'-Benzyloxy-4-ethoxycarbonyloxy-2'-O-(β-D-glucopyranosyl)chalcone (0.70 g) is treated in the same manner as in Example 1-(2) to give 4-ethoxycarbonyl-2'-O-(β-D-glucopyranosyl)-6'-hydroxydihydrochalcone (0.48 g).

M.p. 65° C.~(gradually melting)

NMR (DMSO-$d_6$) δ: 1.28 (3H, t, J=7.1 Hz), 2.92 (2H, t, J=7.1 Hz), 3.1–3.3 (6H, m), 3.4–3.5 (1H, m), 3.6–3.7 (1H, m), 4.23 (2H, q, J=7.1 Hz), 4.5 (1H, t, J=5.7 Hz), 4.91 (1H, d, J=7.3 Hz), 5.03 (1H, d, J=5.3 Hz), 5.10 (1H, d, J=4.7 Hz), 5.27 (1H, d, J=5.2 Hz), 6.55 (1H, d, J=8.2 Hz), 6.68 (1H, d, J=8.3 Hz), 7.10 (2H, d, J=8.6 Hz), 7.24 (1H, t, J=8.3 Hz), 7.31 (2H, d, J=8.6 Hz), 10.94 (1H, s)

IR (nujol) cm⁻¹: 3600–3200, 1760, 1720, 1630, 1600

FABMS (m/z): 515 [(M+Na)⁺]

Examples 32–43

Using the corresponding starting compounds, the compounds listed in Table 5 are obtained in the same manner as in Example 31.

TABLE 5

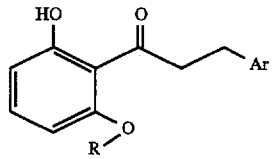

(R: β-D-glucopyranosyl group)

| Ex. No. | Ar | Physical properties |
|---|---|---|
| 32 | 4-(OCOOCH₂CH(CH₃)₂)C₆H₄– | Amorphous powders<br>IR(nujol) cm⁻¹: 3360, 1760, 1740, 1630<br>FABMS (m/z): 543 [(M+Na)⁺] |
| 33 | 4-(OCOO(CH₂)₂OCH₃)C₆H₄– | Amorphous powders<br>IR(nujol) cm⁻¹: 3340, 1760, 1630<br>FABMS (m/z): 545 [(M+Na)⁺] |
| 34 | 4-(OCOCH₃)C₆H₄– | M.p. 56° C.~(gradually melting)<br>NMR(DMSO-$d_6$) δ: 2.24(3H, s), 2.91(2H, t, J=7.5Hz), 3.11–3.37(6H, m), 3.46(1H, m), 3.70(1H, ddd, J=1.8, 5.3, 11.5Hz), 4.56(1H, t, J=5.7Hz), 4.91(1H, d, J=7.3Hz), 5.02(1H, t, J=5.2Hz), 5.09(1H, d, J=4.7Hz), 5.26(1H, d, J=5.3Hz), 6.55(1H, d, J=8.1Hz), 6.68(1H, d, J=8.1Hz), 7.00(2H, ddd, J=2.0, 2.7, 8.5Hz), 7.24(1H, t, J=8.3Hz), 7.29(2H, dd, J=2.1, 8.6 Hz), 10.95(1H, s)<br>FABMS (m/z): 485 [(M+Na)⁺] |
| 35 | 4-(OCOCH₂CH₃)C₆H₄– | M.p. 48° C.~(gradually melting)<br>NMR(DMSO-$d_6$) δ: 1.12(3H, t, J=7.5Hz), 2.57(2H, q, J=7.5Hz), 2.91(2H, t, J=7.4Hz), 3.11–3.37(6H, m), 3.46(1H, m), 3.70(1H, ddd, J=1.7, 5.2, 11.7Hz), 4.56(1H, t, J=5.7Hz), 4.91(1H, d, J=7.3Hz), 5.02(1H, d1 J=5.3Hz), 5.09(1H, d, J=4.7Hz), 5.26(1H, d, J=5.2 6.55(1H, d, J=8.1Hz), 6.68(1H, d, J=8.4Hz), 7.00(2H, ddd, J=2.0, 2.7, 8.5Hz), 7.24(1H, t, J=8.3Hz), 7.29(2H, dd, J=2.0, 8.6Hz), 10.96 (1H, s)<br>FABMS (m/z): 499 [(M+Na)⁺] |

TABLE 5-continued

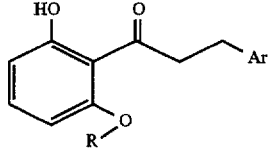

(R: β-D-glucopyranosyl group)

| Ex. No. | Ar | Physical properties |
|---|---|---|
| 36 | 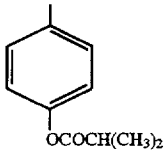<br>OCOCH(CH₃)₂ | Foam<br>NMR(DMSO-d₆) δ: 1.22(6H, t, J=7.0Hz), 2.79(1H, sev., J=7.0Hz), 2.91(2H, t, J=7.5 Hz), 3.11–3.37(6H, m), 3.46(1H, m), 3.70(1H, m), 4.56(1H, t, J=5.6Hz), 4.91 (1H, d, J=7.4 Hz), 5.02(1H, d, J=5.1Hz), 5.09(1H, d, J=4.3 Hz), 5.26(1H, d, J=5.1Hz), 6.55(1H, d, J=7.7 Hz), 6.68(1H, d, J=8.0Hz), 6.99(2H, ddd, J=2.0, 2.8, 8.5Hz), 7.24(1H, t, J=8.3Hz), 7.29 (2H, ddd, J=2.1, 2.7, 8.5Hz), 10.97(1H, s)<br>FABMS (m/z): 513 [(M + Na)⁺] |
| 37 | 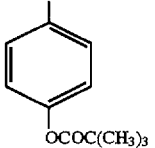<br>OCOC(CH₃)₃ | Foam<br>NMR(DMSd-d₆) δ: 1.29(9H, s), 2.91(2H, t, J=7.3Hz), 3.11–3.37(6H, m), 3.46(1H, m), 3.70(1H, ddd, J=1.7, 5.2, 11.6Hz), 4.56(1H, t, J=5.7Hz), 4.91(1H, d, J=7.4Hz), 5.02(1H, d, J=5.2Hz), 5.09(1H, d, J=4.7Hz), 5.26(1H, d, J=5.2Hz), 6.55(1H, dd, J=0.8, 8.4Hz), 6.68 (1H, d, J=7.9Hz), 6.97(2H, ddd, J=2.0, 2.7, 8.6 Hz), 7.25(1H, t, J=8.3 Hz), 7.29 (2H, dd, J=2.0, 8.6 Hz), 10.99(1H, s)<br>FABMS (m/z): 527 [(M+Na)⁺] |
| 38 | 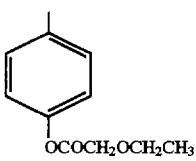<br>OCOCH₂OCH₂CH₃ | Foam<br>NMR(DMSO-d₆) δ: 1.16(3H, t, J=7.0Hz), 2.91(2H, t, J=7.4Hz), 3.12–3.38(6H, m), 3.46 (1H, m), 3.59(2H, q, J=7.0Hz), 3.70(1H, ddd, J=1.8, 5.4, 11.5Hz), 4.35(2H, s), 4.56(1H, t, J=5.8Hz), 4.91(1H, d, J=7.4Hz), 5.02(1H, t, J=5.2Hz), 5.09(1H, d, J=4.7Hz), 5.26(1H, d, J=5.2Hz), 6.55(1H, d, J=8.1Hz), 6.68(1H, d J=8.3Hz), 7.04(2H, ddd, J=2.0, 2.7, 8.6Hz), 7.24(1H, t, J=8.3Hz), 7.31(2H, ddd, J=2.0, 2.7, 8.6Hz), 10.95(1H, s)<br>FABMS (m/z): 529 [(M + Na)⁺] |
| 39 | 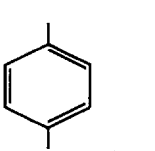<br>OCO(CH₂)₃<br>\|<br>COOCH₂CH₃ | NMR(DMSO-d₆) δ: 1.19(3H, t, J=7.1Hz), 1.87(2H, quint, J=7.4Hz), 2.41(2H, t, J=7.3 Hz), 2.61(2H, t, J=7.4Hz), 2.91(2H, t, J=7.5 Hz), 3.11–3.37(6H, m), 3.46(1H, m), 3.70(1H, ddd, J=1.6, 5.2, 11.7Hz), 4.07(2H, q, J=7.1 Hz), 4.55(1H, t, J=5.6Hz), 4.91(1H, d, J=7.3 Hz), 5.02(1H, d, J=5.3Hz), 5.08(1H, d, J=4.6 Hz), 5.26(1H, d, J=5.1Hz), 6.55(1H, d, J=8.3 Hz), 6.68(1H, d, J=8.4Hz), 7.00(2H, ddd, J=1.8, 2.5, 8.5Hz), 7.24(1H, t, J=8.3Hz), 7.29 (2H, d, J=8.5Hz), 10.96(1H, s)<br>FABMS (m/z): 585 [(M + Na)⁺] |
| 40 | 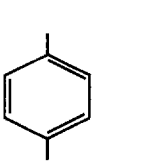<br>OCOOC(CH₃)₃ | NMR(DMSO-d₆) δ: 1.48(9H, s), 2.91(2H, t, J=7.3Hz), 3.1–3.5(7H, m), 3.70(1H, dd, J=5.2, 11.5Hz), 4.57(1H, t, J=5.6Hz), 4.91(1H, d, J=7.3Hz), 5.03(1H, d, J=4.9Hz), 5.10(1H, d, J=3.9Hz), 5.27(1H, d, J=4.9Hz), 6.55(1H, d, J=7.8Hz), 6.68(1H, d, J=8.3Hz), 7.06(2H, d, J=8.8Hz), 7.24(1H, t, J=8.3Hz), 7.29(2H, d, J=8.3Hz), 10.96(1H, s)<br>FABMS (m/z): 543 [M + Na)⁺] |

TABLE 5-continued

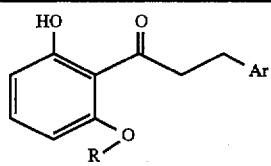

(R: β-D-glucopyranosyl group)

| Ex. No. | Ar | Physical properties |
|---|---|---|
| 41 | [4-(phenoxycarbonyloxy)phenyl] | NMR(DMSO-d₆) δ: 2.93(2H, t, J=7.3Hz), 3.12–3.37(6H, m), 3.46(1H, m), 3.70(1H, ddd, J=1.6, 5.3, 11.7Hz), 4.56(1H, t, J=5.7Hz), 4.91(1H, d, J=7.3Hz), 5.02(1H, d, J=5.2Hz), 5.10(1H, d, J=4.7Hz), 5.27(1H, d, J=5.1Hz), 6.55(1H, d, J=8.1Hz), 6.68(1H, d, J=8.4Hz), 7.24(1H, t, J=8.3Hz), 7.25(2H, dd, J=2.1, 8.5 Hz), 7.29–7.39(5H, m), 7.47(2H, m), 10.95 (1H, s) FABMS (m/z): 563 [(M + Na)⁺] |
| 42 | [4-(benzoyloxy)phenyl] | NMR(DMSO-d₆) δ: 2.95(2H, t, J=7.3Hz), 3.12–3.38(6H, m), 3.47(1H, m), 3.71(1H, ddd, J=1.7, 5.3, 11.8Hz), 4.57(1H, t, J=5.7Hz), 4.92(1H, d, J=7.3Hz), 5.02(1H, d, J=5.2Hz), 5.10(1H, d, J=4.6Hz), 5.28(1H, d, J=5.2Hz), 6.56(1H, d, J=7.8Hz), 6.69(1H, d, J=8.1Hz), 7.17(2H, ddd, J=2.0, 2.6, 8.5Hz), 7.25(1H, t, J=8.3Hz), 7.36(2H, ddd, J=1.9, 2.6, 8.5Hz), 7.61(2H, m), 7.75(1H, m), 8.13(2H, m), 10.98 (1H, s) FABMS (m/z): 547 [(M + Na)⁺] |
| 43 | [4-(4-methoxybenzoyloxy)phenyl] | NMR(DMSO-d₆) δ: 2.94(2H, t, J=7.3Hz), 3.12–3.38(6H, m), 3.47(1H, m), 3.71(1H, ddd, J=1.7, 5.2, 11.4Hz), 3.87(3H, s), 4.57(1H, t, J=5.6Hz), 4.92(1H, d, J=7.3Hz), 5.02(1H, d, J=5.3Hz), 5.09(1H, d, J=4.7Hz), 5.27(1H, d, J=5.1Hz), 6.56(1H, d, J=8.1Hz), 6.69(1H, d, J=8.4Hz), 7.12(2H, dd, J=2.1, 9.0Hz), 7.13 (2H, dd, J=1.9, 8.5Hz), 7.25(1H, t, J=8.3Hz), 7.34(2H, d, J=8.5Hz), 8.07(2H, dd, J=2.0, 8.9 Hz), 10.98(1H, s) FABMS (m/z): 577 [(M + Na)⁺] |

Example 44

2'-O-(2,3,4,6-Tetra-O-acetyl-β-D-glucopyranosyl)-6'-hydroxyacetophenone (1.2 g) and p-methylthiobenzaldehyde (0.57 g) are treated in the same manner as in Example 1-(1) to give crude 2'-O-(β-D-glucopyranosyl)-6'-hydroxy-4-methylthiochalcone (1.71 g). Separately, a solution of sodium hydrogen telluride in ethanol (20 ml) is prepared from tellurium (0.3 g) and sodium borohydride (0.23 g), and thereto is added the above product, and the mixture is reacted at room temperature for one hour. The reaction mixture is poured into ice-water, and the precipitated insoluble materials are removed by filtration. To the filtrate is added chloroform, and the mixture is stirred, and the organic layer is collected. The organic layer is dried, concentrated, and the residue is purified by silica gel column chromatography to give 2'-O-(β-D-glucopyranosyl)-6'-hydroxy-4-methylthiodihydrochalcone (470 mg).

M.p. 135°–136° C.

IR (nujol) cm⁻¹: 3600–3200, 1620, 1600, 1230

FABMS (m/z): 473 [(M+Na)⁺]

Example 45

Using the corresponding starting compounds, there is obtained 2'-O-(β-D-glucopyranosyl)-6'-hydroxy-3-(2-thienyl)propiophenone in the same manner as in Example 44.

M.p. 62°–70° C.

IR (nujol) cm⁻¹: 3600–3000, 1620, 1600, 1230

FABMS (m/z): 433 [(M+Na)⁺]

Example 46

2'-O-(2,3,4,6-Tetra-O-acetyl-β-D-glucopyranosyl)-6'-hydroxyacetophenone (2 g) and 4-diethoxymethylbenzaldehyde (1.02 g) are treated in the same manner as in Example 1-(1) and (2). Subsequently, the obtained product is stirred in a mixture of acetic acid-water (2 ml/2 ml) at room temperature for 30 minutes. The mixture is diluted with a mixture of chloroform-methanol (10:1), and the precipitated crystals are recrystallized from methanol to give 2'-O-(β-D-glucopyranosyl)-6'-hydroxy-4-formyldihydrochalcone (531 mg).

M.p. 173°–174° C.

IR (nujol) cm$^{-1}$: 3510, 3330, 1685, 1620, 1600

FABMS (m/z): 455 [(M+Na)$^+$]

Example 47

The compound (901 mg) obtained in Example 44 is dissolved in dichloromethane-dimethylformamide (30 ml/10 ml), and thereto is added m-chloroperbenzoic acid (520 mg) under ice-cooling. The mixture is stirred at room temperature for 15 minutes, and concentrated in vacuo. The residue is poured into a saturated aqueous sodium hydrogen carbonate solution, and extracted with a mixture of ethyl acetate-tetrahydrofuran. The extract is dried, evaporated to remove the solvent, and the resulting residue is purified by silica gel column chromatography to give 2'-O-(β-D-glucopyranosyl)-6'-hydroxy-4-methylsulfonyldihydrochalcone (507 mg) and 2'-O-(β-D-glucopyranosyl)-6'-hydroxy-4-methylsulfonyldihydrochalcone (338 mg).

2'-O-(β-D-Glucopyranosyl)-6'-hydroxy-4-methylsulfonyldihydrochalcone

M.p. 84° C.~(gradually melting)

IR (nujol) cm$^{-1}$: 3600–3200, 1630, 1600, 1300, 1230

FABMS (m/z): 489 [(M+Na)$^+$]

2'-O-(β-D-Glucopyranosyl)-6'-hydroxy-4-methylsulfonyldihydrochalcone

M.p. 85° C.~(gradually melting)

IR (nujol) cm$^{-1}$: 3600–3200, 1630, 1600, 1300, 1230

FABMS (m/z): 505 [(M+Na)$^+$]

Example 48

(1) 6-Benzyl-2'-O-(2,3,4,6-tetra-O-acetyl-β-D-glucopyranosyl)acetophenone (2.9 g) obtained in Example 31-(1) and 4-tetrahydropyranyloxybenzaldehyde (1.56 g) are dissolved in ethanol (30 ml), and thereto is added dropwise a 50% aqueous potassium hydroxide solution (3 ml) with stirring. The mixture is treated in the same manner as in Example 1-(1), and the resulting crude product is purified by silica gel column chromatography to give 2'-O-(β-D-glucopyranosyl)-6'-benzyloxy-4-tetrahydropyranyloxychalcone (2.2. g). The above product (593 mg) and tetrabutyl ammonium hydrogen sulfate (136 mg) are added into a two-phase solvent of dichloromethane-10% aqueous sodium hydroxide solution (10 ml/5 ml). To the mixture is added benzyl chloroformate (1.02 g), and the mixture is stirred at room temperature for one hour. The organic layer is collected, and the aqueous layer is extracted with chloroform. The combined organic layers are dried, and evaporated to remove the solvent. The resulting crude product is dissolved in a mixture of acetic acid-water-tetrahydrofuran (10 ml/3.5 ml/2 ml), and the mixture is stirred at room temperature for 40 minutes, and further stirred at 40° C. for 30 minutes. The reaction solution is diluted with ethyl acetate, and washed with water, dried, and evaporated to remove the solvent. The residue is purified by silica gel column chromatography to give yellow foam (847 mg).

IR (nujol) cm$^{-1}$: 1760, 1750

FABMS (m/z): 1067 [(M+Na)$^+$]

(2) A mixture of the above product (816 mg), N-benzyloxycarbonylglycine (245 mg), dicyclohexylcarbodiimide (266 mg), 1-hydroxybenzotriazol hydrate (174 mg) and dimethylformamide (10 ml) is stirred at room temperature for 13 hours. The reaction solution is diluted with ethyl acetate, and the insoluble materials are removed by filtration. The filtrate is washed with water, dried, and evaporated to remove the solvent. The residue is purified by silica gel column chromatography to give pale yellow foam (848 mg).

IR (nujol) cm$^{-1}$: 3400, 1765, 1730, 1650

FABMS (m/z): 1258 [(M+Na)$^+$]

(3) The above product (811 mg) is dissolved in ethanol (10 ml), and thereto are added 10% palladium-carbon (0.2 g) and 19% hydrogen chloride-ethanol (0.2 ml), and the mixture is subjected to catalytic hydrogenation at room temperature. After the reaction is complete, the catalyst is removed by filtration, and the filtrate is concentrated. The residue is pulverized in diethyl ether. The resulting powders are collected by filtration, dried to give 2'-O-(β-D-glucopyranosyl)-6'-hydroxy-4-glycyloxydihydrochalcone hydrochloride (130 mg).

M.p. 72° C.~(gradually melting)

NMR (DMSO-d$_6$) δ: 2.93 (2H, t, J=7.3 Hz), 3.12–3.53 (7H, m), 3.69 (1H, d, J=10.9 Hz), 4.07 (2H, s), 4.69 (1H, bro), 4.91 (1H, d, J=7.4 Hz), 5.10 (1H, bro), 5.19 (1H, bro), 5.29 (1H, d, J=4.1 Hz), 6.58 (1H, d, J=8.1 Hz), 6.68 (1H, J=8.3 Hz), 7.08 (2H, ddd, J=2.0, 2.6, 8.5 Hz), 7.24 (1H, t, J=8.3 Hz), 7.36 (2H, d, J=8.7 Hz), 8.56 (3H, bro), 10.99 (1H, s)

IR (nujol) cm$^{-1}$: 3300, 1770, 1630

Example 49

Using the corresponding starting compounds, there is obtained 2'-O-(β-D-glucopyranosyl)-6'-hydroxy-4-L-valyloxydihydrochalcone hydrochloride in the same manner as in Example 48.

M.p. 141° C.~(gradually melting)

NMR (DMSO-d$_6$) δ: 1.08 (3H, d, J=7.0 Hz), 1.11 (3H, d, J=7.0 Hz), 2.34 (1H, m), 2.93 (2H, t, J=7.3 Hz), 3.12–3.52 (7H, m), 3.70 (1H, d, J=11.7 Hz), 4.12 (1H, d, J=4.9 Hz), 4.59 (1H, broad), 4.91 (1H, d, J=7.5 Hz), 5.08 (1H, d, J=4.8 Hz), 5.17 (1H, d, J=2.9 Hz), 5.29 (1H, d, J=5.1 Hz), 6.58 (1H, d, J=8.4 Hz), 6.68 (1H, d, J=8.3 Hz), 7.08 (2H, d, J=8.5 Hz), 7.24 (1H, t, J=8.3 Hz), 7.37 (2H, d, J=8.5 Hz), 8.74 (3H, broad), 10.99 (1H, s)

FABMS (m/z): 542 [(M+Na)$^+$]

Example 50

Using the corresponding starting compounds, there is obtained 2'-O-(β-D-glucopyranosyl)-6'-hydroxy-4-L-phenylalanyloxydihydrochalcone hydrochloride in the same manner as in Example 48.

M.p. 182° C.~(gradually melting)

NMR (DMSO-d$_6$) δ: 2.90 (2H, t, J=7.3 Hz), 3.13–3.51 (9H, m), 3.69 (1H, dd, J=1.2, 11.4 Hz), 4.51 (1H, dd, J=5.9, 8.1 Hz), 4.8–5.5 (4H, broad), 4.91 (1H, d, J=7.6 Hz), 6.57 (1H, d, J=8.3 Hz), 6.68 (1H, d, J=8.3 Hz), 6.86 (2H, ddd, J=1.9, 2.6, 8.5 Hz), 7.24 (1H, t, J=8.3 Hz), 7.31 (2H, d, J=8.6 Hz), 7.37 (5H, m), 8.88 (3H, broad), 10.98 (1H, s)

FABMS (m/z): 590 [(M+Na)$^+$]

Example 51

To a mixture of 4-methoxy-6'-hydroxy-2'-O-β-D-glucopyranosyldihydrochalcone (869 mg), potassium carbonate (830 mg) and dimethylformamide (10 ml) is added dropwise methyl iodide (426 mg), and the mixture is stirred at room temperature overnight. The mixture is concentrated under reduced pressure, and to the residue are added ethyl acetate and water, and stirred. The organic layer is collected, washed with water, dried, and evaporated to remove the solvent. The residue is purified by silica gel column chromatography (solvent; chloroform/methanol) to give 4,6'-dimethoxy-2'-O-β-D-glucopyranosyldihydrochalcone (0.8 g).

NMR (DMSO-$d_6$) δ: 2.80 (2H, t, J=8.1 Hz), 2.9–3.3 (7H, m), 3.44 (1H, dd, J=6.1, 11.9 Hz), 3.71 (6H, s), 4.55 (1H, t, J=5.9 Hz), 4.87 (1H, d, J=7.7 Hz), 5.02 (1H, d, J=5.3 Hz), 5.08 (1H, d, J=4.9 Hz), 5.19 (1H, d, J=5.5 Hz), 6.73 (1H, d, J=8.3 Hz), 6.82 (3H, d, J=8.7 Hz), 7.15 (2H, d, J=8.7 Hz), 7.30 (1H, t, J=8.4 Hz)

FABMS (m/z): 471 [(M+Na)$^+$]

Examples 52–53

Using the corresponding starting compounds, the compounds listed in Table 6 are obtained in the same manner as in Example 51.

TABLE 6

(R: β-D-glucopyranosyl group)

| Ex. No. | R$^5$O | Physical properties |
|---|---|---|
| 52 | CH$_3$(CH$_2$)$_3$O— | M.p. 104–107° C.<br>IR(nujol) cm$^{-1}$: 3340(broad); 1690<br>FABMS (m/z): 513 [(M + Na)$^+$] |
| 53 | (CH$_3$)$_2$CHO— | IR(nujol) cm$^{-1}$: 3340(broad), 1700<br>FABMS (m/z): 499 [(M + Na)$^+$] |

Example 54

4-Methoxy-6'-hydroxy-2'-O-β-D-glucopyranosyldihydrochalcone (868 mg) is dissolved in dimethylacetoamide (10 ml), and thereto is added triethylamine (212 mg), and then thereto is added ethyl chlorocarbonate (228 mg) under ice-cooling. The mixture is stirred at the same temperature for 40 minutes, and thereto is added ethyl acetate. The mixture is stirred and the organic layer is collected, washed with water, dried and evaporated to remove the solvent. The residue is purified by silica gel column chromatography (solvent; chloroform/methanol) to give 4-methoxy-6'-ethoxycarbonyl-2'-O-β-D-glucopyranosyldihydrochalcone (534 mg).

NMR (DMSO-$d_6$) δ: 1.26 (3H, t, J=7.1 Hz), 2.80 (2H, m), 3.0–3.5 (7H, m), 3.70 (1H, m), 3.71 (3H, s), 4.18 (2H, q, J=7.1 Hz), 4.57 (1H, t, J=5.7 Hz), 5.02 (1H, d, J=7.4 Hz), 5.05 (1H, d, J=5.3 Hz), 5.11 (1H, d, J=4.8 Hz), 5.31 (1H, d, J=5.5 Hz), 6.82 (2H, ddd, J=2.1, 3.0, 8.7 Hz), 6.95 (1H, d, J=8.4 Hz), 7.15 (2H, ddd, J=2.0, 2.9, 8.6 Hz), 7.18 (1H, t, J=7.9 Hz), 7.44 (1H, t, J=8.3 Hz)

FABMS (m/z): 529 [(M+Na)$^+$]

Examples 55–60

Using the corresponding starting compounds, the compounds listed in Table 7 are obtained in the same manner as in Example 54.

TABLE 7

(R: β-D-glucopyranosyl group)

| Ex. No. | Y | R$^5$O | Physical properties |
|---|---|---|---|
| 55 | CH$_3$O— | (CH$_3$)$_2$CH-CH$_2$OCOO— | NMR(DMSO-$d_6$) δ: 0.91(6H, d, J=6.8 Hz), 1.94(1H, m), 2.80(2H, m), 3.0–3.5 (7H, m), 3.70(1H, m), 3.71(3H, s), 3.94 (2H, d, J=6.6Hz), 4.57(1H, t, J=5.8Hz), 5.02(1H, d, J=7.6Hz), 5.05(1H, d, J=5.3Hz), 5.11(1H, d, J=4.8Hz), 5.31 (1H, d, J=5.5Hz), 6.82(2H, ddd, J=2.1; 3.0, 8.7Hz), 6.95(1H, d, J=8.4Hz), 7.15(2H, dd, J=2.0, 8.7Hz), 7.18(1H, d, J=8.3Hz), 7.44(1H, t, J=8.3Hz) FABMS (m/z): 557 [(M + Na)$^+$] |
| 56 | CH$_3$COO— | CH$_3$COO— | NMR(DMSO-$d_6$) δ: 2.05(3H, s), 2.24 (3H, s), 2.87(2H, m), 3.0–3.5(7H, m), 3.70(1H, ddd, J=1.6, 5.3, 11.5Hz), 4.57 (1H, t, J=5.8Hz), 5.00(1H, d, J=7.4Hz), 5.04(1H, d, J=5.3Hz), 5.10(1H, d, J=4.8Hz), 5.35(1H, d, J=5.5Hz), 6.83 (1H, d, J=7.7Hz), 7.01(2H, ddd, J=2.0, 2.7, 8.5Hz), 7.15(1H, d, J=8.4Hz), 7.28(2H, ddd, J=2.0, 2.7, 8.5Hz), 7.41 (1H, t, J=8.3Hz) |

TABLE 7-continued (R: β-D-glucopyranosyl group)

| Ex. No. | Y | R⁵O | Physical properties |
|---|---|---|---|
| 57 | $(CH_3)_2CH-COO-$ | $(CH_3)_2CH-COO-$ | FABMS (m/z): 527 [(M + Na)⁺] NMR(DMSO-d₆) δ: 1.12(6H, d, J=7.0 Hz), 1.22(6H, d, J=7.0Hz), 2.62(1H, m), 2.79(1H, m), 2.86(2H, t, J=7.7Hz), 3.0–3.5(7H, m), 3.70(1H, ddd, J=1.7, 5.4, 11.7Hz), 4.58(1H, t, J=5.7Hz), 5.01(1H, d, J=7.5Hz), 5.04(1H, d, J=5.2Hz), 5.10(1H, d, J=4.8Hz), 5.35 (1H, d, J=5.5Hz), 6.82(1H, dd, J=0.7, 8.1Hz), 6.99(2H, dd, J=2.0, 8.6Hz), 7.15(1H, d, J=8.1Hz), 7.27(2H, dd, J=1.9, 8.5Hz), 7.42(1H, t, J=8.3Hz) |
| 58 | $(CH_3)_2CH-CH_2OCOO-$ | $(CH_3)_3C-COO-$ | FABMS (m/z): 583 [(M + Na)⁺] NMR(DMSO-d₆) δ: 0.94(6H, d, J=6.8 Hz), 1.18(9H, s), 1.97(1H, m), 2.86 (2H, t, J=7.6Hz), 3.0–3.5(7H, m), 3.71 (1H, m), 3.99(2H, d, J=6.6Hz), 4.58 (1H, t, J=5.8Hz), 5.00(1H, d, J=7.4Hz), 5.04(1H, d, J=5.3Hz), 5.10(1H, d, J=4.8Hz), 5.35(1H, d, J=5.5Hz), 6.81 (1H, d, J=8.1Hz), 7.11(2H, dd, J=2.7, 8.5Hz), 7.16(1H, d, J=8.6Hz), 7.28 (2H, d, J=8.6Hz), 7.42(1H, t, J=8.3Hz) |
| 59 | $CH_3CH_2O-COO-$ | $CH_3CH_2O-COO-$ | FABMS (m/z): 637 [(M + Na)⁺] NMR(DMSO-d₆) δ: 1.25(3H, t, J=7.1 Hz), 1.28(3H, t, J=7.1Hz), 2.88(2H, m), 3.1–3.3(5H, m), 3.37(1H, m), 3.46(1H, m), 3.70(1H, ddd, J=1.5, 5.1, 11.3Hz), 4.19(2H, q, J=7.1Hz), 4.23(2H, q, J=7.1Hz), 4.58(1H, t, J=5.8Hz), 5.02 (1H, d, J=7.5Hz), 5.05(1H, d, J=5.3 Hz), 5.12(1H, d, J=5.0Hz), 5.36(1H, d, J=5.5Hz), 6.96(1H, d, J=7.4Hz), 7.11 (2H, ddd, J=2.0, 2.8, 8.6Hz), 7.19(1H, d, J=8.1Hz), 7.30(2H, dd, J=2.0, 8.7 Hz), 7.45(1H, t, J=8.3Hz) |
| 60 | $(CH_3)_2CH-CH_2OCOO-$ | $(CH_3)_2CH-CH_2OCOO-$ | FABMS (m/z): 587 [(M + Na)⁺] NMR(DMSO-d₆) δ: 0.91(6H, d, J=6.7 Hz), 0.93(6H, d, J=6.8Hz), 1.96(2H, m), 2.87(2H, t, J=7.4Hz), 3.1–3.3(5H, m), 3.37(1H, m), 3.47(1H, m), 3.70 (1H, ddd, J=1.6, 5.2, 11.4Hz), 3.95(2H, d, J=6.6Hz), 3.99(2H, d, J=6.6Hz), 4.58(1H, t, J=5.7Hz), 5.02(1H, d, J=7.4Hz), 5.05(1H, d, J=5.3Hz), 5.11 (1H, d, J=4.9Hz), 5.36(1H, d, J=5.5 Hz), 6.96(1H, d, J=7.4Hz), 7.11(2H, ddd, J=2.1, 2.7, 8.6Hz), 7.19(1H, d, J=8.0Hz), 7.29(2H, ddd, J=1.9, 2.7, 8.6 Hz), 7.45(1H, t, J=8.3Hz) FABMS (m/z): 643 [(M + Na)⁺] |

Example 61

(1) To a mixture of ethanol-methanol (1:1) (80 ml) are added 2'-O-[2,3,6-tri-O-acetyl-4-O-(2,3,4,6-tetra-O-acetyl-α-D-glucopyranosyl)-β-D-glucopyranosyl]-6'-hydroxyacetophenone (4.3 g) and p-anisaldehyde (1.52 g), and thereto is added dropwise a 50% aqueous potassium hydroxide solution (6 ml) with stirring. The mixture is treated in the same manner as in Example 1-(1), and the resulting crude product is purified by silica gel column chromatography to give 2'-O-[4-O-(α-D-glucopyranosyl)-β-D-glucopyranosyl]-6'-hydroxy-4-methoxychalcone (1.71 g).

IR (nujol) cm⁻¹: 3600–2400, 1620

FABMS (m/z): 595 [(M+Na)⁺], 271

(2) 2'-O-[4-O-(α-D-Glucopyranosyl)-β-D-glucopyranosyl]-6'-hydroxy-4-methoxychalcone (1.64 g) is dissolved in tetrahydrofuran (30 ml), and the mixture is treated in the same manner as in Example 1-(2) to give 2'-O-[4-O-(α-D-glucopyranosyl)-β-D-glucopyranosyl]-6'-hydroxy-4-methoxydihydrochalcone (931 mg).

M.p. 92° C.~(gradually melting)

NMR (DMSO-d$_6$) δ: 2.83 (2H, t, J=7.3 Hz), 3.22 (2H, t, J=7.3 Hz), 3.0–3.8 (12H, m), 3.71 (3H, s), 4.55 (2H, m), 4.90 (1H, d, J=4.4 Hz), 4.92 (1H, d, J=5.4 Hz), 4.97 (1H, d, J=7.8 Hz), 5.06 (1H, d, J=3.9 Hz), 5.37 (1H, d, J=5.9 Hz), 5.48 (1H, d, J=5.9 Hz), 5.62 (1H, d, J=2.9 Hz), 6.55 (1H, d, J=7.8 Hz), 6.68 (1H, d, J=8.3 Hz), 6.82 (2H, dd, J=2.9, 8.8 Hz), 7.17 (2H, dd, J=2.9, 8.3 Hz), 7.24 (1H, t, J=8.3 Hz), 10.95 (1H, brs)

IR (nujol) cm$^{-1}$: 3340, 1620

FABMS (m/z): 597 (NH$^+$)

Examples 62–65

Using the corresponding starting compounds, the compounds listed in Table 8 are obtained in the same manner as in Example 61.

TABLE 8

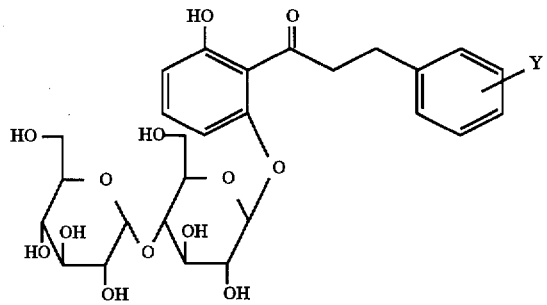

| Ex. No. | Y | Physical properties |
|---|---|---|
| 62 | 4-HO— | M.p. 165° C. ~ (gradually melting)<br>NMR (DMSO-d$_6$) δ: 2.78 (2H, t, J = 7;3 Hz), 3.0–3.8 (14H, m), 4.55 (2H, m), 4.90 (1H, d, J = 4.4 Hz), 4.93 (1H, d, J = 5.0 Hz), 4.97 (1H, d, J = 7.8 Hz), 5.06 (1H, d, J = 3.4 Hz), 5.37 (1H, d, J = 5.9 Hz), 5.49 (1.H, d, J = 5.9 Hz), 5.62 (1H, d, J = 2.9 Hz), 6.55 (1H, d, J = 8.3 Hz), 6.64 (2H, d, J = 8.3 Hz), 6.67 (1H, d, J = 8.3 Hz), 7.03 (2H, d, J = 8.3 Hz), 7.24 (1H, t, J = 8.3 Hz), 9.10 (1H, brs), 10.97(1H, brs)<br>IR (nujol) cm$^{-1}$: 3320, 1630<br>FABMS (m/z): 583 (NH$^+$) |
| 63 | H— | M.p. 89° C. ~ (gradually melting)<br>NMR (DMSO-d$_6$) δ: 2.90 (2H, t, J = 7.3 Hz), 3.03–3.78 (14H, m), 4.51 (1H, t, J = 5.5 Hz), 4.56 (1H, t, J = 5.7 Hz), 4.89 (1H, d, J = 4.9 Hz), 4.91 (1H, d, J = 5.6 Hz), 4.98 (1H, d, J = 7.9 Hz), 5.06 (1H, d, J = 3.7 Hz), 5.37 (1H, d, J = 5.8 Hz), 5.47 (1H, d, J = 6.1 Hz), 5.61 (1H, d, J = 3.3 Hz), 6.56 (1H, d, J = 8.3 Hz), 6.68 (1H, d, J = 8.1 Hz), 7.17 (1H, m), 7.24 (1H, t, J = 8.3 Hz), 7.26 (4H, m), 10.93 (1H, s)<br>FABMS (m/z): 589 [(M+Na)$^+$] |
| 64 | 4-Cl— | M.p. 91° C. ~ (gradually melting)<br>NMR (DMSO-d$_6$) δ: 2.90 (2H, t, J = 7.3 Hz), 3.03–3.77 (14H, m), 4.52 (1H, t, J = 5.5 Hz), 4.57 (1H, t, J = 5.7 Hz), 4.89 (1H, d, J = 4.9 Hz), 4.92 (1H, d, J = 5.6 Hz), 4.98 (1H, d, J = 7.8 Hz), 5.06 (1H, d, J = 3.9 Hz), 5.39 (1H, d, J = 5.7 Hz), 5.48 (1H, d, J = 6.1 Hz), 5.62 (1H, d, J = 3.3 Hz), 6.55 (1H, d, J = 8.4 Hz), 6.68 (1H, d, J = 8.5 Hz), 7.24 (1H, t, J = 8.3 Hz), 7.30 (4H, s), 10.91 (1H, s)<br>FABMS (m/z): 623, 625 [(M+Na)$^+$] |
| 65 | 3-CH$_3$— | M.p. 92° C. ~ (gradually melting)<br>NMR (DMSO-d$_6$) δ: 2.27 (3H, s), 2.86 (2H, t, J = 7.5 Hz), 3.03-3.78 (14H, m), 4.51 (1H, t, J = 5.5 Hz), 4.56 (1H, t, J = 5.7 Hz), 4.89 (1H, d, J = 4.9 Hz), 4.91 (1H, d, J = 5.6 Hz), 4.98 (1H, d, J = 7.7 Hz), 5.05 (1H, d, J = 3.7 Hz), 5.36 (1H, d, J = 5.8 Hz), 5.48 (1H, d, J = 6.1 Hz), 5.61 (1H, d, J = 3.2 Hz), 6.56 (1H, d, J = 8.1 Hz), 6.68 (1H, d, J = 8.4 Hz), 6.97 (1H, d, J = 7.3 Hz), 7.04 (1H, d, J = 7.7 Hz), 7.07 (1H, s), 7.14 (1H, t, J = 7.4 Hz), 7.25 (1H, t, J = 8.3 Hz), 10.95 (1H, s)<br>FABMS (m/z): 603 [(M+Na)$^+$] |

Example 66

To a mixture of dioxane-methylene chloride (20 ml/100 ml) is added 4-methoxy-6'-hydroxy-2'-O-β-D-glucopyranosyldihydrochalcone (2.79 g), and thereto are added benzaldehydedimethylacetal (1.47 g) and p-toluenesulfonic acid (120 mg) with stirring, and the mixture is stirred at room temperature for 20 hours. The reaction solution is washed with water, dried, and filtered, and the filtrate is concentrated under reduced pressure. The residue is purified by silica gel column chromatography (solvent;

chloroform/methanol) to give 4-methoxy-6'-hydroxy-2'-O-(4,6-O-benzylidene-β-D-glucopyranosyl)dihydrochalcone (2.65 g) as white powders.

M.p. 126°–130° C.

FABMS (m/s): 545 [(M+Na)$^+$]

NMR (DMSO-$d_6$) δ: 2.84 (2H, t, J=7.6 Hz), 3.19 (2H, t, J=7.6 Hz), 3.3–3.7 (5H, m), 3.72 (3H, s), 4.21 (1H, d, J=4.9 Hz), 5.16 (1H, d, J=7.8 Hz), 5.48 (1H, d, J=5.4 Hz), 5.59 (1H, d, J=5.4 Hz), 5.60 (1H, s), 6.57 (1H, d, J=7.8 Hz), 6.72 (1H, d, J=8.3 Hz), 6.84 (2H, ddd, J=2.0, 2.9, 8.8 Hz), 7.17 (2H, ddd, J=2.0, 2.7, 8.3 Hz), 7.25 (1H, t, J=8.3 Hz), 7.40 (5H, m), 10.85 (1H, s)

Examples 67–72

Using the corresponding starting compounds, the compounds listed in Table 9 are obtained in the same manner as in Example 66.

TABLE 9

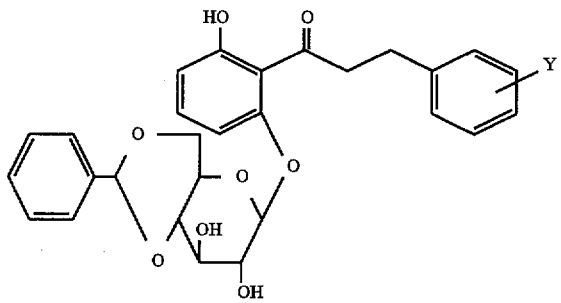

| Ex. No. | Y | Physical properties |
|---|---|---|
| 67 | H— | M.p. 135–136° C.<br>FABMS (m/z): 515 [(M+Na)$^+$]<br>NMR (DMSO-$d_6$) δ: 2.91 (2H, t, J = 7.4 Hz), 3.23 (2H, t, J = 7.4 Hz), 3.3–3.7 (5H, m), 4.21 (1H, dd, J = 3.2, 8.5 Hz), 5.17 (1H, d, J = 7.7 Hz), 5.48 (1H, d, J = 5.2 Hz), 5.59 (1H, d, J = 5.8 Hz), 5.60 (1H, s), 6.58 (1H, d, J = 8.2 Hz), 6.72 (1H, d, J = 8.5 Hz), 7.1–7.3 (5H, m), 7.25 (1H, t, J = 8.3 Hz), 7.3–7.5(5H, m), 10.83 (1H, s) |
| 68 | 4-OH— | FABMS (m/z): 531 [(M+Na)$^+$]<br>NMR (DMSO-$d_6$) δ: 2.78 (2H, t, J = 7.3 Hz), 3.16 (2H, t, J = 7.6 Hz), 3.3–3.7 (5H, m), 4.20 (1H, d, J = 4.9 Hz), 5.16 (1H, d, J = 7.8 Hz), 5.48 (1H, d, J = 4.9 Hz), 5.58 (1H, d, J = 4.9 Hz), 5.60 (1H, s), 6.57 (1H, d, J = 7.8 Hz), 6.67 (2H, d, J = 8.3 Hz), 6.71 (1H, d, J = 8.3 Hz), 7.04 (2H, d, J = 8.3 Hz), 7.25 (1H, t, J = 8.3 Hz), 7.36–7.49 (5H, m), 9.12 (1H, s), 10.87 (1H, s) |
| 69 | 4-CH$_3$ | FABMS (m/z): 529 [(M+Na)$^+$]<br>NMR (DMSO-$d_6$) δ: 2.26 (3H, s), 2.86 (2H, t, J = 7.6 Hz), 3.21 (2H, t, J = 7.3 Hz), 3.3–3.7 (5H, m), 4.21 (1H, d, J = 4.9 Hz), 5.16 (1H, d, J = 7.8 Hz), 5.48 (1H, d, J = 4.9 Hz), 5.58 (1H, d, J = 5.9 Hz), 5.60 (1H, s), 6.57 (1H, d, J = 8.3 Hz), 6.72 (1H, d, J = 7.8 Hz), 7.11 (4H, m), 7.25 (1H, t, J = 8.3 Hz), 7.36–7.49 (5H, m), 10.86 (1H, s) |
| 70 | 3-CH$_3$— | FABMS (m/z): 529 [(M+Na)$^+$]<br>NMR (DMSO-$d_6$) δ: 2.28 (3H, s), 2.87 (2H, t, J = 7.4 Hz), 3.22 (2H, t, J = 7.4 Hz), 3.3–3.7 (5H, m), 4.21 (1H, dd, J = 3.1, 8.3 Hz), 5.17 (1H, d, J = 7.8 Hz), 5.48 (1H, d, J = 5.2 Hz), 5.58 (1H, d, J = 5.7 Hz), 5.59 (1H, s), 6.58 (1H, d, J = 8.2 Hz), 6.72 (1H, d, J = 8.5 Hz), 7.0–7.1 (3H, m), 7.17 (1H, t, J = 7.4 Hz), 7.25 (1H, t, J = 8.3 Hz), 7.3–7.5 (5H, m), 10.83 (1H, s) |
| 71 | 4-Cl— | FABMS (m/z): 549/551 [(M+Na)$^+$]<br>NMR (DMSO-$d_6$) δ: 2.90 (2H, t, J = 7.3 Hz), 3.23 (2H, m), 3.30–3.72 (5H, m), 4.21 (1H, m), 5.16 (1H, d, J = 7.7 Hz), 5.49 (1H, d, J = 5.3 Hz), 5.60 (1H, s), 5.61 (1H, d, J = 5.6 Hz), 6.57 (1H, d, J = 8.3 Hz), 6.72 (1H, d, J = 8.5 Hz), 7.21–7.48 (10H, m), 10.82 (1H, s) |
| 72 | 4-CH$_3$CH$_2$—OCOO— | FABMS (m/z): 603 [(M+Na)$^+$]<br>NMR (DMSO-$d_6$) δ: 1.28 (3H, t, J = 7.1 Hz), 2.92 (2H, t, J = 7.4 Hz), 3.24 (2H, t, J = 7.1 Hz), 3.28–3.73 (5H, m), 4.21 (1H, m), 4.23 (2H, q, J = 7.1 Hz), 5.17 (1H, d, J = 7.9 Hz), 5.47 (1H, d, J = 5.3 Hz), 5.60 (1H, s), 5.61 (1H, d, J = 5.4 Hz), 6.57 (1H, d, J = 8.2 Hz), 6.72 (1H, d, J = 8.5 Hz), 7.13 (2H, ddd, J = 2.0, 2.8, 8.5 Hz), 7.25 (1H, t, J = 8.3 Hz), 7.31 (2H, ddd, J = 1.9, 2.6, 8.7 Hz), 7.35–7.48 (5H, m), 10.83 (1H, s) |

Example 73

(1) 4-Methoxy-6'-hydroxy-2'-O-(4,6-O-benzylidene-β-D-glucopyranosyl)dihydrochalcone (1.86 g) is dissolved in pyridine (40 ml), and thereto is added acetic anhydride (10 ml). The mixture is reacted at room temperature for three hours, and concentrated under reduced pressure. To the residue is added isopropyl ether, and the precipitated powders are collected by filtration, washed, and dried to give 4-methoxy-6'-acetoxy-2'-O-(2,3-di-O-acetyl-4,6-O-benzylidene-β-D-glucopyranosyl)dihydrochalcone (2.06 g) as white powders.

M.p. 175.5°–176.5° C.

FABMS (m/z): 649 (MH$^+$)

(2) To a 80% aqueous acetic acid solution (30 ml) is added the above obtained 4-methoxy-6'-acetoxy-2'-O-(2,3-di-O-acetyl-4,6-O-benzylidene-β-D-glucopyranosyl)dihydrochalcone (1.00 g), and the mixture is heated with stirring at 70° C. for two hours. The reaction solution is concentrated under reduced pressure, and the residue is purified by silica gel column chromatography (solvent; chloroform/methanol) to give 4-methoxy-6'-acetoxy- 2'-O-(2,3-di-O-acetyl-β-D-glucopyranosyl)dihydrochalcone (820 mg) as white amorphous powders.

FABMS (m/z): 583 [(M+Na)$^+$]

NMR (DMSO-d$_6$) δ: 1.89 (3H, s), 2.00 (3H, s), 2.06 (3H, s), 2.77 (2H, m), 2.88 (2H, m), 3.4–3.8 (4H, m), 3.71 (3H, s), 4.76 (1H, t, J=5.9 Hz), 4.88 (1H, dd, J=7.8, 9.8 Hz), 5.11 (1H, dd, J=9.3, 9.8 Hz), 5.50 (1H, d, J=7.8 Hz), 5.59 (1H, d, J=5.9 Hz), 6.84 (2H, ddd, J=2.0, 2.9, 8.3 Hz), 6.88 (1H, d, J=8.3 Hz), 7.13 (2H, ddd, J=2.0, 2.9, 8.3 Hz), 7.15 (1H, d, J=7.8 Hz), 7.44 (1H, t, J=8.3 Hz)

Example 74

(1) To a mixture of methanol-tetrahydrofuran (30 ml/100 ml) are added 4-methoxy-6'-acetoxy-2'-O-(2,3-di-O-acetyl-4,6-O-benzylidene-β-D-glucopyranosyl)dihydrochalcone (1.05 g) and sodium hydrogen carbonate (272 mg), and the mixture is stirred at room temperature for four hours, and then stirred at 40° C. for 30 minutes. The mixture is concentrated under reduced pressure, and to the residue are added ethyl acetate and water. The mixture is stirred and the organic layer is collected, washed with water, and dried. The mixture is filtered, and the filtrate is concentrated. To the residue is added isopropyl ether, and the precipitated white powders are collected by filtration, washed, and dried to give 4-methoxy-6'-hydroxy-2'-O-(2,3-di-O-acetyl-4,6-O-benzylidene-β-D-glucopyranosyl)dihydrochalcone (911 mg).

M.p. 149°–151° C.

FABMS (m/z): 607 (MH$^+$)

(2) The above obtained 4-methoxy-6'-hydroxy-2'-O-(2,3-di-O-acetyl-4,6-O-benzylidene-β-D-glucopyranosyl)dihydrochalcone (900 mg) is treated in the same manner as in Example 73-(2) to give 4-methoxy-6'-hydroxy-2'-O-(2,3-di-O-acetyl-β-D-glucopyranosyl)dihydrochalcone (640 mg) as white powders.

M.p. 136°–138° C.

FABMS (m/z): 541 [(M+Na)$^+$]

NMR (DMSO-d$_6$) δ: 1.93 (3H, s), 2.00 (3H, s), 2.76 (2H, m), 2.90 (2H, m), 3.4–3.8 (4H, m), 3.71 (3H, s), 4.73 (1H, t, J=5.6 Hz), 4.85 (1H, dd, J=7.8, 9.8 Hz), 5.09 (1H, dd, J=8.8, 9.8 Hz), 5.35 (1H, d, J=7.8 Hz), 5.56 (1H, d, J=5.4 Hz), 6.57 (1H, d, J=7.8 Hz), 6.67 (1H, d, J=8.3 Hz), 6.83 (2H, ddd, J=2.0, 2.9, 8.8 Hz), 7.13 (2H, ddd, J=2.4, 2.9, 8.8 Hz), 7.19 (1H, t, J=8.3 Hz), 10.26 (1H, s)

Example 75

(1) 4-Methoxy-6'-hydroxy-2'-O-(4,6-O-benzylidene-β-D-glucopyranosyl)dihydrochalcone (1.045 g) is dissolved in pyridine (20 ml), and thereto is added dropwise with stirring n-butyryl chloride (1.28 g) under ice-cooling. The mixture is reacted at room temperature for two hours, and concentrated under reduced pressure. To the residue are added ethyl acetate and ice-cold diluted hydrochloric acid. The mixture is stirred and the organic layer is collected, washed with water, filtered, and concentrated. To the residue are added methanol (20 ml) and sodium hydrogen carbonate (0.84 g), and the mixture is stirred at 40° C. for four hours. The mixture is concentrated, and to the residue are added ethyl acetate and water. The mixture is stirred and the organic layer is collected, dried, filtered, and concentrated. The residue is purified by silica gel column chromatography (solvent; ethyl acetate/n-hexane) to give 4-methoxy-6'-hydroxy-2'-O-(2,3-di-O-butyryl-4,6-O-benzylidene-β-D-glucopyranosyl)dihydrochalcone (0.80 g) as white powders.

FABMS (m/z): 662 (MH$^+$)

(2) The above obtained 4-methoxy-6'-hydroxy-2'-O-(2,3-di-O-butyryl-4,6-O-benzylidene-β-D-glucopyranosyl)dihydrochalcone (0.75 g) is added to a 80% aqueous acetic acid solution (50 ml), and the mixture is heated at 70° C. for two hours. The mixture is treated in the same manner as in Example 8-(2) to give 4-methoxy-6'-hydroxy-2'-O-(2,3-di-O-butyryl-β-D-glucopyranosyl)dihydrochalcone (0.54 g) as white powders.

M.p. 126°–127° C.

FABMS (m/z): 597 [(M+Na)]$^+$

NMR (DMSO-d$_6$) δ: 0.79 (3H, t, J=7.3 Hz), 0.87 (3H, t, J=7.3 Hz), 1.3–1.6 (4H, m), 2.1–2.3 (4H, m), 2.7–2.9 (4H, m), 3.5–3.7 (4H, m), 3.71 (3H, s), 4.73 (1H, t, J=5.9 Hz), 4.89 (1H, t, J=7.8 Hz), 5.12 (1H, d, J=8.8 Hz), 5.38 (1H, d, J=7.8 Hz), 5.53 (1H, d, J=5.9 Hz), 6.56 (1H, d, J=8.3 Hz), 6.67 (1H, d, J=8.3 Hz), 6.83 (2H, d, J=8.3 Hz), 7.13 (2H, d, J=8.3 Hz), 7.18 (1H, t, J=8.3 Hz), 10.26 (1H, s)

Examples 76–113

Using the corresponding starting compounds, the compounds listed in Tables 10–16 are obtained in the same manner as in Examples 73, 74 and 75.

TABLE 10

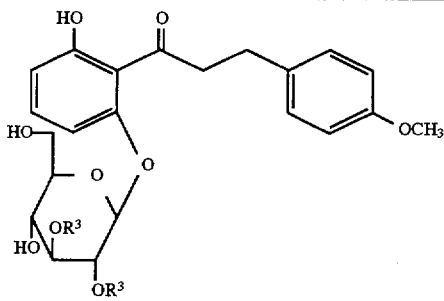

| Ex. No. | R³ | Physical properties |
|---|---|---|
| 76 | (CH₃)₂CHCO— | FABMS (m/z): 597 [(M+Na)⁺]<br>NMR (DMSO-d₆) δ: 0.9–1.1 (12H, m), 2.3–2.5 (2H, m), 2.8–3.0 (4H, m), 3.5–3.8 (4H, m), 3.71 (3H, s), 4.72 (1H, t, J = 8.0 Hz), 4.89 (1H, t, J = 7.8 Hz), 5.13 (1H, t, J = 8.8 Hz), 5.42 (1H, d, J = 7.8 Hz), 5.53 (1H, d, J = 5.9 Hz), 6.56 (1H, d, J = 5.9 Hz), 6.67 (1H, d, J = 8.3 Hz), 6.83 (2H, d, J = 8.8 Hz), 7.1–7.2 (3H, m), 10.26 (1H, s) |
| 77 | (phenyl)-CO— | FABMS (m/z): 665 [(M+Na)⁺]<br>NMR (DMSO-d₆) δ: 2.5–3.0 (4H, m), 3.60 (1H, m), 3.70 (3H, s), 3.78 (3H, m), 4.80 (1H, broad), 5.31 (1H, dd, J = 7.8, 9.8 Hz), 5.58 (1H, m), 5.70 (1H, d, J = 7.8 Hz), 5.72 (1H, broad), 6.54 (1H, d, J = 8.3 Hz), 6.74 (1H, d, J = 8.8 Hz), 6.75 (2H, d, J = 8.8 Hz), 6.95 (2H, d, J = 8.8 Hz), 7.20 (1H, t, J = 8.3 Hz), 7.40 (4H, m), 7.58 (2H, m), 7.77 (2H, dd, J = 1.5, 8.8 Hz), 7.87 (2H, dd, J = 1.5, 8.3 Hz), 10.26 (1H, s) |
| 78 | CH₃OCH₂CO— | M.p. 98–100° C.<br>FABMS (m/z): 601 [(M+Na)⁺]<br>NMR (DMSO-d₆) δ: 2.76 (2H,m), 2.93 (2H, m), 3.26 (3H, s), 3.29 (3H, s), 3.4–3.8 (4H, m), 3.71 (3H, s), 3.92 (2H, dd, J = 8.8, 17.1 Hz), 4.08 (2H, dd, J = 7.8, 16.6 Hz), 4.75 (1H, t, J = 5.6 Hz), 4.93 (1H, dd, J = 7.8, 9.8 Hz), 5.19 (1H, t, J = 9.8 Hz), 5.43 (1H, d, J = 8.3 Hz), 5.64 (1H, d, J = 5.4 Hz), 6.57 (1H, d, J = 8.3 Hz), 6.68 (1H, d, J = 8.3 Hz), 6.82 (2H, ddd, J = 2.0, 2.9, 8.8 Hz), 7.13 (2H, ddd, J = 2.0, 2.9, 8.3 Hz), 7.19 (1H, t, J = 8.3 Hz), 10.27 (1H, s) |
| 79 | CH₃CH₂OCH₂CO— | M.p. 96–99° C.<br>FABMS (m/z): 629 [(M+Na)⁺]<br>NMR (DMSO-d₆) δ: 1.07 (3H, t, J = 6.8 Hz), 1.12 (3H, t, J = 6.8 Hz), 2.76 (2H, m), 2.88 (2H, m), 3.44 (4H, m), 3.4–3.8 (4H, m), 3.71 (3H, s), 3.95 (2H, dd, J = 9.3, 16.6 Hz), 4.10 (2H, dd, J = 8.1, 16.8 Hz), 4.75 (1H, t, J = 5.4 Hz), 4.91 (1H, dd, J = 7.8, 9.8 Hz), 5.18 (1H, dd, J = 8.8, 9.8Hz), 5.42 (1H, d, J = 7.8 Hz), 5.63 (1H, d, J = 5.4 Hz), 6.57 (1H, d, J = 8.3 Hz), 6.68 (1H, d, J = 8.3 Hz), 6.82 (2H, ddd, J = 2.0, 2.9, 8.3 Hz), 7.13 (2H, ddd, J = 1.5, 2.9, 8.3 Hz), 7.19 (1H, t, J = 8.3 Hz), 10.27 (1H, s) |
| 80 | CH₃(CH₂)₂OCH₂CO— | M.p. 96–99° C.<br>FABMS (m/z): 657 [(M+Na)⁺]<br>NMR (DMSO-d₆) δ: 0.8–0.9 (6H, m), 1.4–1.5 (4H, m), 2.7–2.9 (4H, m), 3.3–3.4 (4H, m), 3.5–3.8 (4H, m), 3.71 (3H, s), 3.95 (2H, dd, J = 10.3, 16.6 Hz), 4.10 (2H, dd, J = 8.3, 16.6 Hz), 4.75 (1H, t, J = 5.9 Hz), 4.92 (1H, dd, J = 7.8, 9.8 Hz), 5.17 (1H, t, J = 9.8 Hz), 5.41 (1H, d, J = 7.8 Hz), 5.63 (1H, d, J = 5.4 Hz), 6.57 (1H, d, J = 8.3 Hz), 6.68 (1H, d, J = 8.3 Hz), 6.82 (2H, d, J = 8.3 Hz), 7.13 (2H, d, J = 8.8 Hz), 7.19 (1H, t, J = 8.3 Hz), 10.28 (1H, s) |
| 81 | (CH₃)₂CHOCH₂CO— | FABMS (m/z): 657 [(M+Na)⁺]<br>NMR (DMSO-d₆) δ: 1.0–1.1 (12H, m), 2.7–2.9 (4H, m), 3.4–3.8 (6H, m), 3.71 (3H, s), 3.93 |

TABLE 10-continued

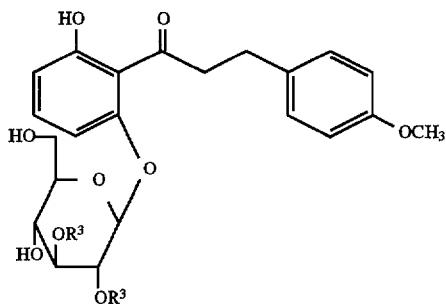

| Ex. No. | R³ | Physical properties |
|---|---|---|
| | | (2H, dd, J = 11.2, 17.1 Hz), 4.10 (2H, dd, J = 6.3, 16.9 Hz), 4.75 (1H, t, J = 5.4 Hz), 4.91 (1H, dd, J = 7.8, 9.8 Hz), 5.17 (1H, t, J = 8.8 Hz), 5.40 (1H, d, J = 7.8 Hz), 5.62 (1H, d, J = 5.4Hz), 6.57 (1H, d, J = 8.3 Hz), 6.68 (1H, d, J = 7.8 Hz), 6.82 (2H, d, J = 8.8 Hz), 7.13 (2H, d, J = 8.8 Hz), 7.19 (1H, t, J = 8.3 Hz), 10.28 (1H, s) |
| 82 | $(CH_3)_2CHCH_2OCH_2CO-$ | FABMS (m/z): 685 [(M+Na)⁺] NMR (DMSO-$d_6$) δ: 0.81 (6H, d, J = 6.8 Hz), 0.87 (6H, d, J = 6.9 Hz), 1.7–1.8 (2H, m), 2.7–2.9 (4H, m), 3.1–3.3 (4H, m), 3.5–3.7 (4H, m), 3.71 (3H, s), 3.96 (2H, dd, J = 10.8, 16.9 Hz), 4.11 (2H, dd, J = 7.3, 16.6 Hz), 4.75 (1H, t, J = 5.9 Hz), 4.92 (1H, dd, J = 7.8, 9.8 Hz), 5.17 (1H, t, J = 9.8 Hz), 5.40 (1H, d, J = 7.8 Hz), 5.63 (1H, d, J = 5.4 Hz), 6.57 (1H, d, J = 7.8 Hz), 6.68 (1H, d, J = 8.3 Hz), 6.82 (2H, d, J = 8.3 Hz), 7.13 (2H, d, J = 8.3 Hz), 7.19 (1H, t, J = 8.3 Hz), 10.23 (1H, s) |
| 83 | $CH_3O(CH_2)_2OCH_2CO-$ | M.p. 104–105° C. FABMS (m/z): 689 [(M+Na)⁺] NMR (DMSO-$d_6$) δ: 2.7–2.8 (2H, m), 2.9–3.0 (2H, m), 3.21 (3H, s), 3.25 (3H, s), 3.3–3.7 (12H, m), 3.71 (3H, s), 4.01 (2H, dd, J = 8.8, 17.1 Hz), 4.15 (2H, dd, J = 7.3, 17.1 Hz), 4.75 (1H, t, J = 5.9 Hz), 4.91 (1H, dd, J = 7.8, 9.8 Hz), 5.17 (1H, t, J = 9.8 Hz), 5.42 (1H, d, J = 8.3 Hz), 5.64 (1H, d, J = 5.4 Hz), 6.57 (1H, d, J = 7.8 Hz), 6.68 (1H, d, J = 8.3 Hz), 6.82 (2H, d, J = 8.8 Hz), 7.13 (2H, d, J = 8.3 Hz), 7.19 (1H, t, J = 8.3 Hz), 10.28 (1H, s) |
| 84 | $CH_3O(CH_2)_2CO-$ | M.p. 120.5–122° C. FABMS (m/z): 629 [(M+Na)⁺] NMR (DMSO-$d_6$) δ: 2.43 (2H, t, J = 6.9 Hz), 2.51 (2H, t, J = 6.6 Hz), 2.76 (2H, m), 2.93 (2H, m), 3.12 (3H, s), 3.21 (3H, s), 3.4–3.56 (6H, m), 3.63 (1H, m), 3.70 (1H, m), 3.71 (3H, s), 4.72 (1H, t, J = 5.6 Hz), 4.90 (1H, dd, J = 8.0, 9.9 Hz), 5.14 (1H, dd, J = 9.3, 9.6 Hz, 5.39 (1H, d, J = 8.0 Hz), 5.53 (1H, d, J = 5.8 Hz), 6.56 (1H, d, J = 8.0 Hz), 6.67 (1H, d, J = 8.2 Hz), 6.82 (2H, ddd, J = 2.1, 3.0, 8.7 Hz), 7.13 (2H, ddd, J = 2.0, 2.8, 8.7 Hz), 7.19 (1H, t, J = 8.3 Hz), 10.38 (1H, s) |
| 85 | $CH_3OCH(CH_3)CO-$ | FABMS (m/z): 629 [(M+Na)⁺] NMR (DMSO-$d_6$) δ: 1.1–1.3 (6H, m), 2.7–2.8 (2H, m), 2.9–3.0 (2H, m), 3.15–3.25 (6H, m), 3.5–3.6 (2H, m), 3.6–3.7 (2H, m), 3.71 (3H, s), 3.8–3.9 (2H, m), 4.74 (1H, brs), 4.97 (1H, t, J = 8.5 Hz), 5.22 (1H, t, J = 9.6 Hz), 5.5–5.6 (1H, m), 5.66 (1H, d, J = 6.1 Hz), 6.56 (1H, dd, J = 3.0, 8.2 Hz), 6.67 (1H, dd, J = 1.8, 8.3 Hz), 6.83 (2H, d, J = 8.7 Hz), 7.14 (1H, d, J = 7.7 Hz), 7: 16 (1H, t, J = 8.5 Hz), 7.20 (1H, t, J = 8.3 Hz), 10.31 (1H, s) |
| 86 | $CH_3OC(CH_3)_2CO-$ | FABMS (m/z): 657 [(M+Na)⁺] NMR (DMSO-$d_6$) δ: 1.21 (3H, s), 1.22 (3H, s), 1.29 (3H, s), 1.31 (3H, s), 2.79 (2H, t, J = 7.2 Hz), 2.96 (2H, t, J = 7.2 Hz), 3.04 (3H, s), 3.15 (3H, s), 3.5–3.6 (2H, m), 3.6–3.7 (2H, m), 3.72 (3H, s), 4.72 (1H, t, J = 5.5 Hz), 4.95 |

TABLE 10-continued

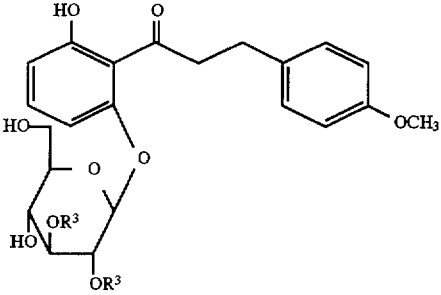

| Ex. No. | R³ | Physical properties |
|---|---|---|
| | | (1H, dd, J = 7.8. 9.6 Hz), 5.22 (1H, t, J = 9.3 Hz), 5.58 (1H, d, J = 6.7 Hz), 5.61 (1H, d, J = 7.8 Hz), 6.55 (1H, d, J = 8.3 Hz), 6.67 (1H, d, J = 8.6 Hz), 6.83 (2H, d, J = 8.6 Hz), 7.16 (2H, d, J = 8.6 Hz), 7.20 (1H, t, J = 8.4 Hz), 10.30 (1H, s) |
| 87 | CH₃CH₂OCO— | M.p. 117–119° C.<br>FABMS (m/z): 601 [(M+Na)⁺]<br>NMR (DMSO-d₆) δ: 1.15 (3H, t, J = 7.1 Hz), 1.20 (3H, t, J = 7.1 Hz), 2.76(2H, m), 2.91 (2H, m), 3.4–3.8 (4H, m), 3.71 (3H, s), 3.99–4.20 (4H, m), 4.68 (1H, dd, J = 7.8, 9.8 Hz), 4.74 (1H, t, J = 4.9 Hz), 4.94 (1H, dd, J = 8.8, 9.8 Hz), 5.43 (1H, d, J = 7.8 Hz), 5.72 (1H, d, J = 5.4 Hz), 6.57 (1.H, d, J = 8.3 Hz), 6.65 (1H, d, J = 8.3 Hz), 6.83 (2H, ddd, J = 2.0, 3.2, 8.3 Hz), 7.13 (2H, d, J = 8.3 Hz), 7.19 (1H, t,J = 8.3 Hz), 10.23 (1H, s) |
| 88 | (CH₃)₂CHCH₂OCO— | FABMS (m/z): 657 [(M+Na)⁺]<br>NMR (DMSO-d₆) δ: 0.80 (6H, dd, J = 2.0, 6.8 Hz), 0.87 (6H, d, J = 6: 8 Hz), 1.84 (2H, m), 2.79 (2H, m), 2.88 (2H, m), 3.4–3.75 (4H, m), 3.70 (3H, s), 3.75–3.95 (4H, m), 4.70 (1H, dd, J = 7.8, 9.8 Hz), 4.74 (1H, t, J = 5.6 Hz), 4.96 (1H, dd, J = 8.8, 9.3 Hz), 5.46 (1H, d, J = 7.8 Hz), 5.72 (1H, d, J = 5.9 Hz), 6.57 (1H, d, J = 8.3 Hz), 6.66 (1H, d, J = 8.3 H.z), 6.82 (2H, ddd, J = 2.0, 2.9, 8.3 Hz), 7.13 (2H, d, J = 8.3 Hz), 7.19 (1H, t, J = 8.3 Hz), 10.25 (1H, s) |
| 89 | 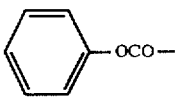 | FABMS (m/z): 697 [(M+Na)⁺]<br>NMR (DMSO-d₆) δ: 2.74 (2H, t, J = 7.3 Hz), 2.99 (2H, t, J = 7.3 Hz), 3.6–3.8 (4H, m), 3.68 (3H, s), 4.82 (1H, t, J = 5.9 Hz), 4.86 (1H, dd, J = 7.8, 9.3 Hz), 5.15 (1H, dd, J = 8.8, 9.3 Hz), 5.60 (1H, d, J = 7.8 Hz), 5.97 (1H, d, J = 4.9 Hz), 6.61 (1H, d, J = 8.3 Hz), 6.71 (1H, d, J = 8.3 Hz), 6.77 (2H, ddd, J = 2.0, 2.9, 8.8 Hz), 7.05 (2H, ddd, J = 2.0, 2.9, 8.3 Hz), 7.1–7.5 (11H, m), 10.25 (1H, s) |
| 90 | CH₃OCH₂CH₂OCO— | FABMS (m/z): 661 [(M+Na)⁺]<br>NMR (DMSO-d₆) δ: 2.7–2.8 (2H, m), 2.9–3.0 (2H, m), 3.21 (3H, s), 3.26 (3H, s), 3.4–3.5 (6H, m), 3.6–3.7 (2H, m), 3.71 (3H, s), 4.1–4.3 (4H, m), 4.70 (1H, dd, J = 8.0, 9.8 Hz), 4.74 (1H, t, J = 5.5 Hz), 4.96 (1H, t, J = 9.6 Hz), 5.44 (1H, d, J = 8.0 Hz), 5.74 (4H, d, J = 6.0 Hz), 6.57 (1H, d, J = 8.3 Hz), 6.65 (1H, d, J = 8.5 Hz), 6.83 (2H, dd, J = 2.0, 6.5 Hz), 7.14 (2H, d, J = 8.7 Hz), 7.19 (1H, t, J = 8.4 Hz), 10.28 (1H, s) |

TABLE 10-continued

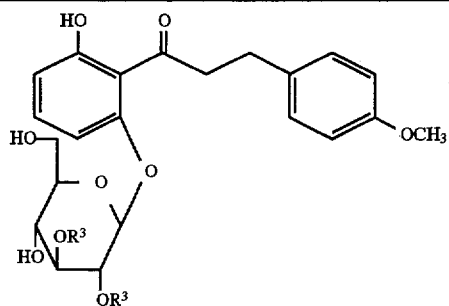

| Ex. No. | R³ | Physical properties |
|---|---|---|
| 91 | PhCH₂OCONHCH₂CO— | FABMS (m/z): 839 [(M+Na)⁺]<br>NMR (DMSO-d₆) δ: 2.78 (2H, t, J = 6.8 Hz), 2.98 (2H, t, J = 6.8 Hz), 3.4–4.0 (8H, m), 3.69 (3H, s), 4.73 (1H, t, J = 4.9 Hz), 4.92 (1H, dd, J = 7.8, 9.8 Hz), 4.98 (2H, s), 5.05 (2H, s), 5.18 (1H, dd, J = 8.8, 9.8 Hz), 5.44 (1H, d, J = 7.8 Hz), 5.59 (1H, d, J = 4.9 Hz), 6.57 (1H, d, J = 8.3 Hz), 6.69 (1H, d, J = 8.3 Hz), 6.80 (2H, ddd, J = 2.2, 2.9, 8.8 Hz), 7.14 (2H, d, J = 8.3 Hz), 7.21 (1H, t, J = 8.3 Hz), 7.30 (10H, m), 7.50 (2H, m), 10.57 (1H, broad) |
| 92 | CH₃SO₃H.NH₂CH₂CO— | FABMS(m/z): 571 [(M+Na)⁺]<br>NMR (DMSO-d₆) δ: 2.40 (6H, s), 2.81 (2H, t, J = 7.1 Hz), 3.02 (2H, t, J = 7.1 Hz), 3.4–3.5 (4H, m), 3.72 (3H s), 3.83 (4H, m), 4.30 (2H, broad), 4.96 (1H,dd, J = 8.3, 9.8 Hz), 5.28 (1H, dd, J = 8.8, 9.8 Hz), 5.45 (1H, d, J = 7.8 Hz), 6.61 (1H, d, J = 8.3 Hz), 6.70 (1H, d, J = 8.3 Hz), 6.83 (2H, d, J = 8.8 Hz), 7.16 (2H, d, J = 8.8 Hz), 7.23 (1H, t, J = 8.3 Hz), 8.30 (6H, broad), 10.46 (1H, broad) |
| 93 | HOOC(CH₂)₂CO— | FABMS (m/z): 657 [(M+Na)⁺]<br>IR (nujol) cm⁻¹: 3400, 3280, 1730, 1700, 1630 |
| 94 | CH₃CONHCH₂CO— | FABMS (m/z): 633 (MH)⁺<br>IR (nujol) cm⁻¹: 3300, 1760, 1660, 1630 |
| 95 | PhOCH₂CO— | FABMS (m/z): 725(MH⁺)<br>IR (nujol) cm⁻¹: 3400, 1770, 1630 |
| 96 | PhCH₂CO— | FABMS (m/z): 693(MH⁺)<br>R (nujol) cm⁻¹: 3460, 1750, 1720, 1630 |

TABLE 11

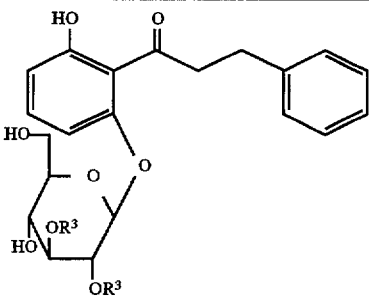

| Ex. No. | R³ | Physical properties |
|---|---|---|
| 97 | CH₃CO— | FABMS (m/z): 511 [(M+Na)⁺]<br>NMR (DMSO-d₆) δ: 1.91 (3H, s), 1.99 (3H, s), 2.8– |

TABLE 11-continued

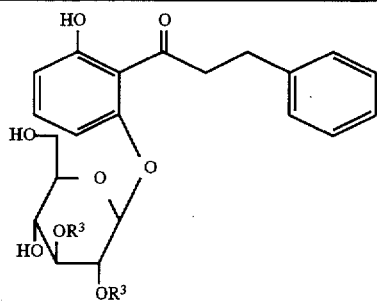

| Ex. No. | R³ | Physical properties |
|---|---|---|
| | | 3.0 (4H, m), 3.4–3.8 (4H, m), 4.73 (1H, t, J = 5.9 Hz), 4.86 (1H, dd, J = 8.31 9.8 Hz), 5.09 (1H, t, J = 9.8 Hz), 5.36 (1H, d, J = 7: 8 Hz), 5.56 (1H, t, J = 5.4 Hz), 6.57 (1H, d, J = 8.3 Hz), 6.67 (1H, d, J = 8.3 Hz), 7.1–7.3 (6H, m), 10.26 (1H, s) |
| 98 | $CH_3OCH_2CO-$ | M.p. 100–102° C. FABMS (m/z): 571 [(M+Na)⁺] NMR (DMSO-$d_6$) δ: 2.8–3.0 (4H, m), 3.26 (3H, s), 3.29 (3H, s), 3.5–3.7 (4H, m), 3.92 (2H, dd, J = 9.3, 16.6 Hz), 4.08 (2H, dd, J = 9.3, 16.6 Hz), 4.75 (1H, t, J = 5.8 Hz), 4.93 (1H, dd, J = 8.3, 9.8 Hz), 5.19 (1H, 1, J = 9.8 Hz), 5.43 (1H, d, J = 7.8 Hz), 5.64 (1H, t, J = 4.9 Hz), 6.57 (1H, d, J = 7.8 Hz), 6.68 (1H, t, J = 8.3 Hz), 7.1–7.3 (6H, m), 10.27 (1H, s) |

TABLE 12

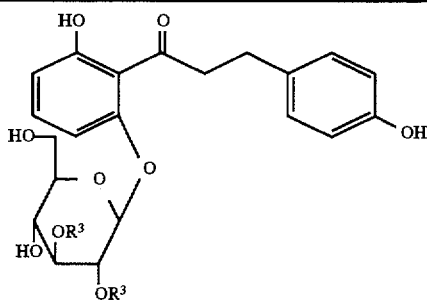

| Ex. No. | R³ | Physical properties |
|---|---|---|
| 99 | $CH_3OCH_2CO-$ | FABMS (m/z): 587 [(M+Na)⁺] NMR (DMSO-$d_6$) δ: 2.70 (2H, m), 2.89 (2H, m), 3.26 (3H, s), 3.29 (3H, s), 3.4–3.8 (4H, m), 3.92 (2H, dd, J = 9.8, 16.6 Hz), 4.07 (2H, dd, J = 9.0, 16.8 Hz), 4.75 (1H, t, J = 5.4 Hz), 4.93 (1H, dd, J = 8.1, 9.5 Hz), 5.19 (1H, dd, J = 8.8, 9.8 Hz), 5.43 (1H, d, J = 7.8 Hz), 5.64 (1H, d, J = 5.4 Hz), 6.57 (1H, d, J = 7.8 Hz), 6.65 (1H, d, J = 8.3 Hz), 6.68 (1H, d, J = 8.3 Hz), 7.00 (2H, d, J = 8.3 Hz), 7.19 (1H, t J = 8.3 Hz), 9.11 (1H, s), 10.26 (1H, s) |
| 100 | $CH_3CH_2OCH_2CO-$ | M.p. 111–114.5° C. FABMS (m/z): 615 [(M+Na)⁺] NMR (DMSO-$d_6$) δ: 1.07 (3H, t, J = 6.8 Hz), 1.12 (3H, 1, J = 6.8 Hz), 2.70 (2H, m), 2.90 (2H, m), 3.3–3.8 (8H, m), 3.95 (2H, dd, J = 10.0, 16.8 Hz), 4.10 (2H, dd, J = 8.8, 16.6 Hz), 4.75 (1H, t, J = 5.6 Hz), 4.91 (1H, dd, J = 8.1, 9.5 Hz), 5.18 (1H, dd, J = 8.8, 9.3 Hz), 5.42 (1H, d, J = 7.8 Hz), 5.63 (1H, d, J = 5.4 Hz), 6.57 (1H, d, J = 7.8 Hz), 6.65 (2H, d, J = 8.3 Hz), 6.68 (1H, d, J = 8.3 Hz), 7.00 (2H, d, J = 8.3 Hz), 7.1 9 (1H, 1, J = 8.3 Hz), 9.11 (1H, s), 10.27 (1H, s) |
| 101 | $CH_3CO-$ | M.p. 141.5–143° C. |

TABLE 12-continued

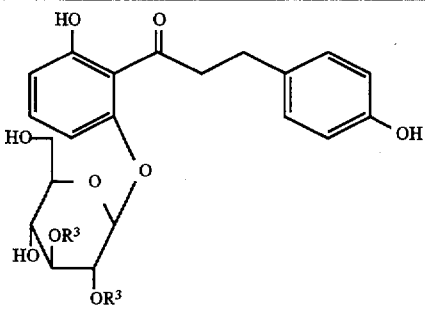

| Ex. No. | $R^3$ | Physical properties |
|---|---|---|
| 102 | $CH_3CH_2OCO-$ | FABMS (m/z): 527 [(M+Na)$^+$]<br>IR (nujol) cm$^{-1}$: 3440, 3240, 1750, 1630<br>M.p. 145–147.5° C.<br>FABMS (m/z): 587 [(M+Na)$^+$]<br>IR (nujol) cm$^{-1}$: 3400, 3280, 1770, 1750, 1630 |

TABLE 13

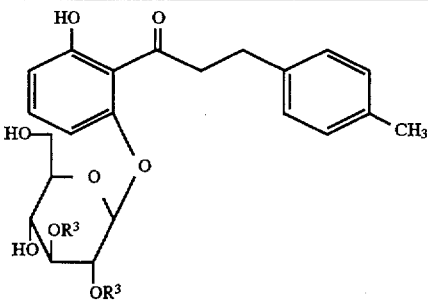

| Ex. No. | $R^3$ | Physical properties |
|---|---|---|
| 103 | $CH_3CO-$ | M.p. 84–87° C.<br>FABMS (m/z): 525 [(M+Na)$^+$]<br>NMR (DMSO-d$_6$) δ: 1.91 (3H, s), 2.00 (3H, s), 2.25 (3H, s), 2.78 (2H, m), 2.89 (2H, m), 3.4–3.75 (4H, m), 4.73 (1H, t, J = 5.6 Hz), 4.85 (1H, dd, J = 7.8, 9.8 Hz), 5.09 (1H, dd, J = 8.8, 9.8 Hz), 5.35 (1H, d, J = 7.8 Hz), 5.56 (1H, d, J = 5.4 Hz), 6.57 (1H, d, J = 8.3 Hz), 6.67 (1H, d, J = 8.3 Hz), 7.06 (2H, d, J = 8.8 Hz), 7.11 (2H, d, J = 8.8 Hz), 7.18 (1H, t, J = 8.3 Hz), 10.26 (1H, s) |
| 104 | $CH_3OCH_2CO-$ | FABMS (m/z): 585 [(M+Na)$^+$]<br>NMR (DMSO-d$_6$) δ: 2.25 (3H, s), 2.77 (2H, m), 2.93 (2H, m), 3.26 (3H, s), 3.29 (3H, s), 3.4–3.8 (4H, m), 3.92 (2H, dd, J = 9.5, 16.9 Hz), 4.07 (2H, dd, J = 8.0, 16.9 Hz), 4.75 (1H, t, J = 5.4 Hz), 4.92 (1H, dd, J = 7.8, 9.8 Hz), 5.19 (1H, dd, J = 8.8, 9.8 Hz), 5.43 (1H, d, J = 8.3 Hz), 5.64 (1H, d, J = 4.9 Hz), 6.57 (1H, d, J = 8.3 Hz), 6.68 (1H, d, J = 8.3 Hz), 7.06 (2H, dd, J = 2.4, 8.8 Hz), 7.11 (2H, dd, J = 2.9, 8.8 Hz), 7.19 (1H, t, J = 8.3 Hz), 10.27 (1H, s) |

TABLE 14

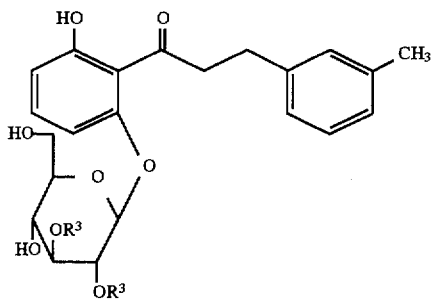

| Ex. No. | R³ | Physical properties |
|---|---|---|
| 105 | CH₃CH₂OCH₂CO— | M.p. 106–107° C.<br>FABMS (m/z): 525 [(M+Na)⁺]<br>NMR (DMSO-d₆) δ: 1.91 (3H, s), 1.99 (3H, s), 2.27 (3H, s), 2.7–2.8 (2H, m), 2.9–3.0 (2H, m), 3.4–3.5 (2H, m), 3.6–3.8 (2H, m), 4.72 (1H, t, J = 5.8 Hz), 4.86 (1H, dd, J = 8.0, 10.0 Hz), 5.09 (1H, t, J = 9.4 Hz), 5.34 (1H, d, J = 8.0 Hz), 5.56 (1H, d, J = 5.6 Hz), 6.57 (1H, d, J = 8.1 Hz), 6.68 (1H, d, J = 8.2 Hz), 6.9–7.0 (3H, m), 7.15 (1H, t, J = 7.5 Hz), 7.19 (1H, t, J = 8.3 Hz), 10.30 (1H, s) |
| 106 | CH₃CH₂OCH₂CO— | FABMS (m/z): 613 [(M+Na)⁺]<br>NMR (DMSO-d₆) δ: 1.07 (3H, t, J = 7.0 Hz), 1.12 (3H, t, J = 7.0 Hz), 2.27 (3H, s), 2.7–2.8 (2H, m), 2.9–3.0 (2H, m), 3.4–3.6 (6H, m), 3.6–3.7 (2H, m), 3.95 (2H, dd, J = 15.0, 16.8 Hz), 4.09 (2H, dd, J = 11.5, 16.8 Hz), 4.75 (1H, t, J = 5.5 Hz), 4.92 (1H, dd, J = 8.0, 9.7 Hz), 5.18 (1H, t, J = 9.3 Hz), 5.42 (1H, d, J = 7.9 Hz), 5.63 (1H, d, J = 5.5 Hz), 6.58 (1H, d, J = 8.2 Hz), 6.69 (1H, d, J = 8.4 Hz), 6.98 (1H, d, J = 7.8 Hz), 7.0–7.1 (2H, m), 7.15 (1H, t, J = 7.4 Hz), 7.19 (1H, t, J = 8.3 Hz), 10.30 (1H, s) |

TABLE 15

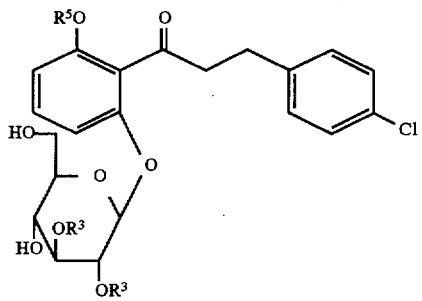

| Ex. No. | R³ | R⁵ | Physical properties |
|---|---|---|---|
| 107 | CH₃CO— | CH₃CO— | FABMS (m/z): 587/589 [(M+Na)⁺]<br>NMR (DMSO-d₆) δ: 1.90 (3H, s), 2.00 (3H, s), 2.05 (3H, s), 2.82 (2H, m), 2.98 (2H, m), 3.47–3.77 (4H, m), 4.75 (1H, t, J = 5.7 Hz), 4.88 (1H, dd, J = 7.9, 9.9 Hz), 5.12 (1H, dd, J = 9.3, 9.6 Hz), 5.51 (1H, d, J = 8.0 Hz), 5.59 (1H, d, J = 5: 6 Hz), 6.88 (1H, d, J = 8.1 Hz), 7.16 (1H, d, J = 8.1 Hz), 7.26 (2H, ddd, J = 2.1, 2.2, 8.7 Hz), 7.34 (2H, ddd, J = 2.1, 2.3, 8.6 Hz), 7.45 (1H, t, J = 8.3 Hz) |
| 108 | CH₃CO— | H— | M.p. 119–120.5° C.<br>FABMS (m/z): 545/547 [(M+Na)⁺]<br>NMR (DMSO-d₆) δ: 1.92 (3H, s), 2.00 (3H, s), 2.83 (2H, m), 2.95 (2H, m), 3.45– |

TABLE 15-continued

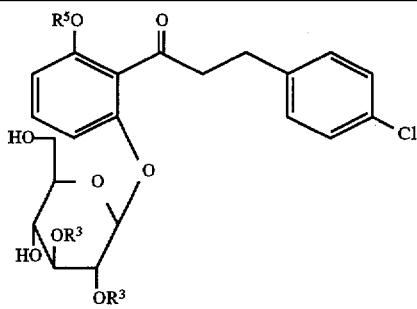

| Ex. No. | R³ | R⁵ | Physical properties |
|---|---|---|---|
| | | | 3.76 (4H, m), 4.73 (1H, t, J = 5.6 Hz), 4.85 (1H, dd, J = 8.0, 9.8 Hz), 5.09 (1H, t, J = 9.4 Hz), 5.36 (1H, d, J = 8.0 Hz), 5.55 (1H, d, J = 5.6 Hz), 6.57 (1H, d, J = 8.2 Hz), 6.68 (1H, d, J = 8.5 Hz), 7.19 (1H, t, J = 8.3 Hz), 7.26 (2H, dd, J = 2.2, 8.6 Hz), 7.32 (2H, ddd, J = 2.1, 2.2, 8.6 Hz), 10.28 (1H, s) |
| 109 | CH₃OCH₂CO— | H— | FABMS (m/z): 605/607 [(M+Na)⁺] NMR (DMSO-d₆) δ: 2.82 (2H, m), 2.97 (2H, m), 3.26 (3H, s), 3.29 (3H, s), 3.47–3.77 (4H, m), 3.93 (2H, dd, J = 14.1, 16.9 Hz), 4.07 (2H, dd, J = 8.7, 16.9 Hz), 4.75 (1H, t, J = 5.6 Hz), 4.92 (1H, dd, J = 8.0, 9.8 Hz), 5.19 (1H, t, J = 9.3 Hz), 5.43 (1H, d, J = 8.0 Hz), 5.64 (1H, d, J = 5.5 Hz), 6.57 (1H, d, J = 8.2 Hz), 6.68 (1H, d, J = 8.2 Hz), 7.19 (1H, t, J = 8.3 Hz), 7.26 (2H, ddd, J = 2.1, 2.4, 8.7 Hz), 7.31 (2H, ddd, J = 2.0, 2.2, 8.7 Hz), 10.29 (1H, s) |

TABLE 16

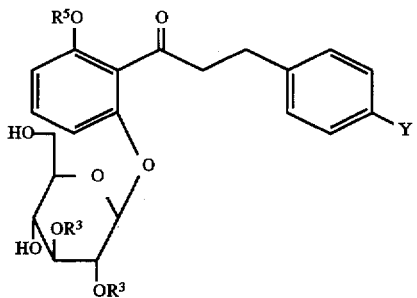

| Ex. No. | Y, R³, R⁵ | Physical properties |
|---|---|---|
| 110 | Y: CH₃COO— R³: CH₃CO— R⁵: H— | M.p. 127–129° C. FABMS (m/z): 569 [(M+Na)⁺] NMR (DMSO-d₆) δ: 1.91 (3H, s), 1.99 (3H, s), 2.24 (3H, s), 2.85 (2H, m), 2.95 (2H, m), 3.4–3.8 (4H, m), 4.73 (1H, t, J = 5.4 Hz), 4.86 (1H, dd, J = 8.3, 9.8 Hz), 5.09 (1H, dd, J = 8.8, 9.8 Hz), 5.36 (1H, d, J = 7.8 Hz), 5.56 (1H, d, J = 5.4 Hz), 6.57 (1H, d, J = 7.8 Hz), 6.67 (1H, d, J = 8.3 Hz), 7.01 (2H, ddd, J = 1.7, 2.7, 8.3 Hz), 7.19 (1H, t, J = 8.3 Hz), 7.26 (2H, dd, J = 2.0, 8.3 Hz), 10.27 (1H, s) |
| 111 | Y: CH₃CH₂OCOO— R³: CH₃CO— R⁵: H— | FABMS (m/z): 599 [(M+Na)⁺] NMR (DMSO-d₆) δ: 1.28 (3H, t, J = 7.1 Hz), 1.91 (3H, s), 1.99 (3H, s), 2.85 (2H, m), 2.96 (2H, m), 3.4–3.8 (4H, m), 4.23 (2H, q, J = 7.1 Hz), 4.73 (1H, t, J = 5.4 Hz), 4.86 (1H, dd, J = 7.8, 9.8 Hz), 5.09 (1H, dd, J = 8.8, 9.8 Hz), 5.36 (1H, d, J = 7.8 Hz), 5.56 (1H, d, J = 5.4 Hz), |

TABLE 16-continued

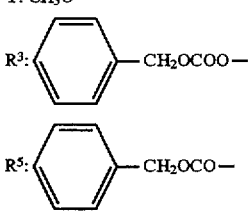

| Ex. No. | Y, R³, R⁵ | Physical properties |
|---|---|---|
| 112 | Y: CH₃CH₂OCOO—<br>R³: CH₃OCH₂CO—<br>R⁵: H— | 6.57 (1H, d, J = 8.3 Hz), 6.67 (1H, d, J = 8.3 Hz), 7.11 (2H, d, J = 8.3 Hz), 7.19 (1H, t, J = 8.3 Hz), 7.28 (2H, d, J = 8.3 Hz), 10.27 (1H, s)<br>FABMS (m/z): 659 [(M+Na)⁺]<br>NMR (DMSO-d₆) δ: 1.28 (3H, t, J = 7.1 Hz), 2.84 (2H, m), 2.98 (2H, m), 3.26 (3H, s), 3.29 (3H, s), 3.4–3.8 (4H, m), 3.92 (2H, dd, J = 9.5, 16.8 Hz), 4.08 (2H, dd, J = 5.9, 16.6 Hz), 4.23 (2H, q, J = 7.1 Hz), 4.75 (1H, t, J = 5.6 Hz), 4.93 (1H, dd, J = 7.8, 9.8 Hz), 5.19 (1H, dd, J = 8.8, 9.8 Hz), 5.43 (1H, d, J = 7.8 Hz), 5.64 (1H, d, J = 4.9 Hz), 6.57 (1H, ddd, J = 8.3 Hz), 6.68 (1H, d, J = 8.3 Hz), 7.11 (2H, ddd, J = 2.0, 2.7, 8.3 Hz), 7.19 (1H, t, J = 8.3 Hz), 7.27 (2H, dd, J = 2.0, 8.8 Hz), 10.28 (1H, s) |
| 113 | Y: CH₃O—<br>R³: 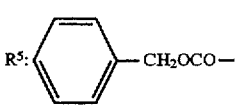 | FABMS (m/z): 859 [(M+Na)⁺]<br>NMR (DMSO-d₆) δ: 2.7–3.1 (4H, m), 3.5–3.8 (4H, m), 3.65 (3H, s), 4.77 (1H, t, J = 5.2 Hz), 4.78 (1H, dd, J = 7.9, 9.8 Hz), 5.0–5.2 (5H, m), 5.23 (2H, s), 5.64 (1H, d, J = 7.8 Hz), 5.80 (1H, d, J = 6.0 Hz), 6.78 (2H, dd, J = 2.2, 8.8 Hz), 7.06 (1H, d, J = 8.4 Hz), 7.09 (2H, d, J = 8.8 Hz), 7.18 (1H, d, J = 8.4 Hz), 7.25–7.43 (15H, m), 7.49 (1H, t, J = 8.3 Hz) |

Examples 114

(1) Using 4-methoxy-6'-hydroxy-2'-O-(4,6-O-benzylidene-β-D-glucopyranosyl)dihydrochalcone (1.5 g) and benzyloxyacetic chloride (2.0 g), there is obtained 4-methoxy-6'-hydroxy-2'-O-(2,3-di-O-benzyloxyacetyl-4,6-O-benzylidene-β-D-glucopyranosyl)dihydrochalcone (0.90 g) as white powders in the same manner as in Example 75-(1).

(2) The above obtained 4-methoxy-6'-hydroxy-2'-O-(2,3-di-O-benzyloxyacetyl-4,6-O-benzylidene-β-D-glucopyranosyl)dihydrochalcone (0.90 g) is dissolved in a mixture of ethanol (20 ml) and acetic acid (20 ml), and thereto is added 10% palladium-carbon (0.4 g). The mixture is subjected to catalytic hydrogenation with stirring under atmospheric pressure overnight. The mixture is filtered, and the filtrate is concentrated. The residue is purified by silica gel column chromatography (solvent; chloroform/methanol) to give 4-methoxy- 6'-hydroxy-2'-O-(2,3-di-O-hydroxyacetyl-β-D-glucopyranosyl)dihydrochalcone (460 mg) as white powders. The physical properties of this compound are shown in Table 17.

Example 115

4-Methoxy-6'-hydroxy-2'-O-β-D-glucopyranosyldihydrochalcone (1.30 g) is dissolved in pyridine (13 ml), and thereto is added dropwise with stirring benzoyl chloride (0.90 g) under ice-cooling over a period of 30 minutes. The mixture is stirred under ice-cooling for two hours, and poured into ice-water. The mixture is extracted with ethyl acetate, and the organic layer is washed with water, dried, filtered, and concentrated. The residue is purified by silica gel column chromatography (solvent; chloroform/methanol) to give 4-methoxy-6'-hydroxy-2'-O-(6-O-benzoyl-β-D-glucopyranosyl)dihydrochalcone (0.80 g) as colorless amorphous powders. The physical properties of this compound are shown in Table 17.

TABLE 17

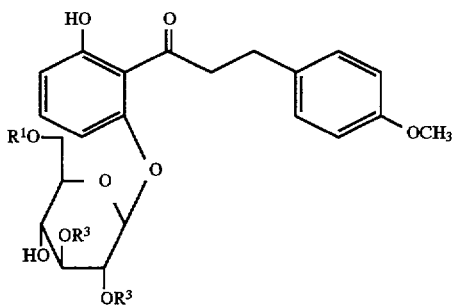

| Ex. No. | R$^1$ | R$^3$ | Physical properties |
|---|---|---|---|
| 114 | H— | HOCH$_2$CO— | M.p. 132–134° C.<br>FABMS (m/z): 573 [(M+Na)$^+$]<br>NMR (DMSO-d$_6$) δ: 2.7–2.8 (2H, m), 2.9–3.0 (2H, m), 3.4–3.5 (2H, m), 3.6–3.7 (2H, m), 3.71 (3H, s), 3.90 (2H, ddd, J = 5.7, 10.5, 16.9Hz), 4.94 (2H, ddd, J = 6.7, 11.1, 17.5 Hz), 4.73 (1H, t, J = 5.7 Hz), 4.89 (1H, dd, J = 8.0, 9.0 Hz), 5.15 (1H, t, J = 8.5 Hz), 5.4–5.5 (3H, m), 5.60 (1H, d, J = 5.6 Hz), 6.57 (1H, d, J = 8.2 Hz), 6.69 (1H, d, J = 8.3 Hz), 6.82 (2H, dd, J = 2.1, 8.7 Hz), 7.15 (2H, dd, J = 2.1, 8.7 Hz), 7.20 (1H, t, J = 8.3 Hz), 10.38 (1H, s) |
| 115 | ⟨phenyl⟩—CO— | H— | FABMS (m/z): 561 [(M+Na)$^+$]<br>NMR (DMSO-d$_6$) δ: 2.7–2.8 (2H, m), 3.1–3.4 (5H, m), 3.70 (3H, s), 3.6–3.8 (1H, m), 4.27 (1H, dd, J = 7.3, 11.7 Hz), 4.60 (1H, d, J = 10.3 Hz), 5.01 (1H, d, J = 6.8 Hz), 5.26 (1H, d, J = 4.4 Hz), 5.36 (1H, d, J = 4.9 Hz), 5.40 (1H, d, J = 4.9 Hz), 6.52 (1H, d, J = 8.3 Hz), 6.68 (1H, d, J = 8.3 Hz), 6.79 (2H, d, J = 8.8 Hz), 7.0–7.1 (1H, m), 7.13 (2H, d, J = 8.8 Hz), 7.5–7.7 (3H, m), 7.95 (2H, dd, J = 1.5, 6.8 Hz), 10.86 (1H, s) |

Example 116

4-Methoxy-6'-hydroxy-2'-O-β-D-glucopyranosyldihydrochalcone (1.0 g) is dissolved in pyridine (20 ml), and thereto is added acetic anhydride (5 ml). The mixture is stirred at room temperature for two days, and concentrated. To the residue are added ethyl acetate and diluted hydrochloric acid, and the mixture is stirred. The organic layer is collected, washed with water, dried, filtered, and concentrated. The residue is purified by silica gel column chromatography (solvent; chloroform/ethyl acetate) to give 4-methoxy-6'-acetoxy-2'-O-(2,3,4,6-tetra-O-acetyl-β-D-glucopyranosyl)dihydrochalcone (1.21 g) as white powders. The physical properties of this compound are shown in Table 18.

Example 117

4-Methoxy-6'-hydroxy-2'-O-β-D-glucopyranosyldihydrochalcone (869 mg) is dissolved in pyridine (10 ml), and thereto is added dropwise with stirring methoxyacetic chloride (1.30 g) under ice-cooling. The mixture is reacted at room temperature for two hours, and concentrated under reduced pressure. To the residue are added ethyl acetate and ice-cold diluted hydrochloric acid, and the mixture is stirred. The organic layer is collected, washed with water, dried, filtered, and concentrated. The residue is dissolved in methanol (20 ml), and thereto is added sodium hydrogen carbonate (840 mg). The mixture is stirred at room temperature for 30 minutes, and thereto is added ethyl acetate (100 ml). The insoluble materials are removed by filtration, and the filtrate is washed with water, dried, filtered, and concentrated. The residue is purified by silica gel column chromatography (solvent; chloroform/methanol) to give 4-methoxy-6'-hydroxy-2'-O-(2,3,4,6-tetra-O-methoxyacetyl-β-D-glucopyranosyl)dihydrochalcone (882 mg) as pale yellow oil. The physical properties of this compound are shown in Table 18.

TABLE 18

| Ex. No. | R¹, R², R³, R⁵ | Physical properties |
|---|---|---|
| 116 | R¹, R², R³: CH₃CO—<br>R⁵: CH₃CO— | M.p. 60–63° C.<br>FABMS (m/z): 667 [(M+Na)⁺]<br>NMR (DMSO-d₆) δ: 1.94 (3H, s), 1.97 (3H, s), 2.01 (6H, s), 2.06 (3H, s), 2.75 (2H, m), 2.89 (2H, m), 3.71 (3H, s), 4.06–4.31 (3H, m), 5.01 (1H, dd, J = 9.3, 9.8 Hz), 5.06 (1H, dd, J = 8.2, 9.8 Hz), 5.41 (1H, dd, J = 9.3, 9.8 Hz), 5.63 (1H, d, J = 7.8 Hz), 6.84 (2H, ddd, J = 2.0, 2.9, 8.8 Hz), 6.93 (1H, d, J = 8.3 Hz), 7.10 (1H, d, J = 7.8 Hz), 7.14 (2H, d, J = 8.7 Hz), 7.48 (1H, t, H = 8.3 Hz) |
| 117 | R¹, R², R³: CH₃OCH₂CO—<br>R⁵: H— | FABMS (m/z): 745 [(M+Na)⁺]<br>NMR (DMSO-d₆) δ: 2.6–3.1 (4H, m), 3.25 (3H, s), 3.27 (3H, s), 3.28 (6H, s), 3.32 (3H, s), 3.25–3.9 (9H, m), 4.33 (2H, m), 5.11 (2H, m), 5.53 (1H, dd, J = 9.3, 9.8 Hz), 5.58 (1H, d, J = 7.8 Hz), 6.60 (1H, d, J = 7.8 Hz), 6.62 (1H, d, J = 8.3 Hz), 6.83 (2H, d, J = 8.8 Hz), 7.13 (2H, d, J = 8.8 Hz), 7.21 (1H, t, J = 8.3 Hz), 10.25 (1H, s) |

Example 118

Using 4,6'-dimethoxy-2'-O-β-D-glucopyranosyldihydrochalcone, there is obtained 4,6'-dimethoxy-2'-O-(4,6-O-benzylidene-β-D-glucopyranosyl)dihydrochalcone in the same manner as in Example 66.

FABMS (m/z): 559 [(M+Na)⁺]

NMR (DMSO-d₆) δ: 2.81 (2H, t, J=8.3 Hz), 2.9–3.8 (7H, m), 3.71 5 (3H, s), 3.721 (3H, s), 4.19 (1H, dd, J=3.4, 8.6 Hz), 5.14 (1H, d, J=7.7 Hz), 5.45 (1H, d, J=5.3 Hz), 5.55 (1H, d, J=4.9 Hz), 5.58 (1H, s), 6.76 (1H, d, J=8.4 Hz), 6.84 (2H, ddd, J=2.0, 3.0, 8.6 Hz), 6.86 (1H, d, J=8.4 Hz), 7.15 (2H, dd, J=2.1, 8.7 Hz), 7.32 (1H, t, J=8.4 Hz), 7.4–7.5 (5H, m)

Examples 119–120

Using 4,6'-dimethoxy-2'-O-(4,6-O-benzylidene-β-D-glucopyranosyl)dihydrochalcone, the compounds listed in Table 19 are obtained in the same manner as in Examples 73-(1) and 74 or Example 75.

TABLE 19

| Ex. No. | R³, R⁵ | Physical properties |
|---|---|---|
| 119 | R³: CH₃CO—<br>R⁵: CH₃— | NMR (DMSO-d₆) δ: 1.91 (3H, s), 2.00 (3H, s), 2.7–3.0 (4H; m), 3.5–3.7 (4H, m), 3.71 (3H, s), 3.72 (3H, s), 4.74 (1H, t, J = 5.8 Hz), 4.84 (1H, dd, J = 8.0, 9.9 Hz), 5.08 (1H, dd, J = 9.3, 9.6 Hz), 5.34 (1H, d, |

TABLE 19-continued

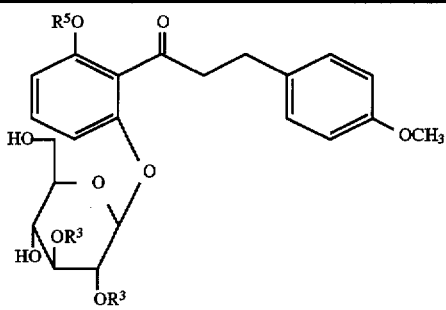

| Ex. No. | $R^3$, $R^5$ | Physical properties |
|---|---|---|
| 120 | $R^3$: $CH_3OCH_2CO-$<br>$R^5$: $CH_3-$ | J = 8.0 Hz), 5.56 (1H, d, J = 5.6 Hz), 6.77 (1H, d, J = 8.3 Hz), 6.83 (2H, dd, J = 2.1, 8.7 Hz), 6.84 (1H, d, J = 8.5 Hz), 7.13 (2H, ddd, J = 2.1, 2.9, 8.7 Hz), 7.32 (1H, t, J = 8.4 Hz)<br>FABMS (m/z): 555 [(M+Na)$^+$]<br>NMR (DMSO-d$_6$) δ: 2.75 (2H, m), 2.84 (2H, m), 3.27 (3H, s), 3.29 (3H, s), 3.4–3.8 (4H, m), 3.71 (6H, s), 3.93 (2H, dd, J = 14.2, 16.9 Hz), 4.06 (2H, dd, J = 14.8, 16.8 Hz), 4.76 (1H, t, J = 5.7 Hz), 4.91 (1H, dd, J = 8.0, 9.9 Hz), 5.19 (1H, dd, J = 9.2, 9.6 Hz), 5.42 (1H, d, J = 8.0 Hz), 5.64 (1H, d, J = 5.5 Hz), 6.78 (1H, d, J = 8.3 Hz), 6.83 (2H, ddd, J = 2.2, 3.0, 8.8 Hz), 6.85 (1H, d, J = 8.2 Hz), 7.12 (2H, ddd, J = 2.0, 2.9, 8.7 Hz), 7.33 (1H, t, J = 8.4 Hz)<br>FABMS (m/z): 615 [(M+Na)$^+$] |

Example 121

The compound obtained in Example 113 (569 mg) is dissolved in pyridine (5 ml), and thereto is added acetic anhydride (278 mg). The mixture is stirred at room temperature for two hours, and concentrated under reduced pressure. To the residue is added ethyl acetate, and the organic layer is washed with water, dried, and evaporated to remove the solvent. The residue is dissolved in a mixture of ethanol-ethyl acetate (5 ml/5 ml), and the mixture is subjected to catalytic hydrogenation under atmospheric pressure by using 10% palladium-carbon. The catalyst is removed by filtration, and the filtrate is evaporated to remove the solvent. The residue is purified by silica gel column chromatography (solvent; chloroform/methanol) to give 4-methoxy-6'-hydroxy-2'-O-(4,6-di-O-acetyl-β-D-glucopyranosyl)dihydrochalcone (251 mg).

M.p. 108°–112° C.

FABMS (m/z): 519 (MH$^+$)

NMR (DMSO-d$_6$) δ: 1.94 (3H, s), 2.05 (3H, s), 2.83 (2H, t, J=7.1 Hz), 3.18 (2H, m), 3.32 (1H, m), 3.53 (1H, m), 3.71 (3H, s), 3.90 (1H, m), 3.96 (1H, dd, J=2.2, 12.4 Hz), 4.09 (1H, dd, J=5.7, 12.0 Hz), 4.69 (1H, dd, J=9.5, 9.8 Hz), 5.08 (1H, d, J=7.8 Hz), 5.47 (1H, d, J=5.7 Hz), 5.58 (1H, d, J=5.6 Hz), 6.57 (1H, d, J=8.1 Hz), 6.66 (1H, d, J=8.1 Hz), 6.82 (2H, ddd, J=2.1, 3.0, 8.7 Hz), 7.16 (2H, ddd, J=2.0, 3.0, 8.6 Hz), 7.24 (1H, t, J=8.3 Hz), 10.82 (1H, s)

Examples 122–124

Using the corresponding starting compounds, the compounds listed in Table 20 are obtained in the same manner as in Example 121.

TABLE 20

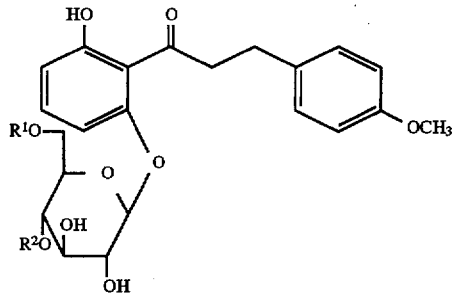

| Ex. No. | $R^1$, $R^2$ | Physical properties |
|---|---|---|
| 122 | $R^1$: $CH_3OCH_2CO-$<br>$R^2$: $CH_3OCH_2CO-$ | NMR (DMSO-d$_6$) δ: 2.83 (2H, t, J = 7.0 Hz), 3.18 (2H, t, J = 7.0 Hz), 3.25 (3H, s), 3.32 |

TABLE 20-continued

| Ex. No. | $R^1$, $R^2$ | Physical properties |
|---|---|---|
| | | (3H, s), 3.33 (1H, m), 3.55 (1H, m), 3.71 (3H, s), 3.93 (2H, d, J = 16.7 Hz), 4.01 (2H, d, J = 16.7 Hz), 4.0–4.1 (2H, m), 4.22 (1H, m), 4.75 (1H, dd, J = 9.5, 9.9 Hz, 5.11 (1H, d, J = 7.9 Hz), 5.53 (1H, d, J = 5.7 Hz), 5.61 (1H, d, J = 5.7 Hz), 6.57 (1H, d, J = 8.1 Hz), 6.66 (1H, d, J = 8.1 Hz), 6.82 (2H, ddd, J = 2.1, 3.0, 8.7 Hz), 7.16 (2H, ddd, J = 2.1, 2.9, 8.7 Hz), 7.24 (1H, t, J = 8.3 Hz), 10.80 (1H, s) FABMS (m/z): 579 [(M+Na)$^+$] |
| 123 | $R^1$: $CH_3CH_2OCH_2CO-$<br>$R^2$: $CH_3CH_2OCH_2CO-$ | NMR (DMSO-d$_6$) δ: 1.08 (3H, t, J = 7.0 Hz), 1.13 (3H, t, J = 7.0 Hz), 2.83 (2H, t, J = 7.5 Hz), 3.18 (2H, t, J = 7.8 Hz), 3.3–3.6 (6H, m), 3.71 (3H, s), 3.9–4.1 (2H, m), 3.96 (1H, d, J = 16.7 Hz), 4.03 (1H, d, J = 16.7 Hz), 4.12 (2H, s), 4.20 (1H, dd, J = 5.4, 12.2 Hz), 4.75 (1H, dd, J = 9.6, 9.7 Hz), 5.11 (1H, d, J = 7.8 Hz), 5.52 (1H, d, J = 5.6 Hz), 5.60 (1H, d, J = 5.7Hz), 6.57 (1H, d, J = 7.7 Hz), 6.66 (1H, d, J = 8.1 Hz), 6.82 (2H, ddd, J = 2.1, 3.0, 8.7 Hz), 7.16 (2H, ddd, J = 2.1, 2.9, 8.7 Hz), 7.23 (1H, t, J = 8.3 Hz), 10.80 (1H, s) FABMS (m/z): 629 [(M+Na)$^+$] |
| 124 | $R^1$: $CH_3CH_2OCO-$<br>$R^2$: $CH_3CH_2OCO-$ | M.p. 89.5–92° C.<br>NMR (DMSO-d$_6$) δ: 1.17 (3H, t, J = 7.1 Hz), 1.23 (3H, t, J = 7.1 Hz), 2.83 (2H, t, J = 7.0 Hz), 3.17 (2H, m), 3.31 (1H, m), 3.54 (1H, m), 3.71 (3H, s), 3.97 (1H, m), 4.06 (2H, q, J = 7.1 Hz), 4.1–4.2 (4H, m), 4.50 (1H, dd, J = 9.6, 9.8 Hz), 5.10 (1H, d, J = 7.9 Hz), 5.57 (1H, d, J = 6.0 Hz), 5.62 (1H, d, J = 5.7 Hz), 6.57 (1H, d, J = 8.1 Hz), 6.65 (1H, d, J = 8.1 Hz), 6.82 (2H, ddd, J = 2.1, 3.0, 8.8 Hz), 7.16 (2H, ddd, J = 2.0, 3.0, 8.7 Hz), 7.22 (1H, t, J = 8.3 Hz), 10.83 (1H, s) FABMS (m/z): 601 [(M+Na)$^+$] |

Reference Example 1

A mixture of 2',6'-dihydroxyacetophenone (1.065 g), cadmium carbonate (4.83 g) and toluene (100 ml) is refluxed while the solvent is removed by using a Dien-Stark trap. After 30 ml of the solvent is removed, 2,3,6-tri-O-acetyl-4-O-(2,3,4,6-tetra-O-acetyl-α-D-glucopyranosyl)-β-D-glucopyranosyl bromide (11.42 g) is added to the mixture, and the mixture is refluxed for 17 hours. After cooling, the insoluble materials are removed by filtration, and the filtrate is concentrated. The residue is purified by silica gel column chromatography to give 2'-O-[2,3,6-tri-O-acetyl-4-O-(2,3,4,6-tetra-O-acetyl-α-D-glucopyranosyl)-β-D-glucopyranosyl]-6'-hydroxyacetophenone (4.30 g).

IR (nujol) cm$^{-1}$: 1750, 1630

NMR (CDCl$_3$) δ: 2.01 (3H, s), 2.03 (6H, s), 2.04 (3H, s), 2.06 (3H, s), 2.08 (3H, s), 2.10 (3H, s), 2.59 (3H, s), 3.8–4.35 (6H, m), 4.46 (1H, dd, J=2.9, 12.2 Hz), 4.87 (1H, dd, J=4.2, 10.5 Hz), 5.06 (1H, t, J=9.8 Hz), 5.21 (1H, d, J=7.3 Hz), 5.32 (1H, d, J=2.5 Hz), 5.35–5.47 (3H, m), 6.49 (1H, d, J=8.3 Hz), 6.71 (1H, d, J=8.3 Hz), 7.36 (1H, t, J=8.3 Hz), 12.96 (1H, s)

FABMS (m/z): 793 [(M+Na)$^+$]

Reference Example 2

To a mixture or 6'-hydroxy-2'-O-(2,3,4,6-tetra-O-acetyl-β-D-glucopyranosyl)acetophenone (2.41 g), p-anisaldehyde (1.36 g) and ethanol (25 ml) is added dropwise with stirring a 50% aqueous potassium hydroxide solution (2.5 ml), and the mixture is stirred at room temperature overnight. The mixture is concentrated under reduced pressure, and to the resulting residue are added water (100 m) and diethyl ether (50 ml), and the mixture is stirred. The aqueous layer is collected, and neutralized with a 10% hydrochloric acid under ice-cooling, and thereto is added ethyl acetate (200 ml). The mixture is stirred, and the organic layer is collected, washed with water, dried, and filtered. The filtrate is concentrated under reduced pressure, and the residue is dissolved in ethanol (50 ml). The mixture is subjected to catalytic hydrogenation under atmospheric pressure with 10% palladium-carbon. The catalyst is removed by filtration, and the filtrate is concentrated under reduced pressure. The residue is purified by silica gel column chromatography (solvent; chloroform/methanol) to give 4-methoxy-6'-hydroxy-2'-O-β-D-glucopyranosyldihydrochalcone (1.02 g) as white crystalline powders.

M.p. 127°–129° C.

FABMS (m/z): 435 (MH⁺)

NMR (DMSO-d₆) δ: 2.84 (2H, t, J=7.3 Hz), 3.19–3.49 (7H, m), 3.7 (1H, m), 3.71 (3H, s), 4.56 (1H, t, J=5.4 Hz), 4.91 (1H, d, J=7.3 Hz), 5.03 (1H, d, J=4.9 Hz), 5.10 (1H, d, J=4.4 Hz), 5.22 (1H, d, J=4.9 Hz), 6.55 (1H, d, J=8.3 Hz), 6.67 (1H, d, J=8.3 Hz), 6.81 (2H, d, J=8.8 Hz), 7.17 (2H, d, J=8.8 Hz), 7.24 (1H, t, J=8.3 Hz), 10.99 (1H, s)

Reference Examples 3–4

Using the corresponding starting compounds, the compounds listed in Table 21 are obtained in the same manner as in Reference Example 2.

TABLE 21

| Ref. Ex. No. | Y | Physical properties |
|---|---|---|
| 3 | 4-HO— | M.p. 171–174° C.<br>NMR (DMSO-d₆) δ: 2.78 (2H, t, J = 7.6 Hz), 3.20 (2H, t, J = 7.6 Hz), 3.1–3.5 (5H, m), 3.70 (1H, dd, J = 4.6, 11.0 Hz), 4.56 (1H, t, J = 5.6 Hz), 4.91 (1H, d, J = 6.8 Hz), 5.03 (1H, d, J = 4.9 Hz), 5.09 (1H, d, J = 3.9 Hz), 5.22 (1H, d, J = 4.9 Hz), 6.54 (1H, d, J = 8.3 Hz), 6.64 (2H, d, J = 8.8 Hz), 6.67 (1H, d, J = 8.3 Hz), 7.03 (2H, d, J = 8.3 Hz), 7.24 (1H, t, J = 8.3 Hz), 9.09 (1H, bro), 11.00 (1H, bro)<br>IR (nujol) cm⁻¹: 3600–3000, 1620<br>FABMS (m/z): 443 [(M+Na)⁺], 421 (MH⁺) |
| 4 | H— | M.p. 126–129° C.<br>NMR (DMSO-d₆) δ: 2.90 (2H, t, J = 7.6 Hz), 3.23 (2H, t, J = 7.8 Hz), 3.1–3.5 (5H, m), 3.70 (1H, dd,J = 5.1, 10.5 Hz), 4.55 (1H, t, J = 5.6 Hz), 4.91 (1H, d, J = 7.3 Hz), 5.02 (1H, d, J = 4.9 Hz), 5.09 (1H, d, J = 4.4 Hz), 5.23 (1H, d, J = 5.4 Hz), 6.55 (1H, d, J = 8.3 Hz), 6.68 (1H, d, J = 8.3 Hz), 7.11–7.28 (6H, m), 10.97 (1H, s)<br>IR (nujol) cm⁻¹: 3480–3280, 1630<br>FABMS (m/z): 405 (MH⁺) |

Effects of the Invention

The dihydrochalcone derivatives [I], which are active ingredients of the present invention, have urine glucose increasing activity being based on the inhibitory activity of renal glucose reabsorption thereof, by which they show excellent hypoglycemic activity. In addition, the dihydrochalcone derivatives [I] are hardly hydrolyzed at the intestine unlike phlorizin, and hence, they can be used in the prophylaxis or treatment of diabetes either by oral administration or by parenteral administration. Moreover, the active dihydrochalcone derivatives [I] have low toxicity, and the aglycone, a hydrolysate thereof, show extremely weak inhibitory effect on the glucose-uptake, and hence, the active dihydrochalcone derivatives [I] and pharmaceutically acceptable salts thereof show high safety as medicine.

What is claimed is:

1. A method for the treatment of diabetes mellitus, which comprises administering to a patient with diabetes an effective amount of a dihydrochalcone compound of formula (I):

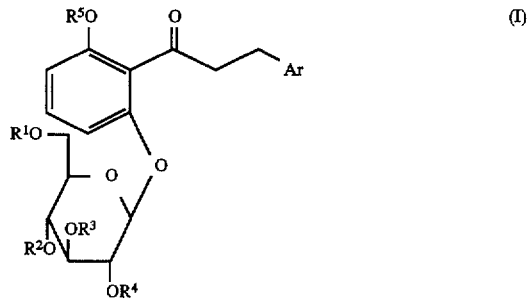

wherein Ar is an aryl group, $R^1$ is a hydrogen atom or an acyl group, $R^2$ is a hydrogen atom, an acyl group or an α-D-glucopyranosyl group, or $R^1$ and $R^2$ may combine together to form a substituted methylene group, $R^3$ and $R^4$ are each a hydrogen atom or an acyl group, and $OR^5$ is a protected or unprotected hydroxy group or a lower alkoxy group; or a pharmaceutically acceptable salt thereof.

2. The method according to claim 1, wherein the aryl group is a substituted or unsubstituted hydrocarbon aryl group or a substituted or unsubstituted heterocyclic aryl group, and the acyl group is a substituted or unsubstituted aliphatic group or a substituted or unsubstituted aromatic acyl group.

3. The method according to claim 2, wherein the hydrocarbon aryl group is a substituted or unsubstituted phenyl group or a substituted or unsubstituted naphthyl group, the heterocyclic aryl group is a substituted or unsubstituted heterocyclic group containing as a heteroatom an oxygen atom, a nitrogen atom or a sulfur atom, the aliphatic acyl group is a substituted or unsubstituted lower alkanoyl group or a substituted or unsubstituted lower alkoxycarbonyl group, and the aromatic acyl group is a substituted or unsubstituted benzoyl group or a substituted or unsubstituted phenoxycarbonyl group.

4. The method according to claim 3, wherein Ar is a substituted or unsubstituted phenyl group, a heterocyclic group containing as a heteroatom an oxygen atom, a nitrogen atom or a sulfur atom, or a naphthyl group, $OR^5$ is a protected or unprotected hydroxy group or a lower alkoxy group, and $R^1$, $R^2$, $R^3$ and $R^4$ are each a hydrogen atom.

5. The method according to claim 3, wherein Ar is a substituted or unsubstituted phenyl group, $OR^5$ is a protected or unprotected hydroxy group or a lower alkoxy group, $R^1$, $R^3$, and $R^4$ are each a hydrogen atom and $R^2$ is an α-D-glucopyranosyl group.

6. The method according to claim 3, wherein Ar is a substituted or unsubstituted phenyl group, $OR^5$ is a protected or unprotected hydroxy group or a lower alkoxy group, $R^1$ and $R^2$ are both hydrogen atoms, and $R^3$ and $R^4$ are each a substituted or unsubstituted lower alkanoyl group, a substituted or unsubstituted lower alkoxycarbonyl group, an arylcarbonyl group, or an aryloxycarbonyl group.

7. The method according to claim 3, wherein Ar is a substituted or unsubstituted phenyl group, $OR^5$ is a protected or unprotected hydroxy group or a lower alkoxy group, $R^1$ is a substituted or unsubstituted lower alkanoyl group, a substituted or unsubstituted lower alkoxycarbonyl group, an arylcarbonyl group or an alkoxycarbonyl group, and $R^2$, $R^3$ and $R^4$ are the same or different and are each a hydrogen atom, a substituted or unsubstituted lower alkanoyl group, a substituted or unsubstituted lower alkoxycarbonyl group, an arylcarbonyl group, or an aryloxycarbonyl group.

8. The method according to any one of claims 3 to 7, wherein the substituted phenyl, naphthyl, heterocyclic aryl, lower alkanoyl, lower alkoxycarbonyl, benzoyl, phenoxycarbonyl and methylene groups are those substituted by a substituent selected from the group consisting of an unsubstituted lower alkyl group, a lower alkyl group having a hydroxy substituent or a halogen substituent; an unsubstituted lower alkoxy group, a lower alkoxy group having a lower alkoxy substituent; an unsubstituted lower alkoxycarbonyloxy group, a lower alkoxy carbonyloxy group having a lower alkoxy substituent; an amino group having a lower alkyl substituent; a protected or unprotected amino group; an unsubstituted lower alkanoyloxy group, a lower alkanoyloxy group having 1 to 2 substituents selected from a lower alkoxy group, a lower alkoxycarbonyl group, an amino group and a phenyl group; a halogen atom; hydroxy group; carbamoyl group; a lower alkylthio group; a lower alkylsulfinyl group; a lower alkylsulfonyl group; carboxyl group; formyl group; cyano group; di-lower alkylcarbamoyloxy group; phenoxycarbonyloxy group; phenyl group; phenoxy group; oxo group; a lower alkylenedioxy group; a benzoyloxy group or a benzoyloxy group having a lower alkoxy substituent.

9. The method according to claim 4, wherein Ar is a phenyl group, a lower alkyl-substituted phenyl group, a lower alkoxy-substituted phenyl group, a lower alkoxycarbonyloxy-substituted phenyl group or a halogenophenyl group, $OR^5$ is a protected or unprotected hydroxy group, and $R^1$, $R^2$, $R^3$ and $R^4$ are each a hydrogen atom.

10. The method according to claim 6, wherein Ar is an unsubstituted phenyl group or a phenyl group substituted by a substituent selected from the group consisting of a halogen atom, hydroxy group, a lower alkyl group, a lower alkoxy group, a lower alkanoyloxy group and a lower alkoxycarbonyloxy group, $OR^5$ is a protected or unprotected hydroxy group or a lower alkoxy group, $R^1$ and $R^2$ are both hydrogen atoms, and $R^3$ and $R^4$ are each an unsubstituted lower alkanoyl group, a lower alkanoyl group substituted by a substituent selected from the group consisting of a lower alkoxy group, and amino group, a lower alkoxycarbonyl group, benzoyl group or phenoxycarbonyl group.

11. The method according to claim 10, wherein Ar is an unsubstituted phenyl group or a phenyl group substituted by a lower alkyl group or a lower alkoxy group, $OR^5$ is a hydroxy group or a hydroxy group protected by a lower alkanoyl group, $R^1$ and $R^2$ are both hydrogen atoms, and $R^3$ and $R^4$ are each a lower alkanoyl group, a lower alkoxy-substituted lower alkanoyl group, an amino-substituted lower alkanoyl group, a lower alkoxycarbonyl group or phenoxycarbonyl group.

12. The method according to claim 11, wherein Ar is a lower alkoxy-substituted phenyl group, and $R^3$ and $R^4$ are each a lower alkoxy-substituted lower alkanoyl group.

13. A compound of the formula (I-a):

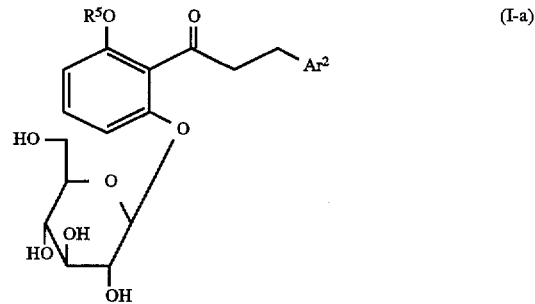

wherein $Ar^2$ is an aryl group other than a phenyl group, a 4-hydroxyphenyl group or a 4-methoxyphenyl group, and $OR^5$ is a protected or unprotected hydroxy group or a lower alkoxy group.

14. The compound according to claim 13, wherein the aryl group is a substituted or unsubstituted hydrocarbon aryl group or a substituted or unsubstituted heterocyclic aryl group.

15. The compound according to claim 14, wherein the hydrocarbon aryl group is a substituted or unsubstituted phenyl group or a substituted or unsubstituted naphthyl group, the heterocyclic aryl group is a substituted or unsubstituted heterocyclic group containing an oxygen atom, a nitrogen atom or a sulfur atom as a heteroatom.

16. The compound according to claim 15, wherein the substituted phenyl, naphthyl and heterocyclic aryl groups are those substituted by:

a lower alkyl group; a lower alkyl group substituted by a hydroxy group or a halogen atom; a lower alkoxy group; a lower alkoxy group having a lower alkoxy substituent; a lower alkoxycarbonyloxy group; a lower alkoxycarbonyloxy group having a lower alkoxy substituent; an amino group having a lower alkyl substituent; a protected or unprotected amino group; a lower alkanoyloxy group; a lower alkanoyloxy group having 1 to 2 substituents selected from the group consisting of a lower alkoxy group, a lower alkoxycarbonyl group, amino group and phenyl group; a halogen atom; hydroxy group; carbamoyl group; a lower alkylthio group; a lower alkylsulfinyl group; a lower alkylsulfonyl group; carboxyl group; formyl group; cyano group; di-lower alkylcarbamoyloxy group; phenoxycarbonyloxy group; a lower alkylenedioxy group; a benzoyloxy group or a benzyloxy group having a lower alkoxy substituent.

17. The compound according to claim 16, wherein $Ar^2$ is a phenyl group substituted by 1 to 2 substituents selected from the group consisting of:

a lower alkyl group; a lower alkyl group substituted by a halogen atom or hydroxy group; a lower alkoxy group having 2 to 6 carbon atoms; a lower alkoxy group substituted by a lower alkoxy group; a lower alkoxycarbonyloxy group; a lower alkoxycarbonyloxy group substituted by a lower alkoxy group; an amino group substituted by a lower alkyl group or a lower alkanoyl group; a lower alkanoyloxy group; a lower alkanoyloxy group substituted by 1 to 2 substituents selected from the group consisting of a lower alkoxy group, a lower alkoxycarbonyl group, amino group and phenyl group;

a halogen atom; hydroxy group; carbamoyl group; a lower alkylthio group; a lower alkylsulfinyl group; a lower alkylsulfonyl group; a carboxyl group; a formyl group; a cyano group; a di-lower alkylcarbamoyloxy group; phenoxycarbonyloxy group; a lower alkylenedioxy group; benzoyloxy; benzoyloxy substituted by a lower alkoxy group;

furyl group; thienyl group; pyridyl group; or a naphthyl group; and $OR^5$ is a protected or unprotected hydroxy group or a lower alkoxy group.

18. The compound according to claim 17, wherein $Ar^2$ is a $C_{1-3}$ alkyl-phenyl group, a $C_{2-3}$ alkoxy-phenyl group, a $C_{1-6}$ alkoxy-carbonyloxy-phenyl group or a halogenophenyl group, and $OR^5$ is a protected or unprotected hydroxy group.

19. A pharmaceutical composition which comprises a therapeutically effective amount of the compound as set forth in claim 13 in admixture with a pharmaceutically acceptable carrier or diluent.

* * * * *